United States Patent
Fauth et al.

(10) Patent No.: US 8,998,952 B2
(45) Date of Patent: *Apr. 7, 2015

(54) FACET JOINT REPLACEMENT INSTRUMENTS AND METHODS

(75) Inventors: Andrew R. Fauth, River Heights, UT (US); Daniel J. Triplett, Providence, UT (US); Joel R. Helgerson, Providence, UT (US); Daniel E. Gerbec, Logan, UT (US)

(73) Assignee: Globus Medical, Inc., Audubon, PA (US)

(*) Notice: Subject to any disclaimer, the term of this patent is extended or adjusted under 35 U.S.C. 154(b) by 817 days.

This patent is subject to a terminal disclaimer.

(21) Appl. No.: 12/630,534

(22) Filed: Dec. 3, 2009

(65) Prior Publication Data

US 2010/0082107 A1   Apr. 1, 2010

Related U.S. Application Data

(63) Continuation-in-part of application No. 12/240,320, filed on Sep. 29, 2008, now Pat. No. 8,906,063, which is a continuation-in-part of application No. 10/860,487, filed on Jun. 2, 2004, now Pat. No.

(Continued)

(51) Int. Cl.
*A61B 17/70* (2006.01)
*A61B 17/16* (2006.01)
(Continued)

(52) U.S. Cl.
CPC ......... *A61B 17/1671* (2013.01); *A61B 17/7064* (2013.01); *A61F 2/4405* (2013.01); *A61F 2/4611* (2013.01); *A61B 17/7049* (2013.01); *A61B 17/7067* (2013.01); *A61B 17/8625* (2013.01); *A61B 17/8695* (2013.01); *A61B 2017/8655* (2013.01); *A61F 2/30771* (2013.01); *A61F 2002/30125* (2013.01); *A61F 2002/30154* (2013.01); *A61F 2002/30156* (2013.01); (Continued)

(58) Field of Classification Search
USPC .................. 606/53, 60, 246–279, 86 A
See application file for complete search history.

(56) References Cited

U.S. PATENT DOCUMENTS 5,593,416 A * 1/1997 Donahue ................. 606/170
6,189,422 B1   2/2001 Stihl
(Continued)

FOREIGN PATENT DOCUMENTS

DE   9308770 u1 * 8/1993

OTHER PUBLICATIONS

IPRP and Written Opinion in matter PCT/US2009/066761.
(Continued)

*Primary Examiner* — Pedro Philogene
*Assistant Examiner* — Lynnsy Summitt

(57) ABSTRACT

A facet joint replacement system includes an inferior implant with an inferior articular surface, a superior implant with a superior articular surface, and an optional crossbar. The inferior implant and the superior implant are each polyaxially adjustably connected to fixation elements which anchor the implants to adjacent vertebrae. The optional crossbar may be polyaxially adjustably connected to bilateral implants. The system components may be provided in kits which provide components of various sizes and shapes. A set of surgical instruments may facilitate implantation of the facet joint replacement system by providing tools for bone preparation, trialing, implant insertion, implant alignment, and lock-out of modular interconnections.

11 Claims, 70 Drawing Sheets

Related U.S. Application Data 8,926,700, application No. 12/630,534, which is a continuation-in-part of application No. 12/201,046, filed on Aug. 29, 2008, now Pat. No. 8,308,768, and a continuation-in-part of application No. 12/201,086, filed on Aug. 29, 2008, and a continuation-in-part of application No. 12/201,128, filed on Aug. 29, 2008, now Pat. No. 8,252,027, and a continuation-in-part of application No. 12/201,148, filed on Aug. 29, 2008, now Pat. No. 8,206,418, and a continuation-in-part of application No. 12/201,198, filed on Aug. 29, 2008, now Pat. No. 8,211,147, said application No. 12/201,046 is a continuation-in-part of application No. 12/104,726, filed on Apr. 17, 2008, now Pat. No. 8,353,933, said application No. 12/201,086 is a continuation-in-part of application No. 12/104,726, filed on Apr. 17, 2008, now Pat. No. 8,353,933, said application No. 12/201,128 is a continuation-in-part of application No. 12/104,726, filed on Apr. 17, 2008, now Pat. No. 8,353,933, said application No. 12/201,148 is a continuation-in-part of application No. 12/104,726, filed on Apr. 17, 2008, now Pat. No. 8,353,933, said application No. 12/201,198 is a continuation-in-part of application No. 12/104,726, filed on Apr. 17, 2008, now Pat. No. 8,353,933, said application No. 12/201,046 is a continuation-in-part of application No. 12/104,855, filed on Apr. 17, 2008, now Pat. No. 8,333,789, said application No. 12/201,086 is a continuation-in-part of application No. 12/104,855, filed on Apr. 17, 2008, now Pat. No. 8,333,789, said application No. 12/201,128 is a continuation-in-part of application No. 12/104,855, filed on Apr. 17, 2008, now Pat. No. 8,333,789, said application No. 12/201,148 is a continuation-in-part of application No. 12/104,855, filed on Apr. 17, 2008, now Pat. No. 8,333,789, said application No. 12/201,198 is a continuation-in-part of application No. 12/104,855, filed on Apr. 17, 2008, now Pat. No. 8,333,789, said application No. 12/201,086 is a continuation-in-part of application No. 11/972,158, filed on Jan. 10, 2008, now Pat. No. 8,900,273, said application No. 12/104,855 is a continuation-in-part of application No. 11/972,158, filed on Jan. 10, 2008, now Pat. No. 8,900,273, said application No. 11/972,158 is a continuation-in-part of application No. 11/063,941, filed on Feb. 22, 2005, now Pat. No. 7,993,373, and a continuation-in-part of application No. 11/312,323, filed on Dec. 19, 2005, now Pat. No. 8,062,336, which is a continuation-in-part of application No. 11/063,941, filed on Feb. 22, 2005, now Pat. No. 7,993,373.

(60) Provisional application No. 60/545,094, filed on Feb. 17, 2004, provisional application No. 60/545,101, filed on Feb. 17, 2004, provisional application No. 61/023,927, filed on Jan. 28, 2008, provisional application No. 61/033,473, filed on Mar. 4, 2008, provisional application No. 61/040,041, filed on Mar. 27, 2008, provisional application No. 61/042,896, filed on Apr. 7, 2008, provisional application No. 61/042,869, filed on Apr. 7, 2008, provisional application No. 61/045,526, filed on Apr. 16, 2008, provisional application No. 60/884,233, filed on Jan. 10, 2007, provisional application No. 60/912,323, filed on Apr. 17, 2007, provisional application No. 60/968,324, filed on Aug. 28, 2007, provisional application No. 60/950,012, filed on Jul. 16, 2007, provisional application No. 60/950,021, filed on Jul. 16, 2007, provisional application No. 60/950,031, filed on Jul. 16, 2007, provisional application No. 60/950,038, filed on Jul. 16, 2007, provisional application No. 60/957,505, filed on Aug. 23, 2007, provisional application No. 60/968,925, filed on Aug. 30, 2007, provisional application No. 61/015,866, filed on Dec. 21, 2007, provisional application No. 61/015,876, filed on Dec. 21, 2007, provisional application No. 60/975,731, filed on Sep. 27, 2007, provisional application No. 60/984,798, filed on Nov. 2, 2007, provisional application No. 60/984,814, filed on Nov. 2, 2007, provisional application No. 60/984,983, filed on Nov. 2, 2007, provisional application No. 60/984,434, filed on Nov. 1, 2007, provisional application No. 60/984,428, filed on Nov. 1, 2007, provisional application No. 60/984,594, filed on Nov. 1, 2007, provisional application No. 61/014,344, filed on Dec. 17, 2007, provisional application No. 61/015,886, filed on Dec. 21, 2007, provisional application No. 61/015,840, filed on Dec. 21, 2007.

(51) Int. Cl.
*A61F 2/44* (2006.01)
*A61F 2/46* (2006.01)
*A61B 17/86* (2006.01)
*A61F 2/30* (2006.01)

(52) U.S. Cl.
CPC .............. *A61F2002/30171* (2013.01); *A61F 2002/30426* (2013.01); *A61F 2002/30433* (2013.01); *A61F 2002/30448* (2013.01); *A61F 2002/30514* (2013.01); *A61F 2002/30576* (2013.01); *A61F 2002/30578* (2013.01); *A61F 2002/30579* (2013.01); *A61F 2002/30616* (2013.01); *A61F 2002/30841* (2013.01); *A61F 2002/3085* (2013.01); *A61F 2002/4622* (2013.01); *A61F 2220/0025* (2013.01); *A61F 2220/0041* (2013.01); *A61F 2220/005* (2013.01); *A61F 2230/0008* (2013.01); *A61F 2230/0021* (2013.01); *A61F 2230/0023* (2013.01); *A61F 2230/005* (2013.01); *A61F 2310/00017* (2013.01); *A61F 2310/00023* (2013.01); *A61F 2310/00203* (2013.01); *A61F 2310/00239* (2013.01); *A61F 2310/00796* (2013.01)

(56) References Cited

U.S. PATENT DOCUMENTS

| | | | | |
|---|---|---|---|---|
| 6,251,111 | B1 * | 6/2001 | Barker et al. | 606/86 A |
| 6,319,257 | B1 * | 11/2001 | Carignan et al. | 606/99 |
| 7,051,451 | B2 * | 5/2006 | Augostino et al. | 33/512 |
| 7,572,276 | B2 * | 8/2009 | Lim et al. | 606/246 |
| 7,588,588 | B2 * | 9/2009 | Spitler et al. | 606/246 |
| 7,588,589 | B2 * | 9/2009 | Falahee | 606/247 |
| 7,618,442 | B2 * | 11/2009 | Spitler et al. | 606/266 |
| 7,618,444 | B2 * | 11/2009 | Shluzas | 606/279 |
| 7,947,063 | B2 * | 5/2011 | Arnin | 606/247 |
| 7,998,175 | B2 * | 8/2011 | Kim | 606/257 |
| 8,007,519 | B2 * | 8/2011 | Hudgins et al. | 606/255 |
| 2003/0073998 | A1 * | 4/2003 | Pagliuca et al. | 606/61 |
| 2004/0147928 | A1 * | 7/2004 | Landry et al. | 606/61 |
| 2005/0228400 | A1 | 10/2005 | Chao et al. | |
| 2006/0079903 | A1 | 4/2006 | Wong | |
| 2006/0173454 | A1 * | 8/2006 | Spitler et al. | 606/61 |
| 2006/0200137 | A1 * | 9/2006 | Soboleski et al. | 606/61 |
| 2007/0162003 | A1 * | 7/2007 | Tornier et al. | 606/61 |
| 2008/0039847 | A1 * | 2/2008 | Piper et al. | 606/69 |

(56) References Cited

U.S. PATENT DOCUMENTS

| | | | |
|---|---|---|---|
| 2008/0177311 A1* | 7/2008 | Winslow et al. | 606/248 |
| 2008/0177334 A1* | 7/2008 | Stinnette | 606/304 |
| 2008/0200918 A1 | 8/2008 | Spitler et al. | |
| 2008/0255574 A1* | 10/2008 | Dye | 606/99 |
| 2008/0282846 A1 | 11/2008 | Sharifi-Mehr et al. | |
| 2008/0300631 A1* | 12/2008 | Tornier | 606/246 |
| 2009/0163963 A1 | 6/2009 | Berrevoets | |

OTHER PUBLICATIONS

ISR in matter PCT/US2009/066761.

* cited by examiner

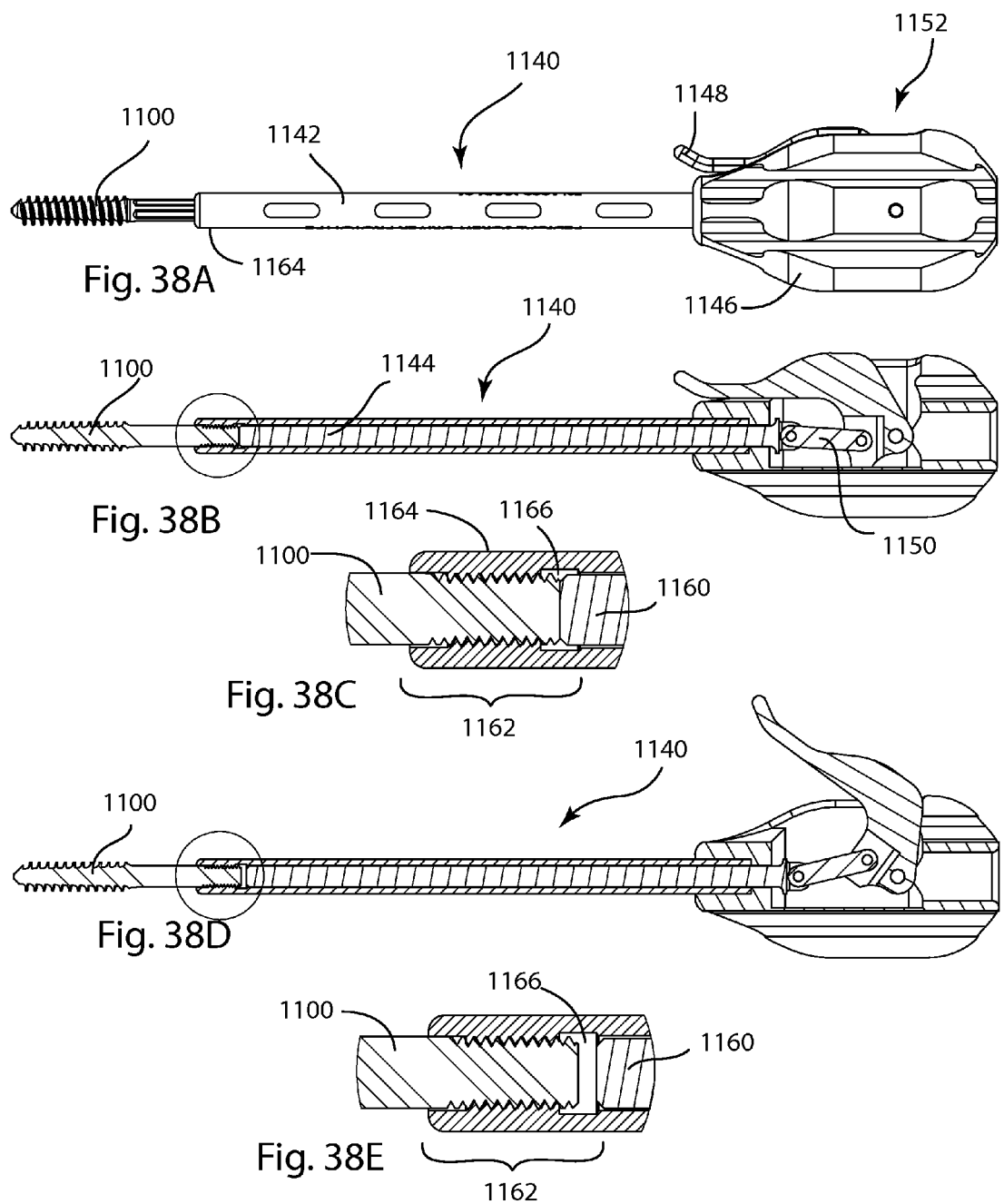

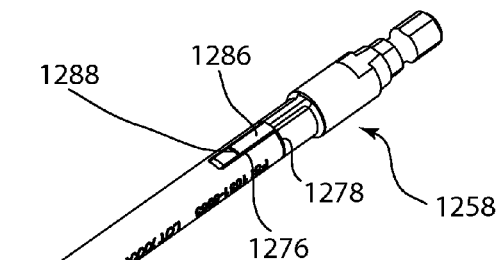
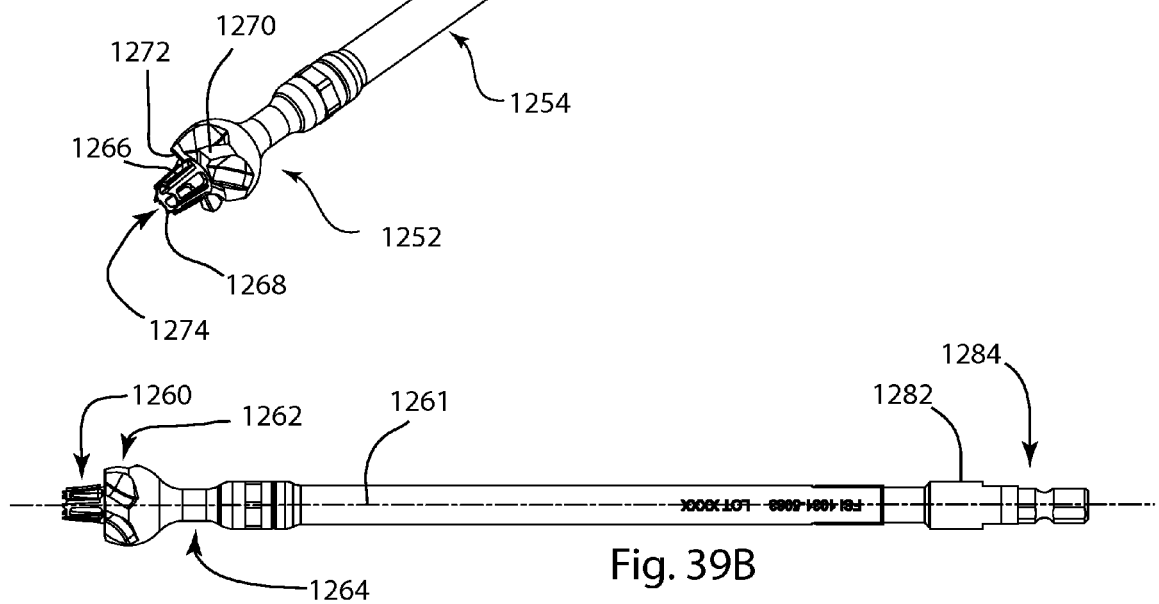
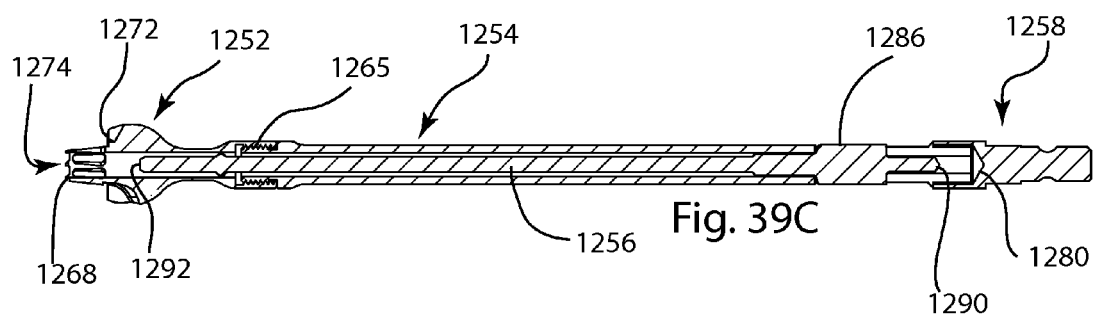
Fig. 39A
Fig. 39B
Fig. 39C

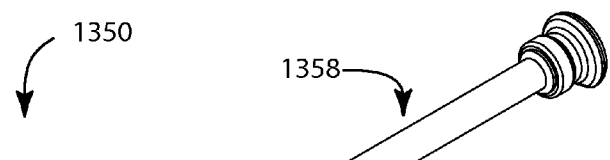
Fig. 40A
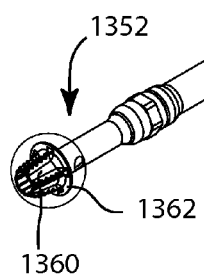
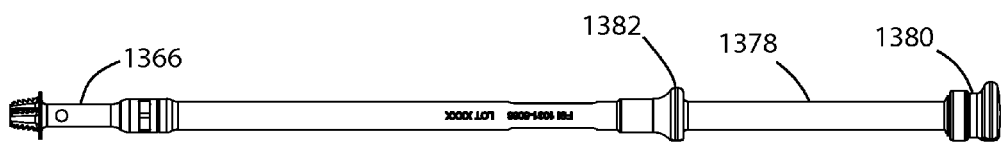
Fig. 40B
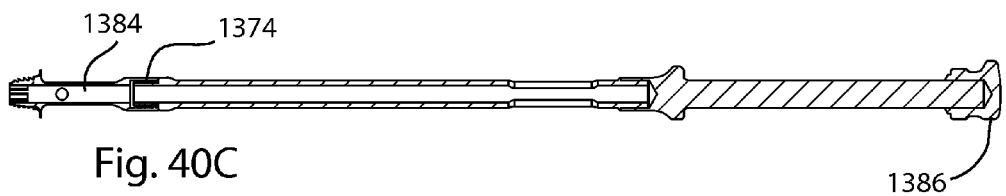
Fig. 40C

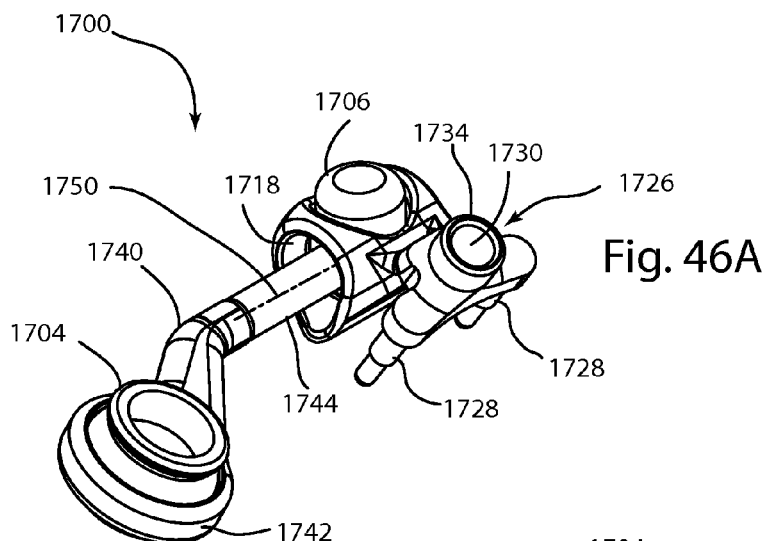
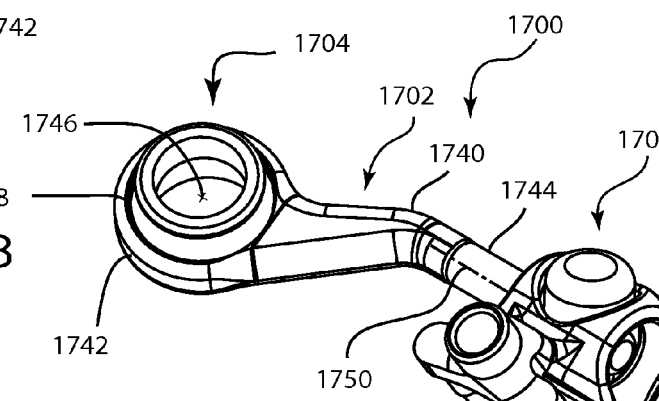
Fig. 46A
Fig. 46B
Fig. 46C

FACET JOINT REPLACEMENT INSTRUMENTS AND METHODS

CROSS-REFERENCE TO RELATED APPLICATIONS

This application is a continuation-in-part of:

U.S. application Ser. No. 12/240,320, filed Sep. 29, 2008, entitled SPINAL FACET JOINT IMPLANT, which is pending.

U.S. application Ser. No. 12/240,320 is a divisional of U.S. application Ser. No. 10/860,487, filed Jun. 2, 2004, entitled SPINAL FACET JOINT IMPLANT, which is pending.

U.S. application Ser. No. 10/860,487 claims the benefit of:

U.S. Application No. 60/545,101, filed Feb. 17, 2004, entitled SPHERICAL IMPLANT AND BONE BED; and U.S. Application No. 60/545,094, filed Feb. 17, 2004, entitled SPHERICAL ARTICULATING IMPLANT SURFACE.

This application is also a continuation-in-part of:

U.S. application Ser. No. 12/201,046, filed Aug. 29, 2008, entitled SYSTEM AND METHOD FOR FACET JOINT REPLACEMENT, which is pending;

U.S. application Ser. No. 12/201,086, filed Aug. 29, 2008, entitled SYSTEM AND METHOD FOR IMPLANT ANCHORAGE WITH ANTI-ROTATION FEATURES, which is pending;

U.S. application Ser. No. 12/201,128, filed Aug. 29, 2008, entitled SYSTEM AND METHOD FOR FACET JOINT REPLACEMENT, which is pending;

U.S. application Ser. No. 12/201,148, filed Aug. 29, 2008, entitled SYSTEM AND METHOD FOR FACET JOINT REPLACEMENT WITH DETACHABLE COUPLER, which is pending; and U.S. application Ser. No. 12/201,198, filed Aug. 29, 2008, entitled SYSTEM AND METHOD FOR FACET JOINT REPLACEMENT, which is pending.

U.S. application Ser. Nos. 12/201,046; 12/201,086; 12/201,128; 12/201,148; and Ser. No. 12/201,198 are continuations-in-part of:

U.S. application Ser. No. 12/104,726, filed Apr. 17, 2008, entitled FACET JOINT REPLACEMENT, which is pending; and U.S. application Ser. No. 12/104,855, filed Apr. 17, 2008, entitled FACET JOINT REPLACEMENT, which is pending.

U.S. application Ser. Nos. 12/201,086; 12/201,128; 12/201,148; 12/104,726; and 12/104,855 claim the benefit of:

U.S. Application No. 61/023,927, filed Jan. 28, 2008, entitled AFRS GENERATION II INSTRUMENTS;

U.S. Application No. 61/033,473, filed Mar. 4, 2008, entitled TOP LOADING RECEIVER FOR AN ADJUSTABLE FACET REPLACEMENT;

U.S. Application No. 61/040,041, filed Mar. 27, 2008, entitled FACET JOINT REPLACEMENT;

U.S. Application No. 61/042,896, filed Apr. 7, 2008, entitled SPINAL FIXATION ON AN IMPLANT BASE; and U.S. Application No. 61/045,526, filed Apr. 16, 2008, entitled INFERIOR BASE-SPLIT CLAMP AND MULTI-LEVEL SPLIT CLAMP.

U.S. application Ser. Nos. 12/104,726 and 12/104,855 are also continuations-in-part of U.S. application Ser. No. 11/972,158, filed Jan. 10, 2008, entitled TAPER-LOCKING FIXATION SYSTEM, which is pending.

U.S. application Ser. No. 11/972,158 claims the benefit of:

U.S. Application No. 60/884,233, filed Jan. 10, 2007, entitled TAPER-LOCKING ROD FIXATION SYSTEM;

U.S. Application No. 60/912,323, filed Apr. 17, 2007, entitled AFRS MULTI-LEVEL IMPLANT SYSTEM;

U.S. Application No. 60/968,324, filed Aug. 28, 2007, entitled INTERVERTEBRAL DISC IMPLANT WITH FACET MOTION CONSTRAINTS;

U.S. Application No. 60/950,012, filed Jul. 16, 2007, entitled INFERIOR FACET IMPLANT HOLDER WITH CLAMP RETENTION;

U.S. Application No. 60/950,021, filed Jul. 16, 2007, entitled MONORAIL INSTRUMENT GUIDANCE SYSTEM FOR LUMBAR SPINAL SURGERY;

U.S. Application No. 60/950,031, filed Jul. 16, 2007, entitled LINEAR POLYAXIAL LOCKING MECHANISM WITH TOOL;

U.S. Application No. 60/950,038, filed Jul. 16, 2007, entitled MOBILE INFERIOR FACET BEARING WITH SUPERIOR CLIP;

U.S. Application No. 60/957,505, filed Aug. 23, 2007, entitled DYNAMIC STABILIZATION AND STATIC FIXATION OPTIONS FOR FACET REPLACEMENT PROSTHESIS;

U.S. Application No. 60/968,925, filed Aug. 30, 2007, entitled SYSTEMS AND METHODS FOR LESS INVASIVE FACET JOINT REPLACEMENT;

U.S. Application No. 61/015,866, filed Dec. 21, 2007, entitled INTERVERTEBRAL DISC IMPLANT WITH FACET MOTION CONSTRAINTS INCLUDING POSTERIOR COMBINATION DISCS;

U.S. Application No. 61/015,876, filed Dec. 21, 2007, entitled INTERVERTEBRAL DISC IMPLANT WITH FACET MOTION CONSTRAINTS AND METHODS FOR IMPLANT ALIGNMENT;

U.S. Application No. 60/975,731, filed Sep. 27, 2007, entitled MONOLITHIC INFERIOR IMPLANT STRUT WITH INTEGRAL CROSS LINK CLAMP;

U.S. Application No. 60/984,798, filed Nov. 2, 2007, entitled LOW PROFILE POLYAXIAL FACET IMPLANT;

U.S. Application No. 60/984,814, filed Nov. 2, 2007, entitled HINGED EYELET SCREW;

U.S. Application No. 60/984,983, filed Nov. 2, 2007, entitled ADJUSTABLE FACET IMPLANT BASE PIECE;

U.S. Application No. 60/984,434, filed Nov. 1, 2007, entitled SUPERIOR INSTRUMENT;

U.S. Application No. 60/984,428, filed Nov. 1, 2007, entitled CROSS LINK CLAMP;

U.S. Application No. 60/984,594, filed Nov. 1, 2007, entitled ADJUSTABLE INFERIOR FACET REPLACEMENT WITH MEDIAL-LATER SLIDE ADJUSTMENT;

U.S. Application No. 61/014,344, filed Dec. 17, 2007, entitled INFERIOR STRUT UPDATE;

U.S. Application No. 61/015,886, filed Dec. 21, 2007, entitled EYELET PEDICLE SCREW WITH MULTI-AXIAL FIXATION; and U.S. Application No. 61/015,840, filed Dec. 21, 2007, entitled CERVICAL PLATE WITH FACET MOTION CONTROL, U.S. application Ser. No. 11/972,158 is a continuation-in-part of U.S. Application No. Ser. No. 11/063,941, filed Feb. 22, 2005, entitled POLYAXIAL ORTHOPEDIC FASTENING APPARATUS, which is pending; and U.S. application Ser. No. 11/312,323, filed Dec. 19, 2005, entitled POLYAXIAL ORTHOPEDIC FASTENING APPARATUS WITH INDEPENDENT LOCKING MODES, which is pending.

U.S. application Ser. No. 11/312,323 is a continuation-in-part of U.S. application Ser. No. 11/063,941, filed Feb. 22, 2005, entitled POLYAXIAL ORTHOPEDIC FASTENING APPARATUS, which is pending.

All of the above-referenced documents are hereby incorporated by reference in their entirety.

BACKGROUND OF THE INVENTION

1. The Field of the Invention

The invention relates to spinal surgery. More specifically, the invention relates to replacement of natural vertebral facet joints with implantable artificial facet joint replacements.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 38A is a side view of the screw driver of FIG. 37B; FIG. 38B is a cross-sectional view of the screw driver of FIG. 38A in a locked configuration with a fixation element; FIG. 38C is a detail cross-sectional view of the distal end of the screw driver of FIG. 38B; FIG. 38D is a cross-sectional view of the screw driver of FIG. 38A in an unlocked configuration; and FIG. 38E is a detail cross-sectional view of the distal end of the screw driver of FIG. 38D;

FIG. 39A is a perspective view of a base reamer; FIG. 39B is a side view of the base reamer of FIG. 39A; and FIG. 39C is a cross-sectional view of the base reamer of FIG. 39A;

FIG. 40A is a perspective view of a bases broach; FIG. 40B is a side view of the base broach of FIG. 40A; FIG. 40C is a cross-sectional view of the base broach of FIG. 40A.

FIG. 46A is a front perspective view of an inferior trial; FIG. 46B is a rear perspective view of the inferior trial of FIG. 46A; and FIG. 46C is a bottom view of the inferior trial of FIG. 46A;

DETAILED DESCRIPTION

The present invention advances the state of the art by providing systems and methods that can be used to replace natural vertebral facet joints with implantable artificial facet joint prostheses in a manner that provides a high degree of implant adjustability, simplicity, and ease of use.

In this application, "polyaxial" rotation is rotation that can occur about at least two axes that are not parallel to each other. "Lock-out" between two or more component parts refers to a state in which movement of any component part is prevented by frictional, compression, expansion, or other forces. A "taper-lock connector" refers to any locking mechanism that uses a taper to effect locking.

Figure 1:
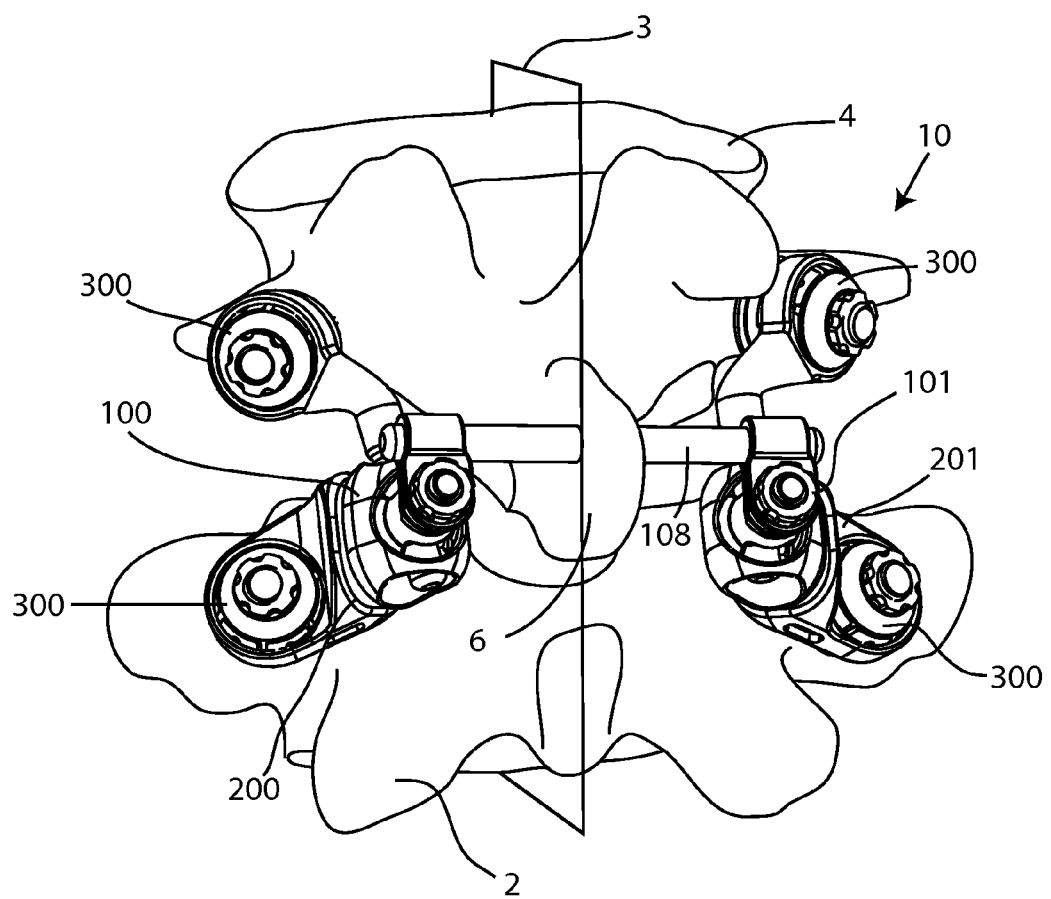
FIG. 1 is a perspective view of a portion of a spine with a bi-lateral facet joint replacement system implanted into two adjacent vertebrae.

Referring to FIG. 1, a perspective view depicts a portion of a spine including a first vertebra 2 and a second vertebra 4. Sagittal plane 3 is shown bisecting the vertebrae 2 and 4 into generally symmetric left and right portions. A system 10 of bi-lateral facet joint replacements joined by a crosslink rod 108 passing through a spinous process 6 of vertebra 4 is implanted in the vertebrae 2, 4. On the left side of the vertebrae 2, 4, an inferior facet joint implant 100 is secured to a fixation assembly 300 implanted in vertebra 4, and a superior facet joint implant 200 is secured to a fixation assembly 300 implanted in vertebra 2. On the right side of the vertebrae, an inferior facet joint implant 101 is secured to a fixation assembly 300 implanted in vertebra 4, and a superior facet joint implant 201 is secured to a fixation assembly 300 implanted in vertebra 2. It is appreciated that the facet joint replacement implants described herein may each be configured in a "right" or a "left" configuration to be implanted on the right or left lateral side of the vertebrae. However, only one (right or left) configuration will be described, and it is assumed that the other (right or left) configuration is a minor-image of the one described. It is also appreciated that the implants described herein may be implanted bi-laterally as in FIG. 1, or unilaterally, if desired.

Figure 2:
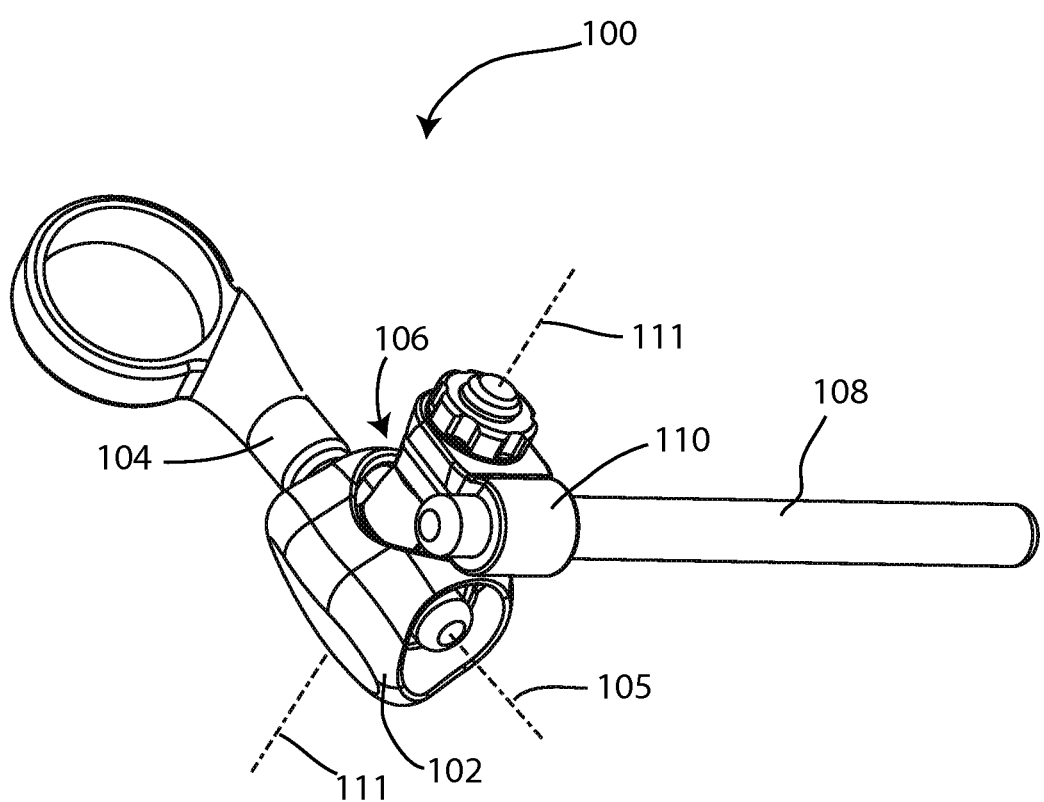
FIG. 2 is perspective view of an inferior facet joint implant coupled to a crosslink rod.

Referring to FIG. 2, a perspective view depicts polyaxially adjustable left inferior facet joint implant 100. Inferior facet joint implant 100 comprises an inferior articular body 102, an inferior strut 104, and an attachment mechanism 106 which adjustably secures the articular body to the inferior strut 104. The attachment mechanism 106 has an adjustable configuration in which the inferior articular body 102 can rotate relative to the inferior strut 104 about three orthogonal axes, and it has a locked configuration in which the inferior articular body 102 is rigidly secured to inferior strut 104. A crosslink rod 108 may optionally be secured to the implant 100 by a split clamp 110. The attachment mechanism 106 may be actuated to simultaneously lock the crosslink rod 108 in the split clamp 110 as the inferior articular body 102 is locked to the inferior strut 104. A clamp axis 111 extends longitudinally through the attachment mechanism. A strut axis 105 extends longitudinally along the inferior strut 104.

Figure 3:
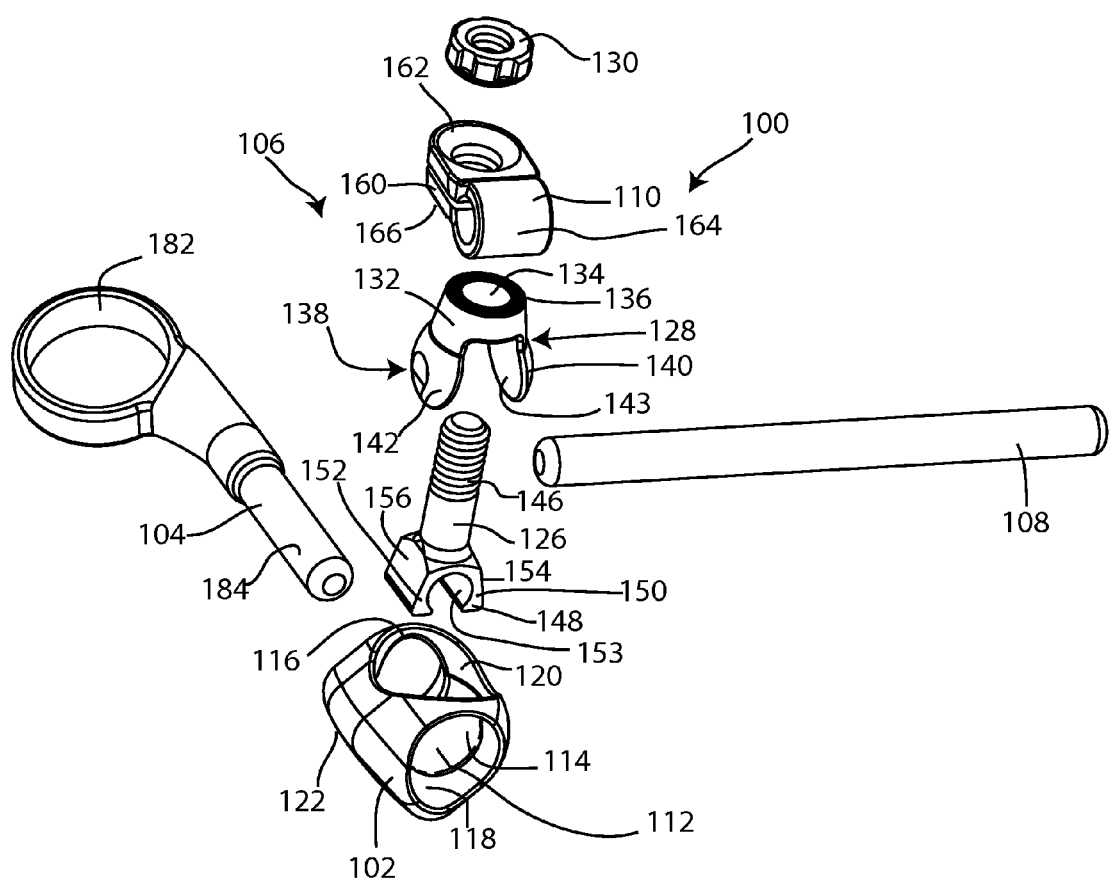
FIG. 3 is an exploded view of the inferior facet joint implant and crosslink rod of FIG. 2.

Referring to FIG. 3, an exploded perspective view illustrates the component parts which may comprise the left inferior facet joint implant 100. The inferior articular body 102 is shell-like and has a substantially concave interior cavity 112 which is defined by an interior wall 114. A first chamfered opening 116 and a second chamfered opening 118 in the inferior articular body 102 create a passageway through which a portion of the inferior strut may fit when the implant is assembled. An attachment post opening 120, which may also be chamfered, is situated orthogonal to the first and second chamfered openings 116, 118. The chamfered openings may provide additional range of motion between the inferior articular body and the inferior strut 104 as the inferior articular body 102 is polyaxially adjusted prior to locking down. An inferior articular surface 122 is located on the exterior of the inferior articular body 102, and is shaped to replace a natural inferior articular surface of a vertebra. Inferior facet implant 100 may be implanted in conjunction with a superior facet implant, wherein the inferior articular surface 122 articulates with an artificial superior facet articular surface. Alternately, inferior facet implant 100 may be implanted such that the inferior articular surface 122 articulates with a natural superior facet articular surface. In both cases, the articulation between inferior and superior articular surfaces preserves a level of natural spinal motion.

Figure 4:
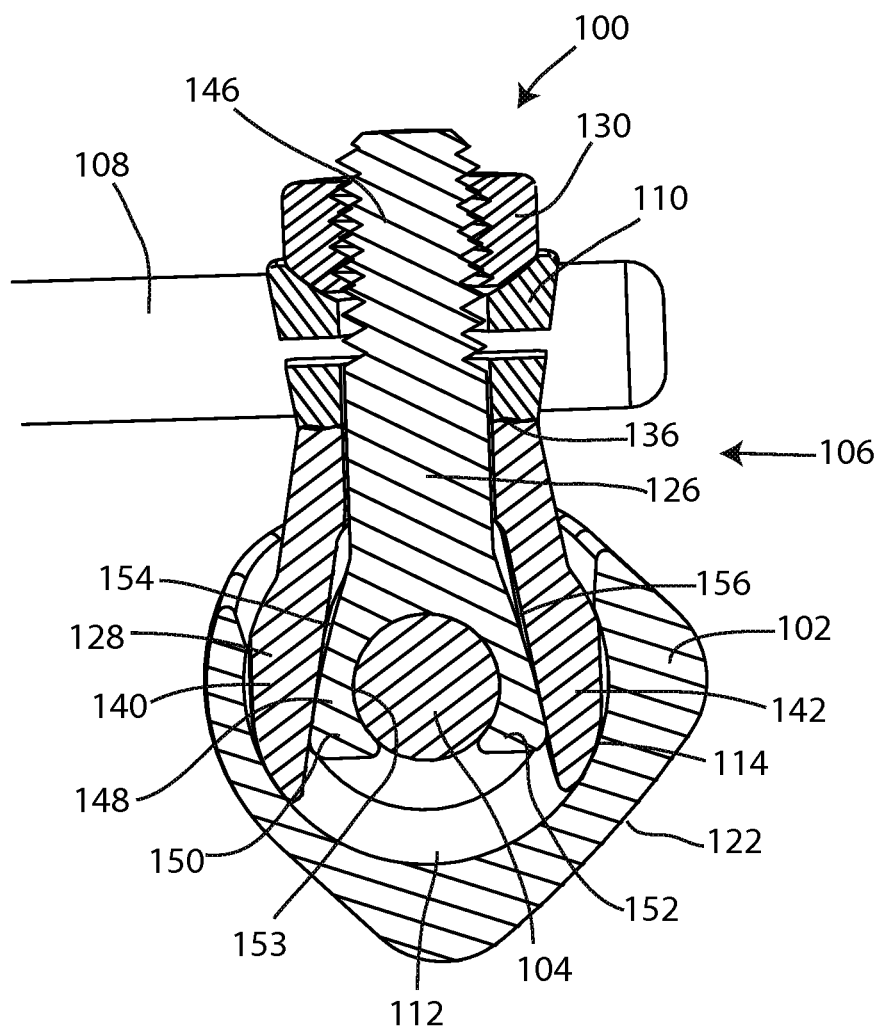
FIG. 4 is a partial cross-sectional view of an attachment mechanism of the facet joint implant of FIG. 2.

FIG. 4 displays the attachment mechanism 106 in a cross-sectional view. The attachment mechanism 106 is configured to provide polyaxial adjustability between the inferior articular surface 122 and the inferior strut 104. Once the desired orientation of the articular surface 122 relative to the inferior strut 104 is reached, the attachment mechanism 106 may be locked down, securing the articular surface to the inferior strut. Referring to FIGS. 3 and 4, the attachment mechanism comprises a locking member which is a threaded conical expander 126, an expandable member which is a split shell 128, the split clamp 110, and a nut 130. An alternative embodiment of an attachment mechanism may exclude the split clamp 110.

The split shell 128 has a circular neck portion 132 through which passes a bore 134. The bore opening is surrounded by a radial spline 136. Adjacent to the neck portion 132 is a spherical portion 138 which comprises two expandable lobes 140, 142. An interior surface 143 of the lobes 140, 142 may be tapered. The present embodiment of the invention includes two lobes, however it is appreciated that more lobes may be included, or other expandable portions, in other embodiments. The split shell 128 fits over the conical expander 126 such that a threaded post 146 of the conical expander 126 passes through the bore 134. An expansion portion 148 of the conical expander 126 is forked and has two opposing flanges 150, 152 which are shaped to fit around and grip the inferior strut 104. An inner wall 153 of the flanges is curved to fit around the inferior strut 104, and the outer walls 154, 156 are tapered.

The split ring clamp 110 comprises an inner ring 160, an outer ring 162 and a collar 164 which joins the inner and outer rings. The collar 164 is shaped to fit around and grip the crosslink rod 108. The split ring clamp 110 is configured such that when the inner and outer rings 160, 162 are compressed together, a diameter of the collar 164 decreases and the collar can tighten around and secure the crosslink rod. The surface of an exterior side of the inner ring 160 is a radial spline 166, which is shaped to engage with the radial spline 136 on the split shell 128.

When assembled, the split shell 128 fits over the conical expander 126, and the two parts fit within the inferior articular body 102 such that the interior cavity 112 houses the expansion portion 148 of the conical expander 126 nested inside the spherical portion 138 of the split shell 128. The conical expander 126, split shell 128 and inferior articular body 102 are oriented so that in general the flanges 150, 152 are adjacent to the lobes 140, 142, and the lobes are adjacent to the interior wall 114 of the interior cavity 112. A strut post 184 of the inferior strut 104 fits between the flanges 150, 152 of the conical expander 126.

The split ring clamp 110 fits over the threaded post 146 of the conical expander 126 so that the radial spline 166 of the split clamp meets the radial spline 136 of the split shell 128. The crosslink rod 108 extends through the collar 164 of the split clamp. The nut 130 is threaded onto the threaded post 146 of the conical expander 126.

Until the attachment mechanism 106 is locked down by actuating the nut 130, the implant is adjustable in multiple ways. The crosslink rod 108 has relative angular freedom of motion about the clamp axis 111 and the inferior strut axis 105. The position of the crosslink rod 108 relative to the split clamp 110 may be adjusted such that a relatively longer or shorter length of the crosslink rod 108 extends through the clamp. This provides an opportunity to select the best fit to the patient's anatomy and the specific vertebral level being treated. Similarly, the position of the inferior strut 104 may be adjusted relative to the inferior articular body 102 such that a relatively longer or shorter length of the inferior strut 104 extends through the flanges 150, 152 of the conical expander 126. Also, the inferior strut 104 has relative angular freedom of motion about the clamp axis 111. The inferior articular body 102 may be polyaxially rotated about the conical expander 126 and the split shell 128. The adjustments provide relative rotation between the inferior articulation surface 122 and the inferior strut 104 about three orthogonal axes. In addition, prior to lockdown, relative translation between the inferior strut 104, the inferior articulation surface 122, and the crosslink rod 108 is permitted.

The attachment mechanism 106 is locked down by actuating, or turning the nut 130. As the nut 130 is turned and its threads engage the threaded post 146, the conical expander 126 is urged "upward" through the nut 130, while the outer ring 162 of the split clamp 110 is urged "downward" toward the inner ring 160. As the conical expander 126 moves, the flanges 150, 152 push against the lobes 140, 142 of the split shell 128, and in turn the lobes expand and push against the interior wall 114 of the interior cavity 112. Simultaneously, the flanges 150, 152 are compressed around the inferior strut 104. Similarly, the collar 164 of the split clamp 110 is compressed around the crosslink rod 108 as the inner 160 and outer 162 rings of the clamp are urged together. The nut 130 may be actuated until the resulting internal compression prevents any further motion, and the mechanism 106 is locked down.

The inferior implant 100 may be delivered in an assembled, but not locked down, configuration. The crosslink rod 108 may be included in the assembly, provided separately, or excluded. The inferior implant 100 may be delivered in combination with a superior implant, in which a clip or other temporary fastener holds the inferior articular surface to a superior articular surface of the superior implant.

Figure 5:
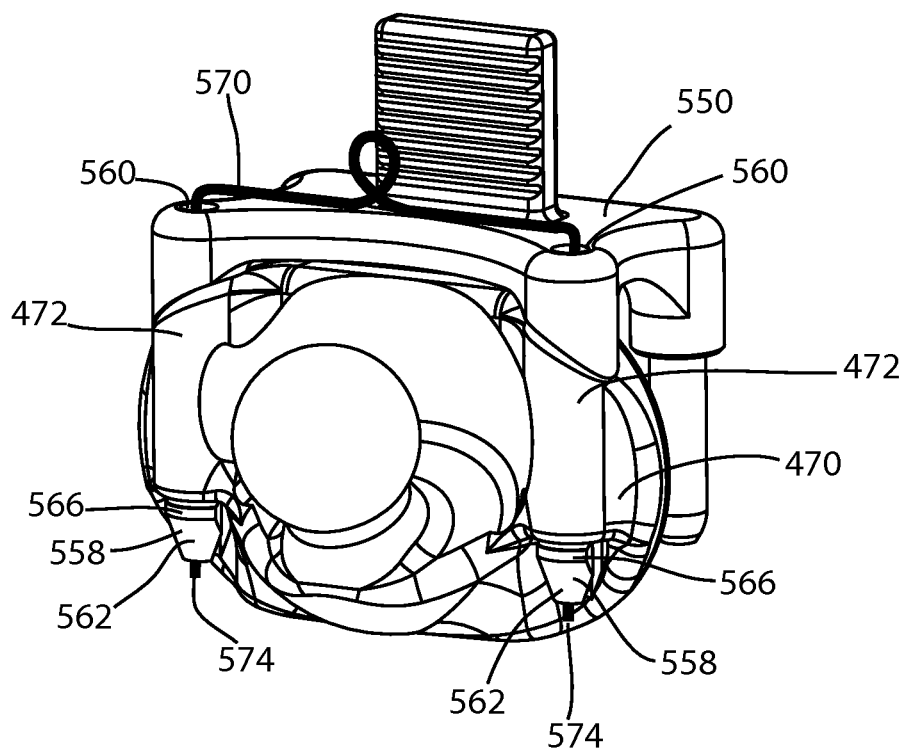
FIG. 5 is a perspective view of an inferior implant body coupled to a clip.

FIG. 5 presents an alternative embodiment of an inferior articular body 470, which may be available pre-packaged temporarily attached to a coupler, or clip 550 with a plug 570. Alternatively, a gripping tool (not shown) may be used to hold the inferior articular body 470. It can be appreciated that any of the various embodiments of the inferior articular body disclosed may be adapted for use with the clip 550 and plug 570. The inferior articular body 470 may be assembled to an attachment mechanism and inferior strut (not shown) in a manner similar to that described above with regard to other inferior implant embodiments.

Figure 6:
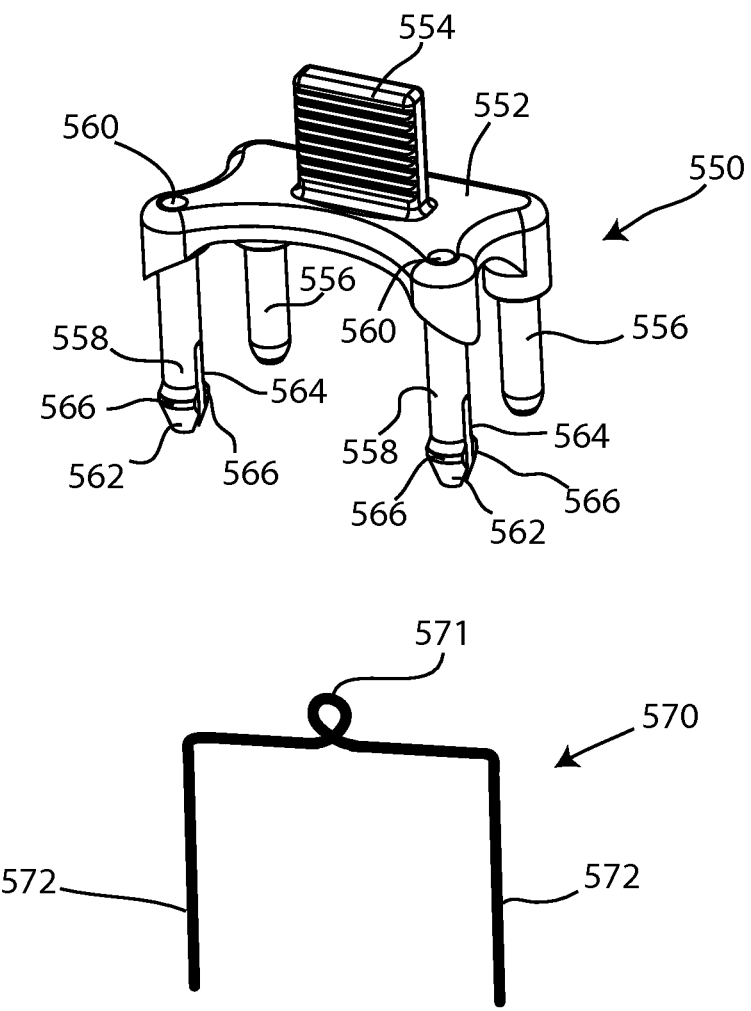
FIG. 6 is a perspective view of the clip of FIG. 5 and a plug.

FIG. 6 is a perspective view of the clip 550 and the plug 570. Clip 550 comprises a clip body 552, a handle 554, and two pairs of pins which extend substantially orthogonally from the body: a pair of superior pins 556 and a pair of inferior pins 558. The inferior pins 558 are cannulated, each having a bore 560 which extends the length of the pin 558, from the body 552 to a split end 562. Each split end 562 includes at least one slot 564 which extends partially along the length of the pin 558, and a protruding flange 566. The inferior pins 558 are shaped to receive an inferior facet joint implant, and the superior pins 556 are shaped to receive a superior facet joint implant.

The plug 570 comprises a handle 571 and two prongs 572 which are sized to extend through the bores 560 of the inferior pins 558 of the clip 550. When the plug 570 is inserted fully into the inferior pins 558, the prongs 572 urge apart the split ends 562 from a narrow first configuration to an expanded second configuration in which the slots 564 are widened, and the flanges 566 on each pin are farther apart. When the plug 570 is removed, the split ends 562 return from the expanded second configuration to the narrow first configuration.

Returning to FIG. 5, the inferior articular body 470 is shown coupled with the clip 550 and the plug 570. The inferior pins 558 extend through tubes 472 formed on the inferior implant 470, such that the split ends 562 and flanges 566 emerge outside of the tubes. The plug 570 is fully inserted through the clip bores 560, and therefore the prongs 574 keep the split ends in the expanded second configuration. In the expanded second configuration, the widened flanges 566 cause the diameter of the split ends 562 to be greater than the diameter of the tubes 472, preventing the clip 550 from being withdrawn from the inferior articular body 470. Thus held by the clip 550, the inferior articular body 470, with or without other attached components such as an inferior strut, may be clipped to a superior implant.

Figure 23:
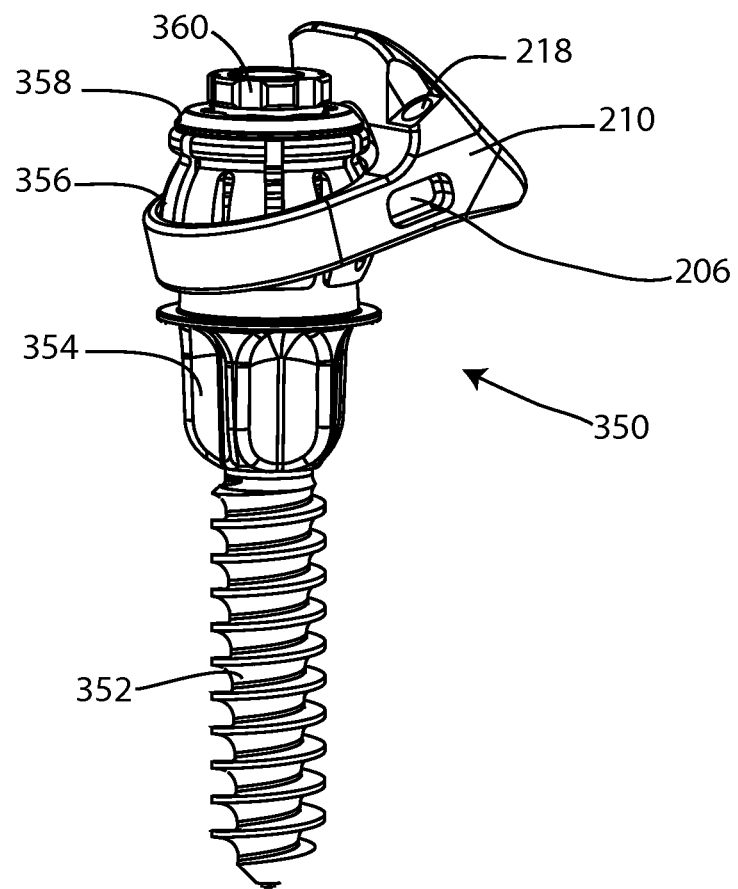
FIG. 23 is a perspective view of an alternate fixation assembly secured to an alternate embodiment of a superior facet joint implant.

Referring to FIG. 7A, an alternate embodiment of a coupling clip is shown. Clip 1200 is of one-piece construction, and is shaped to couple an inferior facet replacement implant such as inferior implant 100 (FIG. 1) with a superior facet replacement implant such as superior implant 210 (FIG. 23). Clip 1200 may retain the implants such that the inferior and superior articulation surfaces are held at a desired relative position. A portion of the clip 1200 is deformable and may be flexed to detach the clip from at least one of the implants.

Clip 1200 comprises a first end 1202 and a second end 1204, and the ends are linked by a connecting portion 1206. First end 1202 comprises a rigid shoulder 1208, and at opposing ends of the rigid shoulder 1208 are a tab 1210 and a post 1212. The tab 1210 and post 1212 are also rigid, and are shaped to couple with and align the inferior and superior implants. A recess 1220 is located on the shoulder 1208. Similarly, second end 1204 comprises a rigid shoulder 1214, tab 1216, post 1218, and recess 1222. Tabs 1210, 1216 are shaped to receive an inferior facet joint implant, and posts 1212, 1218 are shaped to receive a superior facet joint implant. Connecting portion 1206 is deformable, and when it is flexed, first end 1202 rotates about the axis of post 1212, and second end 1204 rotates about the axis of post 1218, such that tabs 1210, 1216 are urged apart.

FIG. 7B is a perspective view of clip 1200 coupled to an inferior facet joint implant 1230. Inferior facet joint implant 1230 is similar to inferior implant 100 seen in FIG. 2, but includes an alternative inferior articular body 1232. Inferior facet joint implant 1230 comprises inferior articular body 1232, conical expander 126, split shell 128, split clamp 110, top nut 130, inferior strut 104, and split sphere 356 which may be captured in the ring 182 of the inferior strut. Inferior articular body 1232 comprises an inferior articular surface 1234 and a pair of slots 1236 which are shaped to receive the tabs 1210, 1216 of the clip 1200. Inferior facet joint implant 1230 may be delivered coupled to clip 1200. Packaging (not shown) may be shaped to prevent connecting portion 1206 from flexing, and to keep posts 1212, 1218 in a fixed position.

Figure 8A:
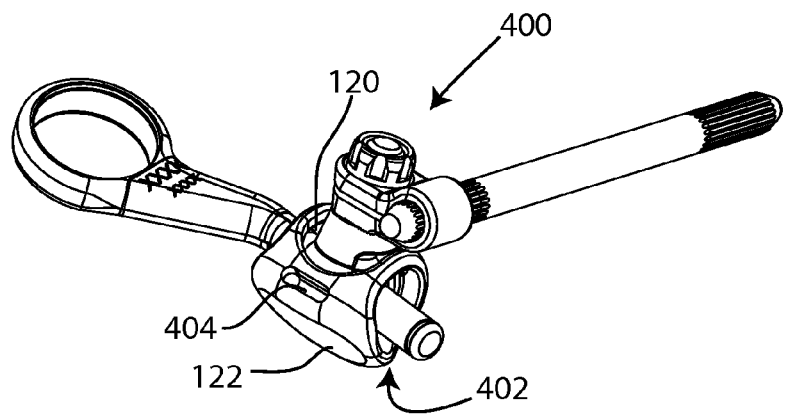
FIG. 8A is a perspective view of an alternate embodiment of an inferior facet joint implant coupled to a crosslink rod.
Figure 8B:
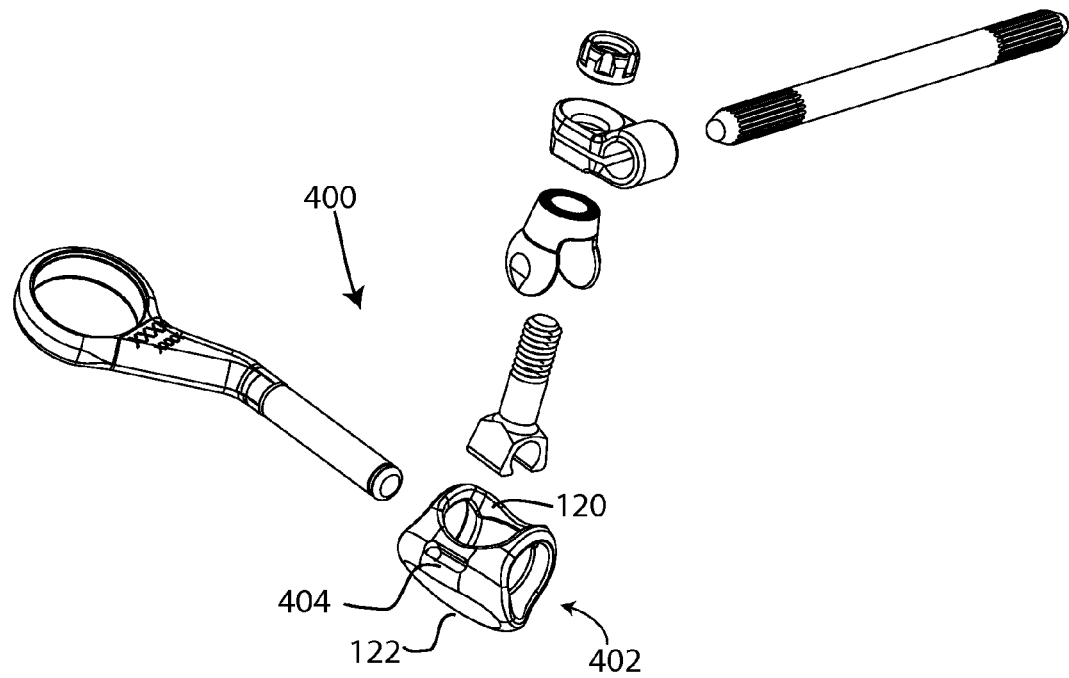
FIG. 8B is an exploded view of the inferior facet joint implant and crosslink rod of FIG. 8A.
Figure 9A:
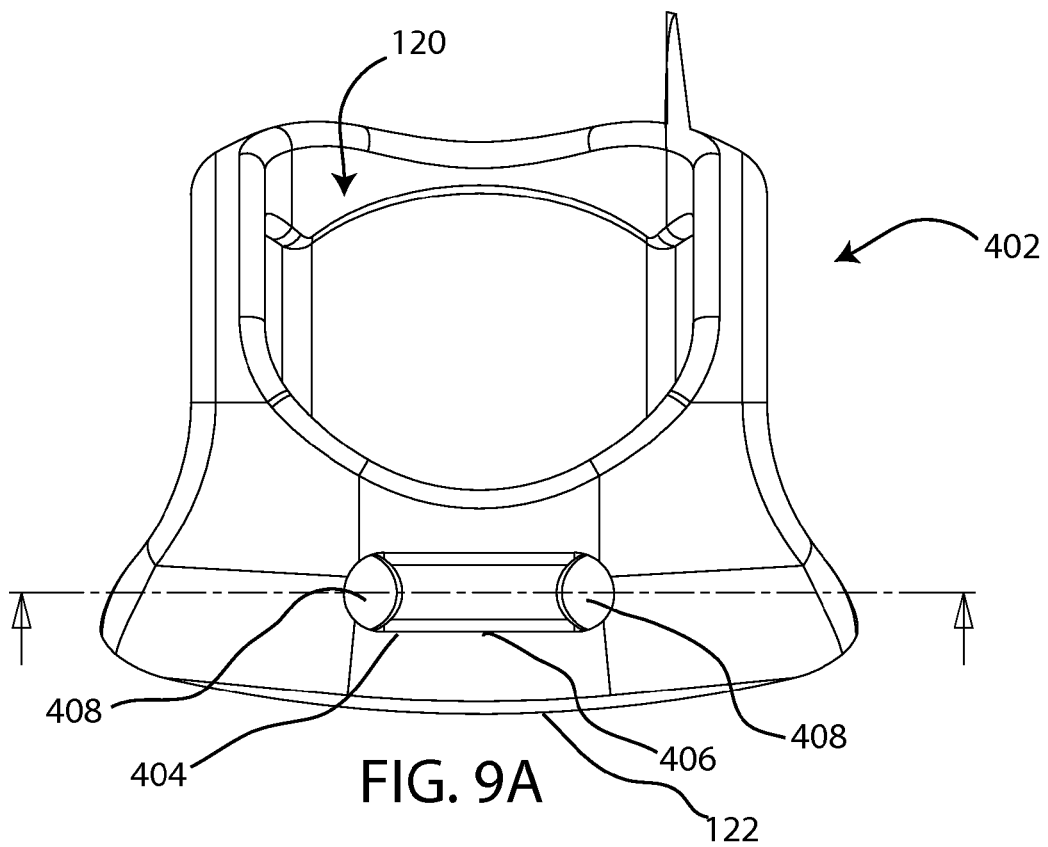
FIG. 9A is a plan view of an inferior articular body of the inferior facet joint implant of FIG. 8.
Figure 9B:
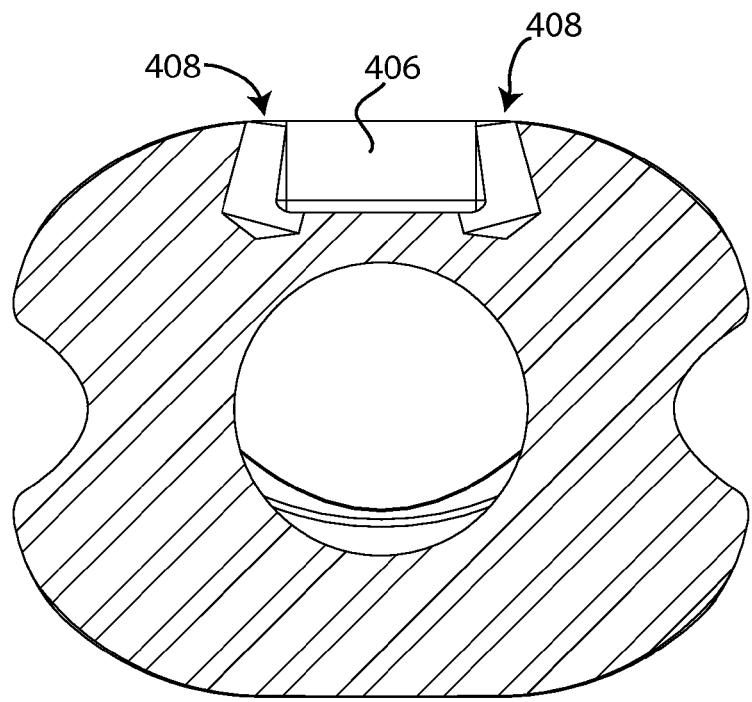
FIG. 9B is a cross-sectional view of the inferior articular body of FIG. 9A.

FIGS. 8 and 9 present an alternative embodiment of an inferior implant 400 with an alternative embodiment of an inferior articular body 402. This embodiment may differ from inferior articular body 102 in that it comprises a gripping feature 404 between the attachment post opening 120 and the inferior articular surface 122. The gripping feature 404 comprises an elongated slot 406 with an angled hole 408 cut into each end of the slot 406 (FIG. 9). The two holes 408 may diverge so that the gripping feature 404 is undercut at each end of the slot 406. Alternatively, the gripping feature 404 may comprise another undercut configuration, such as a dovetail or a keyseat.

Figure 10A:
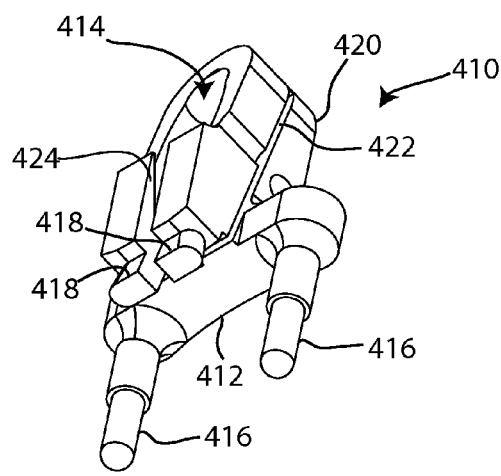
FIG. 10A is a perspective view of an alternate embodiment of a clip.
Figure 10B:
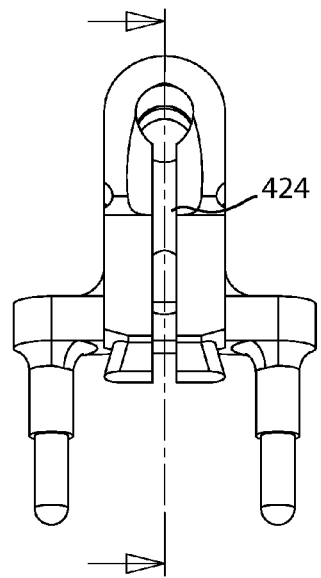
FIG. 10B is a front view of the clip of FIG. 10A.
Figure 10C:
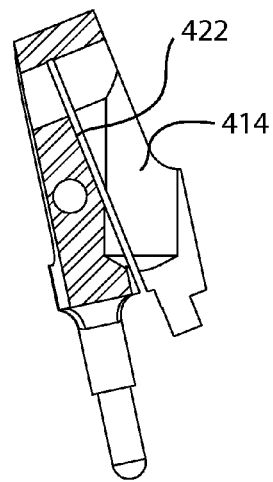
FIG. 10C is a cross-sectional view of the clip of FIG. 10A.

Referring to FIG. 10, another alternate embodiment of a coupling clip is shown. Clip 410 comprises a clip body 412, an instrument socket 414, a tab 420, a pair of pins 416, and a pair of prongs 418. The pins 416 are shaped to engage a superior facet joint implant and the prongs 418 are shaped to engage an inferior facet joint implant. The pins 416 may be cylindrical and they may or may not have a constant diameter over their entire length. The prongs 418 may flare away from each other or present a dovetail or flanged configuration corresponding to the configuration of the gripping feature on the inferior facet joint implant. The pins 416 and prongs 418 project orthogonally from a distal side of the clip body 412, and the tab 420 projects orthogonally from a proximal side of the clip body 412. The socket 414 is located between the prongs 418 and may be oriented at an angle to the clip body 412. A first slot 422 cuts through the clip body 412 so that the pins 416 are disposed on one side of the slot 422 and the prongs 418 are disposed on the other side. The slot 422 extends through a portion of the tab 420 adjacent to the clip body 412. The slot 422 enables the clip 410 to flex so that the prongs 418 can move toward or away from the pins 416. A second slot 424 is oriented perpendicular to the first slot 422, and cuts through the portion of the tab 420 that bears the prongs 418 and the socket 414, so that the slot 424 is substantially centered with respect to the prongs 418 and the socket 414. The slot 424 enables the clip 410 to flex so that the prongs 418 can move toward or away from each other and the socket 414 can increase or decrease in width.

Figure 11:
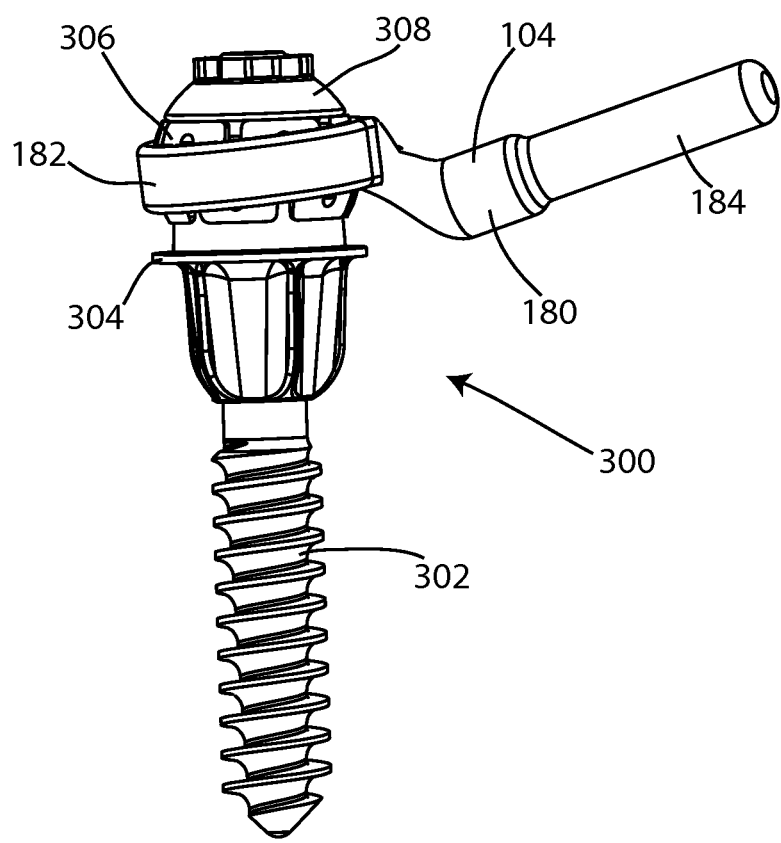
FIG. 11 is a perspective view of a fixation assembly secured to an inferior strut.

Referring to FIG. 11, inferior strut 104 is shown coupled to fixation assembly 300, which may also be termed an attachment mechanism. The inferior strut 104 is generally elongated in configuration, with a central portion 180, a first end which is a ring 182, and a second end which is a strut post 184.

The ring 182 may be a generally circular feature with a center point and opposed end faces which are substantially planar and parallel. The ring 182 may be set at an angle relative to the central portion 180 and the strut post 184. The strut post 184 may be a generally cylindrical feature with a longitudinal center axis. The strut post 184 may be at an angle relative to the central portion 180 and the ring 182; also the central portion 180 may be straight, bent or curved.

A kit of inferior implants may be provided, wherein each inferior implant in the kit is a different size or shape so that a particular inferior implant may be selected for implantation at a certain operative site. U.S. patent application Ser. No. 12/240,320, which is incorporated herein by reference in its entirety, describes such a kit of inferior implants in terms of physical dimensions which may vary independently among the various inferior implants in the kit.

Some of the physical dimensions that may change between the different sizes of inferior implants are an X2 offset, a Y2 offset, and a Z2 offset. These dimension may be used to describe the location of a center point C1 of the inferior articulation surface with respect to local vertebral landmarks, such as a pedicle saddle point or pedicle axis, or standard anatomical reference planes, such as the sagittal plane 3. It can be appreciated that the same dimensions may be measured on one or more intact natural vertebrae in order to develop inferior implants that accurately fit a majority of the patient population.

The pedicle axis may be the same as the longitudinal axis of fixation member 302, or any other fixation member disclosed herein, after implantation into a pedicle. The pedicle axis may also be the axis passing along the center of a substantially tubular midportion of the pedicle, independent of any fixation member. The pedicle saddle point is frequently equivalent to the entry point of a fixation member into the pedicle; it may also be defined as the intersection of the pedicle axis and the posterior bone surface lateral to the superior articular process of a vertebra.

Exemplary values for the foregoing dimensions will be provided below. Although the exemplary values relate primarily to L5 superior and L4 inferior, they may apply to other combinations of vertebrae in the lower back and/or the sacrum. One or more of these variables may change between the different inferior implant sizes.

For a particular inferior articular surface and its immediately adjacent pedicle, the center point C1 of the inferior articulation surface is displaced from the saddle point S2 by an X2 offset, a Y2 offset, and a Z2 offset. The direction of the Y2 offset is parallel to the pedicle axis. The direction of the Y2 offset is generally, but not precisely, anterior to posterior. The direction of the X2 offsets is perpendicular to the Y2 offset. The direction of the X2 offset is generally, but not precisely, lateral to medial with respect to the central axis of the patient's spine. The direction of the Z2 offset is perpendicular to the Y2 offset and the X2 offset. The direction of the Z2 offset is generally cephalad to caudal.

The X2 offset for the inferior implant can range from 0 mm to 20 mm. However, for the majority of patients, the X2 offset will range from 2 mm to 16 mm. Therefore a family of inferior implants can be provided with the X2 offset varying in increments of 2 mm. Thus, sets of inferior implants would be provided with X2 offset at 2 mm, 4 mm, 6 mm, 8 mm, 10 mm, 12 mm, 14 mm, and 16 mm to cover the statistical range for the majority of the population of patients needing inferior implants.

The Y2 offset for the inferior implant can range from −15 mm to 5 mm. However, for the majority of patients, the Y2 offset will range from −12 mm to 4 mm. Therefore a family of inferior implants can be provided with the Y2 offset varying in increments of 2 mm. Thus, sets of inferior implants would be provided with Y2 offset at −12 mm, −10 mm, −8 mm, −6 mm, −4 mm, −2 mm, 0 mm, 2 mm, and 4 mm to cover the statistical range for the majority of the population of patients needing inferior implants.

The Z2 offset for the inferior implant can range from 20 mm to 40 mm. However, for the majority of patients, the Z2 offset will range from 25 mm to 31 mm. Therefore a family of inferior implants can be provided with the Z2 offset varying in increments of 1 mm. Thus, sets of inferior implants would be provided with Z2 offset at 25 mm, 26 mm, 27 mm, 28 mm, 29 mm, 30 mm, and 31 mm to cover the statistical range for the majority of the population of patients needing inferior implants.

The parameters of the inferior implant may include at least two dimensions that vary among the members of the kit independently of each other. Dimensions that vary independently of each other need not change according to any established relationship between the dimensions, but instead, one may change while the other remains the same between any two prostheses of the kit. More specifically, the kit of inferior implants may comprise a plurality of inferior struts of different sizes and shapes, each of which may be provided pre-assembled with an inferior articular body, an attachment mechanism, and optionally a split sphere. As set forth previously, the relative orientation of the ring, central portion, and strut post of the inferior strut may vary. In one embodiment, the tip of the strut post may be offset from the center point of the ring by one or more of the X2 offset, the Y2 offset, and the Z2 offset.

Fixation assembly 300 is configured to be implanted in a pedicle of a vertebra, and to be coupled to inferior implant 100 or another implant. The fixation assembly 300 provides for polyaxial adjustment of the implant with respect to the fixation assembly 300, and comprises a fixation member 302, a tapered base 304, a split sphere 306, and a top nut 308.

Figure 12:
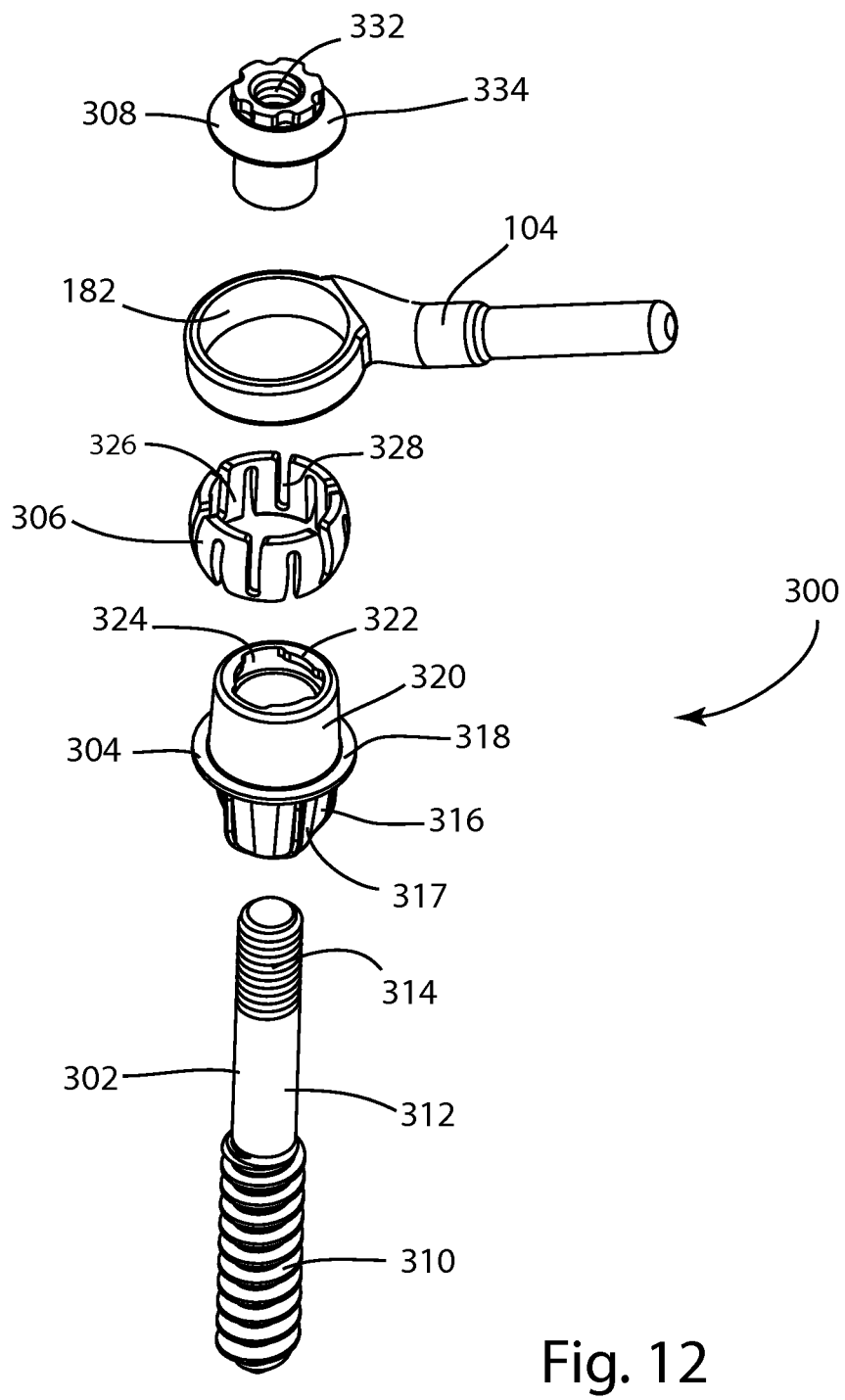
FIG. 12 is an exploded view of the fixation assembly and inferior strut of FIG. 11.

FIG. 12 is an exploded view of the inferior strut 104 and the fixation assembly 300. The fixation member 302, which may be a pedicle screw, has a distal threaded bone engaging portion 310, a shaft 312, and a proximal threaded attachment portion 314. The tapered base 304 is cannulated throughout, and has an inset bone-engaging portion 316, a flange 318, and a tapered portion 320. The inset portion 316 may be tapered to provide compression to the surrounding bone, and may have a plurality of fins 317 which prevent rotation of the base 304 in the bone. In alternate embodiments of the invention, the inset portion 316 may include teeth, studs, fins, or combinations thereof, or other anti-rotation features, or no anti-rotation features. The tapered portion 320 may serve as an attachment portion, configured for attachment of an implant. At an open end of the tapered portion 320, a tool engagement rim 322 includes a plurality of notches 324. Other embodiments of the base may include threads or other features instead of notches configured to engage a tool. An inner wall 326 of the split sphere 306 is sized to fit over the tapered portion 320 of the base 304, and includes a plurality of slits 328 which allow the sphere to be expandable. The inner wall 326 of the split sphere 306 may also be tapered. The top nut 308 has a threaded bore 332 and a flange 334 which encircles the nut 308.

The fixation assembly 300 may be assembled from the components described above during implantation, or it may be delivered in a partially assembled state. For example, the split sphere 306 may be provided captive within the ring 182.

Prior to locking down the fixation assembly 300, the ring 182 may be polyaxially adjusted around the split sphere 306 so that the inferior strut 104 attains a desired orientation. To lock down the desired orientation, a compression lockout tool (not shown) engages the notches 324 of the tool engagement rim 322 on the base 304. Other embodiments of the base may include a threaded tool engagement interface, configured to engage with a threaded lockout tool. The lockout tool provides compression on the split sphere 306, urging it farther onto the tapered portion 320 toward the flange 318. As the split sphere 306 moves down the tapered portion 320, it expands to bind within the ring 182 of the inferior strut 104. Once all motion between the tapered portion 320, split sphere 306 and ring 182 is locked out, the lockout tool is removed. The top nut 308 is threaded onto the threaded attachment portion 314 of the fixation member 302, to retain the base 304, sphere 306 and inferior strut 104 on the fixation member 302, and to further secure the inset portion 316 of the base 304 in the vertebra. Optionally, the base 304, split sphere 306, and inferior strut 104 may be assembled and locked out independently of the fixation member 302, then dropped onto the fixation member 302 and retained with the top nut 308. The inferior articular body 102 and the attachment mechanism 106 may be secured to the inferior strut 104 before or after the inferior strut 104 is locked into position with the base 304 and split sphere 306.

FIGS. 13-20 depict alternative embodiments of implant base members. Each base member comprises a tapered portion shaped to mate with an expandable member, or collet that is tapered inside and substantially spherical outside, such as split sphere 306 or 356. The tapered surface facilitates a taper lock between the base and the collet (and inferior or superior implant), thereby locking out adjustability between the implant and the base as described previously with regard to FIG. 12. Below the tapered portion may be a flange to prevent subsidence and provide a stable surface against the adjacent bone, and to provide additional surface area for bone ingrowth. In addition, a generally cylindrical bone-engaging portion of the base extends down into the pedicle of the vertebra. The bone-engaging portion, which may also be tapered forming a conical shape, may have any number of fins or other features (3-7 in preferred embodiments) which may project into the surrounding bone to resist rotation forces. Each base has a lumen extending throughout both the tapered portion and bone-engaging portion to fit over a pedicle screw or other fixation member. The lumen may be cylindrical or may include a non-cylindrical indexing surface with one or more flat sections, shaped to receive a hexagonal driver or a driver of another shape, including triangular, square, pentagonal, or octagonal, among others. Additionally, each base may have engagement features such as notches or threads which allow a tool or gripping instrument to engage with and hold the base during implantation and lockout procedures. Implantation of each base may follow the same procedures as set forth previously for base 304. Bases with fins or other protruding anti-rotation features may require additional bone preparation steps, such as broaching, to adequately prepare the bone for the fins.

Each base member embodiment may differ in the number of fins that radiate outward from the center axis to resist rotation. The length, width, and taper of fins or other anti-rotation features may vary. Other embodiments of the implant base may have studs, pegs, or posts instead of fins, or may have slots in the bone-engaging portion that extend downward into the pedicle. Also, the flange and/or bone-engaging portion may be coated with bone in-growth material, such as porous material or hydroxyapatite, among others. Additional embodiments may incorporate sawtooth fins to allow for self-guiding and/or self-cutting, therefore eliminating a separate preparation step. It is appreciated that the bases disclosed herein may be used with the fixation assemblies also disclosed herein, or in other orthopedic applications employing bone-engaging fixation members.

The combination of a base member such as those disclosed herein with a fixation member such as a pedicle screw may provide several advantages when compared to a pedicle screw alone. The contact area between the pedicle and the fixation assembly over which bending loads are distributed will be increased, since the bone-engaging portion of each base provides a greater surface to bone contact area than a pedicle screw alone. According to Wolff's Law, a bone in a healthy person or animal will adapt to the loads under which it is placed. If loading on a particular bone increases, the bone will remodel itself over time to become stronger to resist that sort of loading. Increasing the bone contact area through the use of a base member may therefore result in strengthening of a larger portion of the bone around the implant fixation assembly. Additionally, less load may be placed on the pedicle screw, which may result in decreased likelihood of loosening of the screw over time.

Figure 13A:
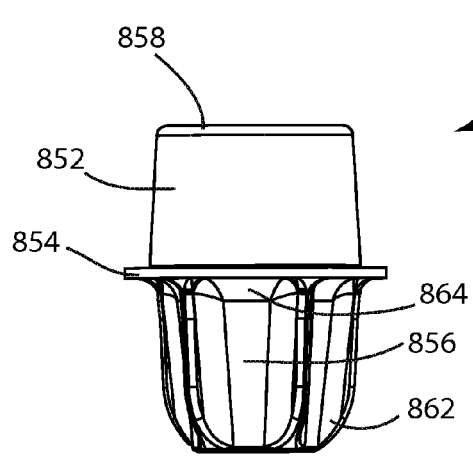
FIG. 13A is a lateral view of a fixation assembly base member.
Figure 13B:
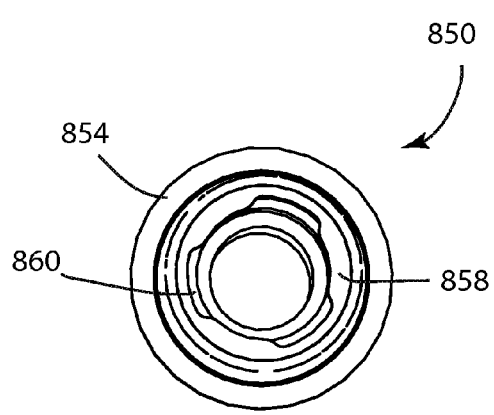
FIG. 13B is a posterior view of the fixation assembly base member of FIG. 13A.
Figure 13C:
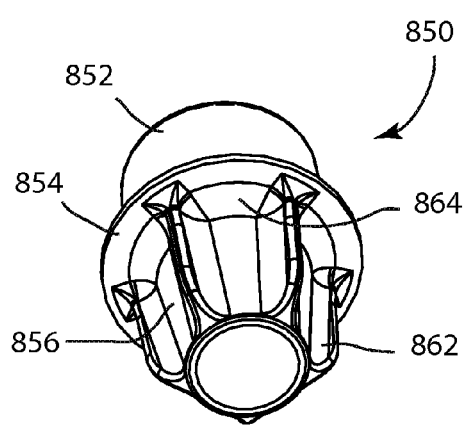
FIG. 13C is an anterior perspective view of the fixation assembly base member of FIG. 13A.
Figure 13D:
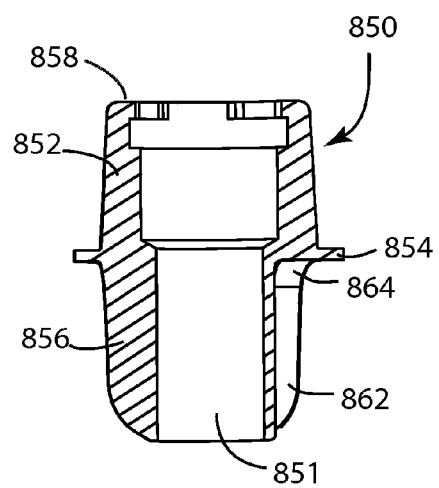
FIG. 13D is a cross-sectional view of the fixation assembly base member of FIG. 13A.

FIG. 13A is a side view of a facet implant base member 850; FIG. 13B is an end view of the base 850; FIG. 13C is a perspective view of the base 850; and FIG. 13D is cross-sectional view of the base 850. Base 850 comprises a tapered portion 852 separated from a bone-engaging portion 856 by a flange 854. A lumen 851 extends the length of the base, the lumen 851 is shaped to receive a fixation member such as 302, or a pedicle screw, among others. A first end 858 includes several notches 860 which are engagement features shaped to mate with a placement and/or lockout tool. In this embodiment, five evenly spaced fins 862 project outward from the bone-engaging portion 856. The fins 862 may prevent rotation of the base 850 in the pedicle. A fillet 864 is located between each fin and the adjacent fin and provides a transition between the flange 854 and the bone-engaging portion 856. In other embodiments of the base, there may be fewer or more fins, and the fins may be evenly or unevenly spaced, or paired, or grouped. The morphology of the fins may vary; some fins may have sharp, well-defined edges while others may have more rounded edges. The fins may taper between the flange and the distal end of the bone-engaging portion. Similarly, the sizes of the fillets 864 may vary; a larger fillet will provide a less sharp, more continuous transition between fins. Providing more gradual, less acute transitions between features on the base may prevent the occurrence of low-load areas where less bone in-growth might occur.

Figure 14A:
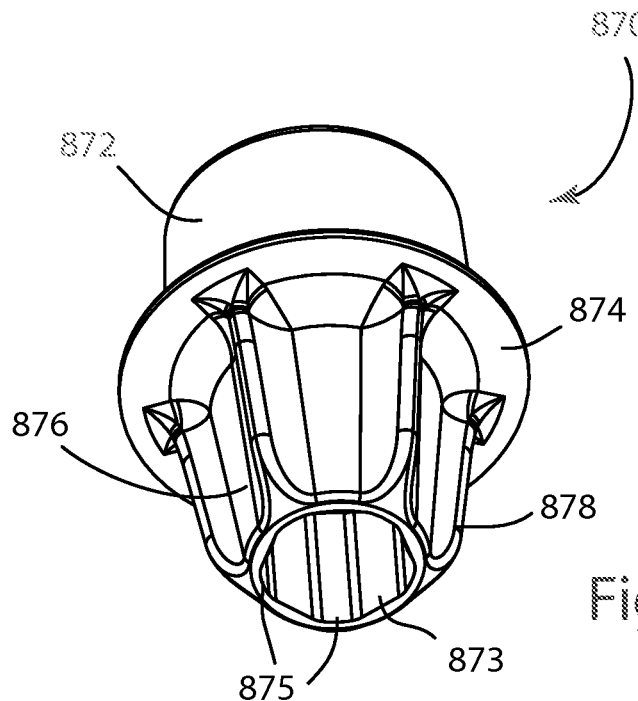
FIG. 14A is a lateral perspective view of an alternate fixation assembly base member.
Figure 14B:
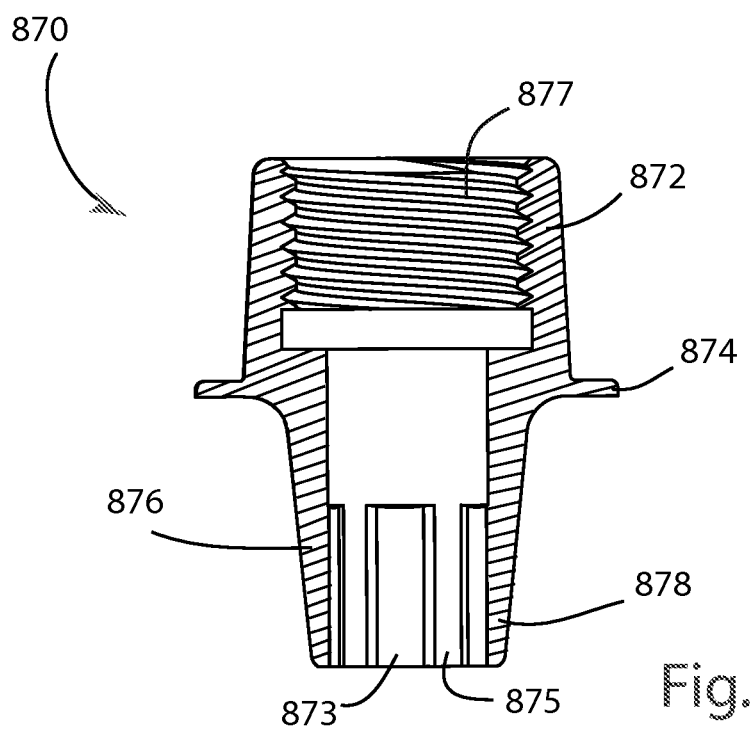
FIG. 14B is a cross-sectional view of the fixation assembly base member of FIG. 14A.

Referring to FIG. 14, an alternative embodiment of an implant base member is shown. Implant base 870 has a tapered portion 872, a flange 874 and a bone-engaging portion 876. A plurality of fins 878 extend outward from the bone-engaging portion 876. The central lumen 871 includes flat sections 873 interspersed with curved sections 875, allowing for engagement with a tool such as a pentagonal driver (not shown). The flat sections 873 may provide a practitioner with immediate orientation of the fins 878 relative to the bone screw with which the base is coupled, as well as to broached slots in the bone. The curved sections 875 have a diameter outside the dimensions of the flat sections 873. The tapered portion includes threads 877 which may extend throughout the tapered portion as shown or, in other embodiments, may extend only partially through the tapered portion. The threads 877 are configured to engage with a placement and/or lockout tool, which may provide force to effect a taper lock between an implant and the base, as set forth previously.

Figure 15:
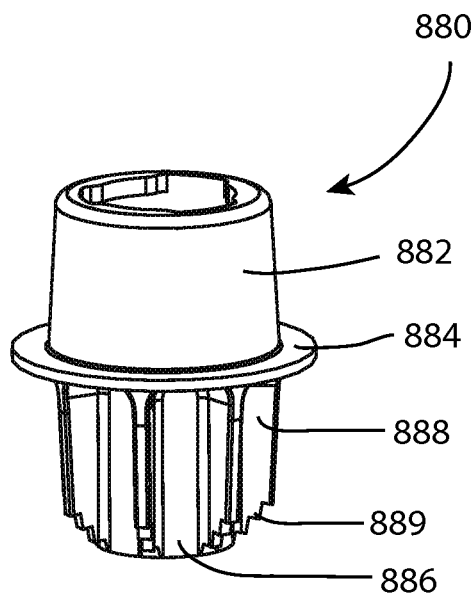
FIG. 15 is a lateral perspective view of an alternate fixation assembly base member.

Referring to FIG. 15, another alternative embodiment of an implant base member is shown. Implant base 880 has a tapered portion 882, a flange 884 and a bone-engaging portion 886. A plurality of fins 888 extend outward from the bone-engaging portion 886. Each fin 888 is serrated with several teeth 889, which may provide self-broaching of the bone during implantation of the base.

Figure 16:
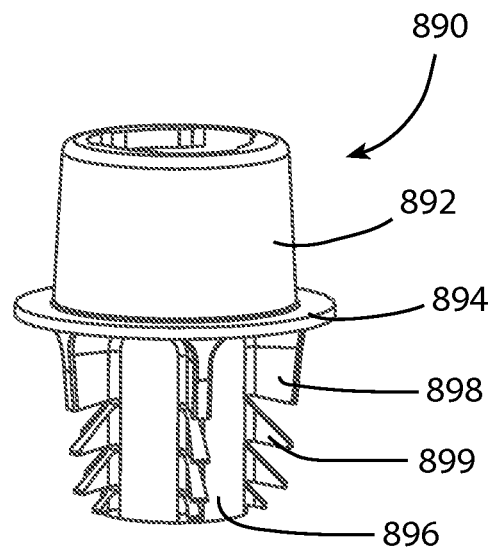
FIG. 16 is a lateral perspective view of an alternate fixation assembly base member.

Referring to FIG. 16, yet another alternative embodiment of an implant base member is shown. Implant base 890 has a tapered portion 892, a flange 894 and a bone-engaging portion 896. A plurality of jagged fins 898 extend outward from the bone-engaging portion 896. Each fin 898 comprises a series of teeth 899 which may be graduated in size. Similar to implant base 880, the teeth may provide self-broaching during implantation, and may reduce the bone preparation needed prior to implantation.

Figure 17:
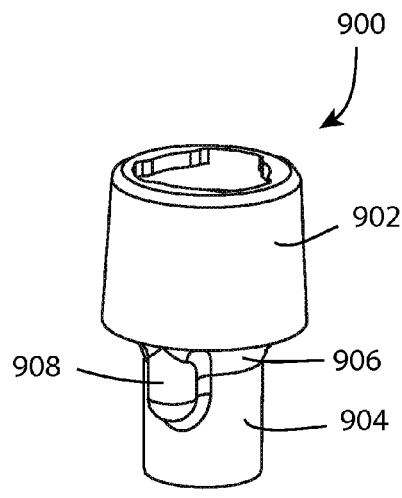
FIG. 17 is a lateral perspective view of an alternate fixation assembly base member.

Referring to FIG. 17, another alternative embodiment of an implant base member is shown. Implant base 900 comprises a tapered portion 902 and a bone-engaging portion 904. A curved transitional area 906 connects the tapered portion and the bone-engaging portion. The transitional area serves a similar function as the flange in other embodiments, preventing subsidence of the implant. Two pegs 908, which may prevent rotation of the base, protrude outward from the bone-engaging portion 904.

Figure 18:
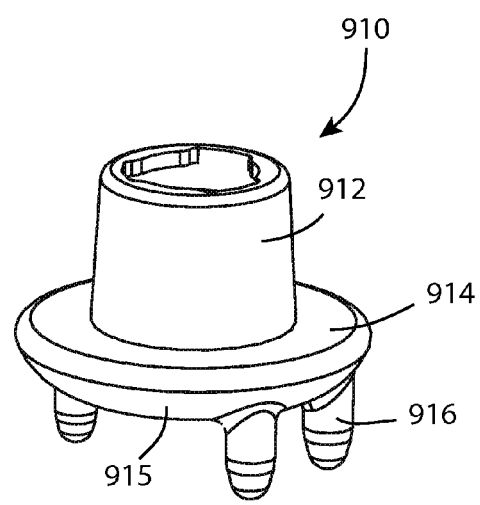
FIG. 18 is a lateral perspective view of an alternate fixation assembly base member.

Referring to FIG. 18, another alternative embodiment of an implant base member is shown. Implant base 910 comprises a tapered portion 912 and a bone-engaging portion 914. In this embodiment, the dish-shaped bone-engaging portion 914 has a greater diameter than the tapered portion 912. Bone-engaging portion 914 has a spherical bone-contacting surface 915. The configuration of the bone-engaging portion 914 may prevent subsidence of the implant, distribute the implant load over a larger surface area, and provide increased surface area for bone ingrowth. A plurality of pegs 916 protrude from the bone-engaging portion 914 and may prevent rotation of the base. The pegs 916 are positioned farther away from the central axis of the base 910, in comparison to the configuration of base 900 and pegs 908.

Figure 19:
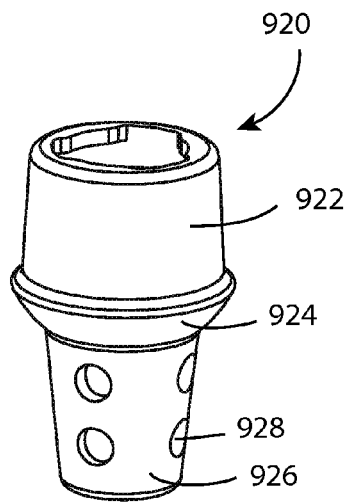
FIG. 19 is a lateral perspective view of an alternate fixation assembly base member.

Referring to FIG. 19, another alternative embodiment of an implant base member is shown. Implant base 920 comprises a tapered portion 922, a spherical transition portion 924, and a bone-engaging portion 926. Bone-engaging portion 926 is tapered and includes a plurality of holes 928 which open into the central cannulated area, and may allow additional bone ingrowth. Bone-engaging portion 926 may provide a narrower profile allowing for less disturbance of the pedicle during preparation and implantation.

Figure 20:
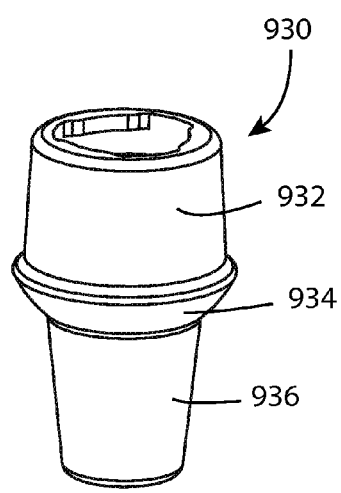
FIG. 20 is a lateral perspective view of an alternate fixation assembly base member.

Referring to FIG. 20, another alternative embodiment of an implant base member is shown. Implant base 930 comprises a tapered portion 932, a spherical transition portion 934, and a tapered bone-engaging portion 936.

Figure 21:
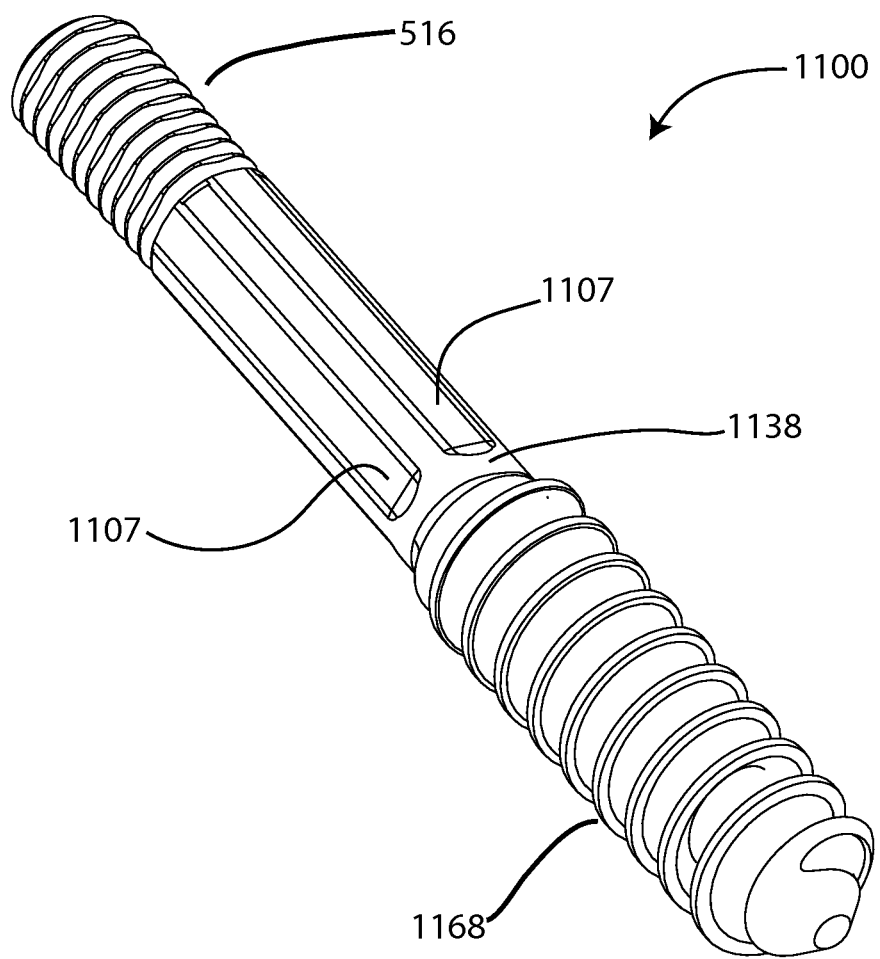
FIG. 21 is a perspective view of an alternate embodiment of a fixation member.

FIG. 21 illustrates an alternate embodiment of a fixation element, or pedicle screw 1100. The pedicle screw 1100 has a distal threaded bone engaging portion 1168, a shaft 1138, and a proximal threaded attachment portion 516. These features may be similar to, or identical to, those disclosed for fixation element 302. Pedicle screw 1100 also has a plurality of flats 1107 arranged around the proximal end. The flats 1107 may extend along at least a portion of the proximal threaded attachment portion 516 or the shaft 1138. In a preferred embodiment, the flats 1107 extend along the majority of the shaft 1138 and the entire proximal threaded attachment portion 516.

Figure 22:
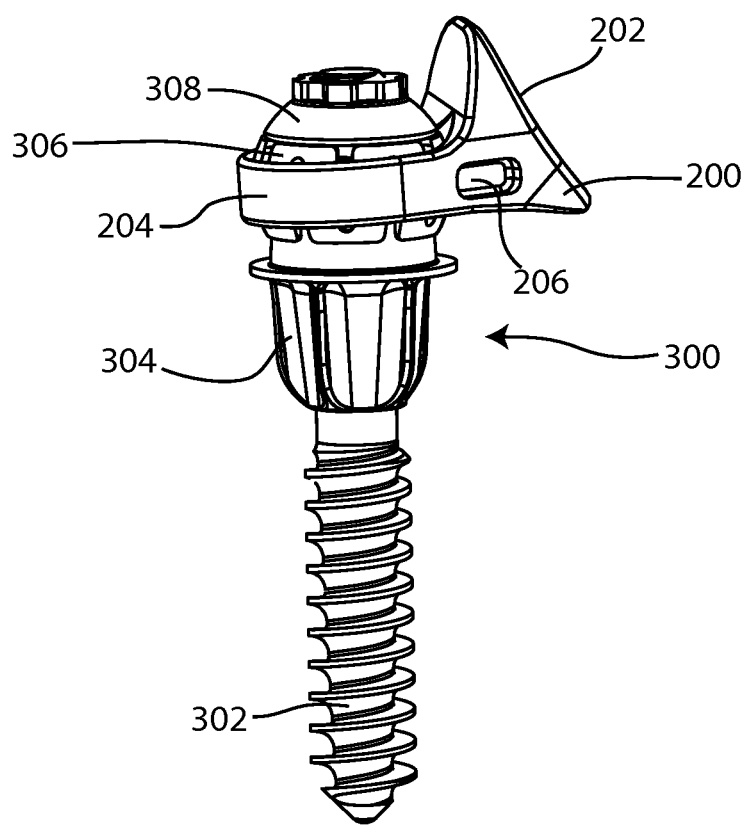
FIG. 22 is a perspective view of a fixation assembly secured to a superior facet joint implant.

Referring to FIG. 22, the superior implant 200 is shown secured to the fixation assembly 300. The superior implant 200 may be monolithic and includes a superior articulation surface 202 shaped to replace a natural superior articular surface of a vertebra, a ring 204, and may include at least one notch-like gripping feature 206. The superior implant 200 may be secured to the fixation assembly 300 in the same method as described previously for the inferior strut 104. The ring 204 of the superior implant 200 is locked in position relative to the split sphere 306 and the base 304. The base 304, split sphere 306 and implant 200 may be dropped over an implanted fixation member 302, and the top nut 308 secured on the fixation member 302 to retain the assembly. The superior implant 200 may be delivered in combination with an inferior implant 100, and the superior articular surface 202 may be temporarily clipped to the inferior articular surface 122.

A kit of superior implants may be provided, wherein each superior implant in the kit is a different size or shape so that a particular superior implant may be selected for implantation at a certain operative site. U.S. patent application Ser. No. 12/240,320, which is incorporated herein by reference in its entirety, describes such a kit of superior implants in terms of physical dimensions which may vary independently among the various superior implants in the kit.

Some of the physical dimensions that may change between the different sizes of superior implants are an X1 offset, a Y1 offset and a facet angle. These dimensions may be used to describe the location and orientation of the superior articular surface of the superior implant with respect to local vertebral landmarks, such as a pedicle saddle point or pedicle axis, or standard anatomical reference planes such as the sagittal plane 3. It can be appreciated that the same dimensions may be measured on one or more intact natural vertebrae in order to develop superior implants that accurately fit a majority of the patient population.

The pedicle axis may be the same as the longitudinal axis of fixation member 302, or any other fixation member disclosed herein, after implantation into a pedicle. The pedicle axis may also be the axis passing along the center of a substantially tubular midportion of the pedicle, independent of any fixation member. The pedicle saddle point is frequently equivalent to the entry point of a fixation member into the pedicle; it may also be defined as the intersection of the pedicle axis and the posterior bone surface lateral to the superior articular process of a vertebra.

Exemplary values for the foregoing dimensions will be provided below. Although the exemplary values relate primarily to L5 superior and L4 inferior, they may apply to other combinations of vertebrae in the lower back and/or the sacrum. One or more of these variables can change between the different superior implant sizes.

For a particular superior articular surface and its immediately adjacent pedicle, the point P1 is the most medial and anterior point on the superior articular surface. P1 is displaced from the saddle point S1 by an X1 offset and a Y1 offset. The direction of the Y1 offset is parallel to the pedicle axis. The direction of the X1 offset is perpendicular to the direction of the Y1 offset. The direction of the X1 offset is generally, but not precisely, lateral to medial with respect to the central axis of the patient's spine.

The X1 offset for a superior implant can range from 5 mm to 30 mm. However, for the majority of patients, the X1 offset will range from 10 mm to 20 mm. Therefore a family of superior implants can be provided with the X1 offset varying in increments of 5 mm. Thus, sets of superior implants would be provided with X1 offset at 10 mm, 12 mm, 14 mm, 16 mm, 18 mm, and 20 mm to cover the statistical range for the majority of the population of patients needing superior implants.

The Y1 offset for a superior implant can range from 2 mm to 20 mm. However, for the majority of patients, the Y1 offset will range from 5 mm to 15 mm. Therefore a family of superior implants can be provided with the Y1 offset varying in increments of 2 mm. Thus, sets of superior implants would be provided with Y1 offset at 5 mm, 7 mm, 9 mm, 11 mm, 13 mm, and 15 mm to cover the statistical range for the majority of the population of patients needing superior implants.

The facet angle for a superior implant is the angle that the superior articular surface makes with respect to a plane perpendicular to the pedicle axis and passing through point P1. The facet angle can range from 50° to 120°. However, for the majority of patients, the facet angle will range from 60° to 100°. Therefore a family of superior implants can be provided with the facet angle varying in increments of 5°. Thus, sets of superior implants would be provided with the facet angle at 60°, 65°, 70°, 75°, 80°, 85°, 90°, 95°, and 100° to cover the statistical range for the majority of the population of patients needing superior implants.

The parameters of the superior implant may include at least two dimensions that vary among the members of the kit independently of each other. Dimensions that vary independently of each other need not change according to any established relationship between the dimensions, but instead, one may change while the other remains the same between any two prostheses of the kit.

Figure 24:
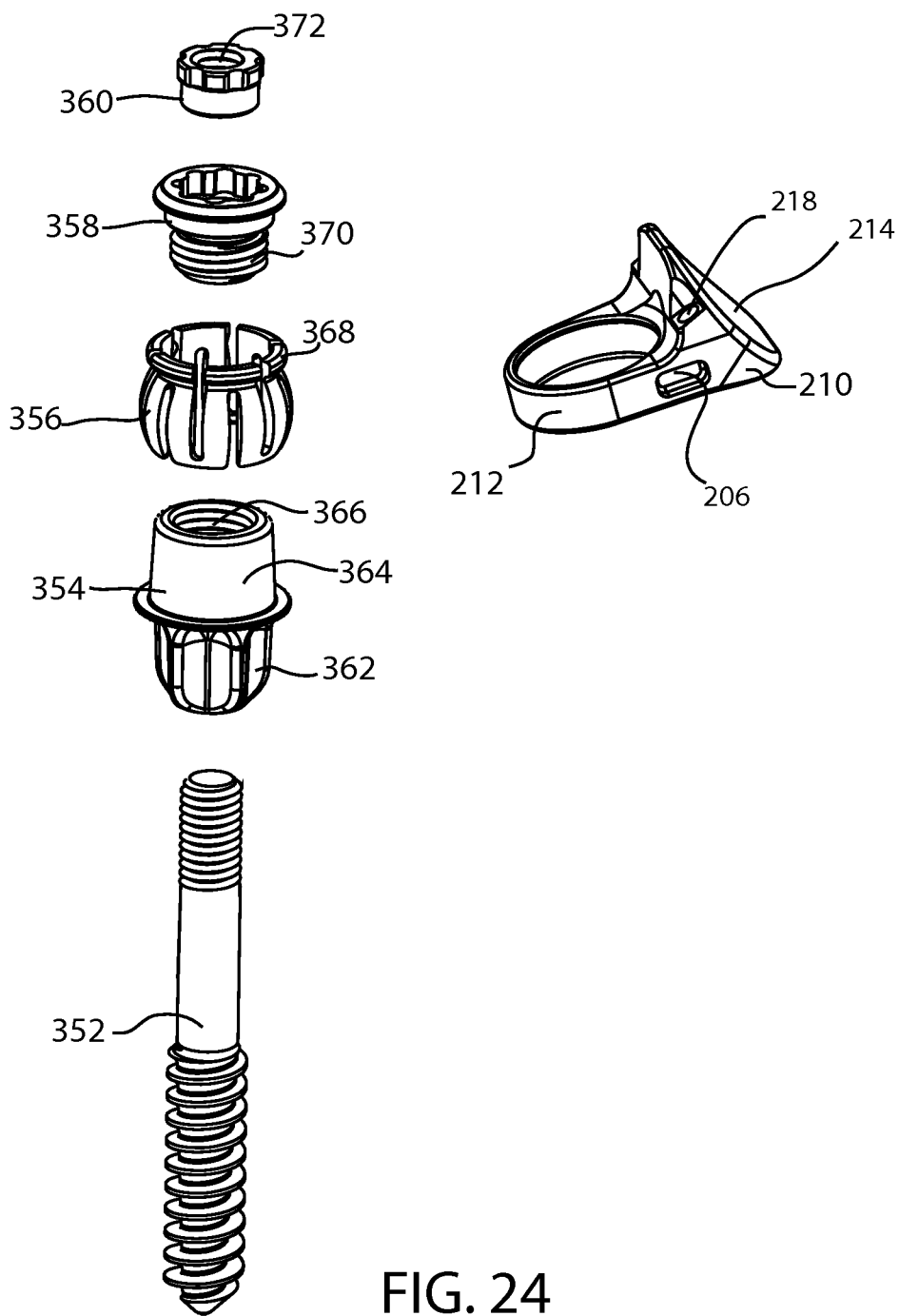
FIG. 24 is an exploded view of the alternate fixation assembly and superior facet joint implant of FIG. 23.
Figure 25:
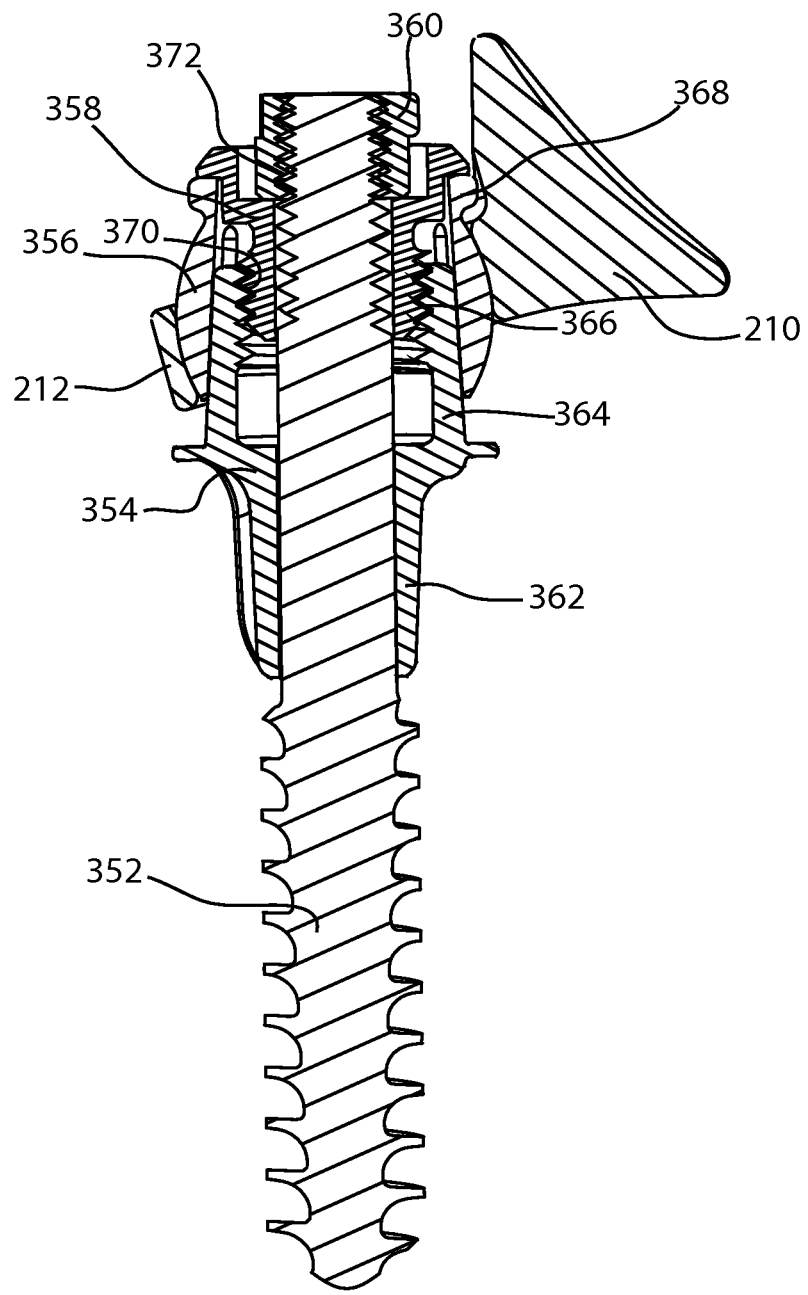
FIG. 25 is a cross-sectional view of the alternate fixation assembly and superior facet joint implant of FIG. 23.
Figure 28:
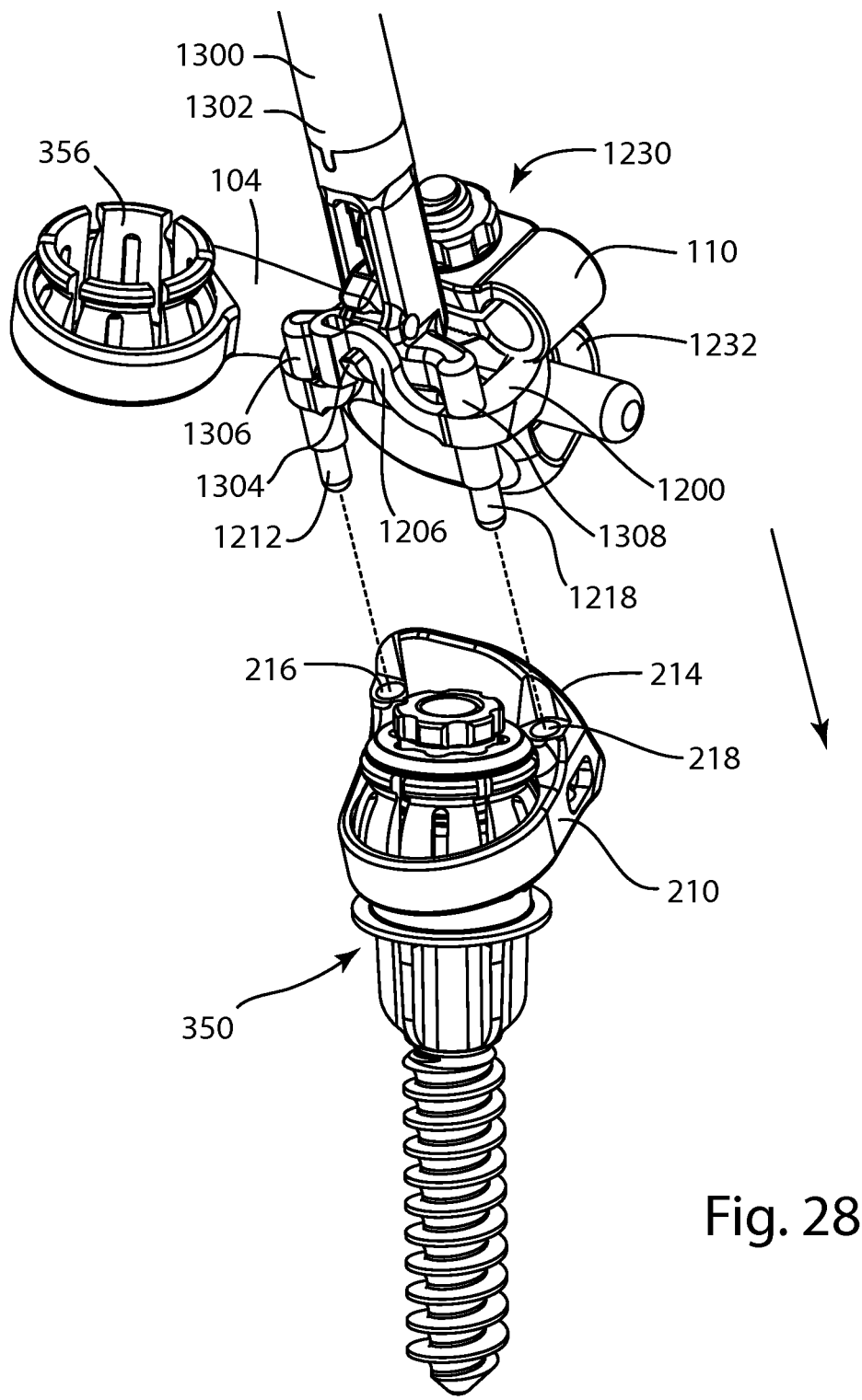
FIG. 28 is a perspective view of the clip and inferior implant of FIG. 7 coupled to a delivery tool, and the superior facet joint implant and fixation assembly of FIG. 23.

FIG. 23 presents an alternative embodiment of a superior implant 210 with an alternative embodiment of a polyaxially adjustable fixation assembly 350. FIG. 24 presents an exploded view of fixation assembly 350, and FIG. 25 presents a cross-sectional post-assembly view of the assembly. With reference to FIGS. 23 and 28, superior implant 210 is distinguished from superior implant 200 by holes 216 and 218 disposed between the ring and the articular surface. With reference to FIGS. 23-25, fixation assembly 350 comprises a fixation member 352, a tapered base 354, a flanged split sphere 356, a capture nut 358, and a top nut 360. The cannulated tapered base 354 has an inset portion 362 which may include anti-rotation features such as fins, teeth or studs. A tapered portion 364 has a threaded lumen 366. The split sphere 356 includes a split flange 368 which encircles one open end of the sphere. The capture nut 358 has a threaded outer surface 370, while the top nut 360 has a threaded inner surface 372. Fixation assembly 350 may also be termed an attachment mechanism. It is appreciated that fixation assembly 350 may be substituted for fixation assembly 300 in any fixation procedure disclosed or depicted herein, and vice versa. Also, a combination of fixation assemblies 300 and 350 may be used in an implant system.

Figure 26:
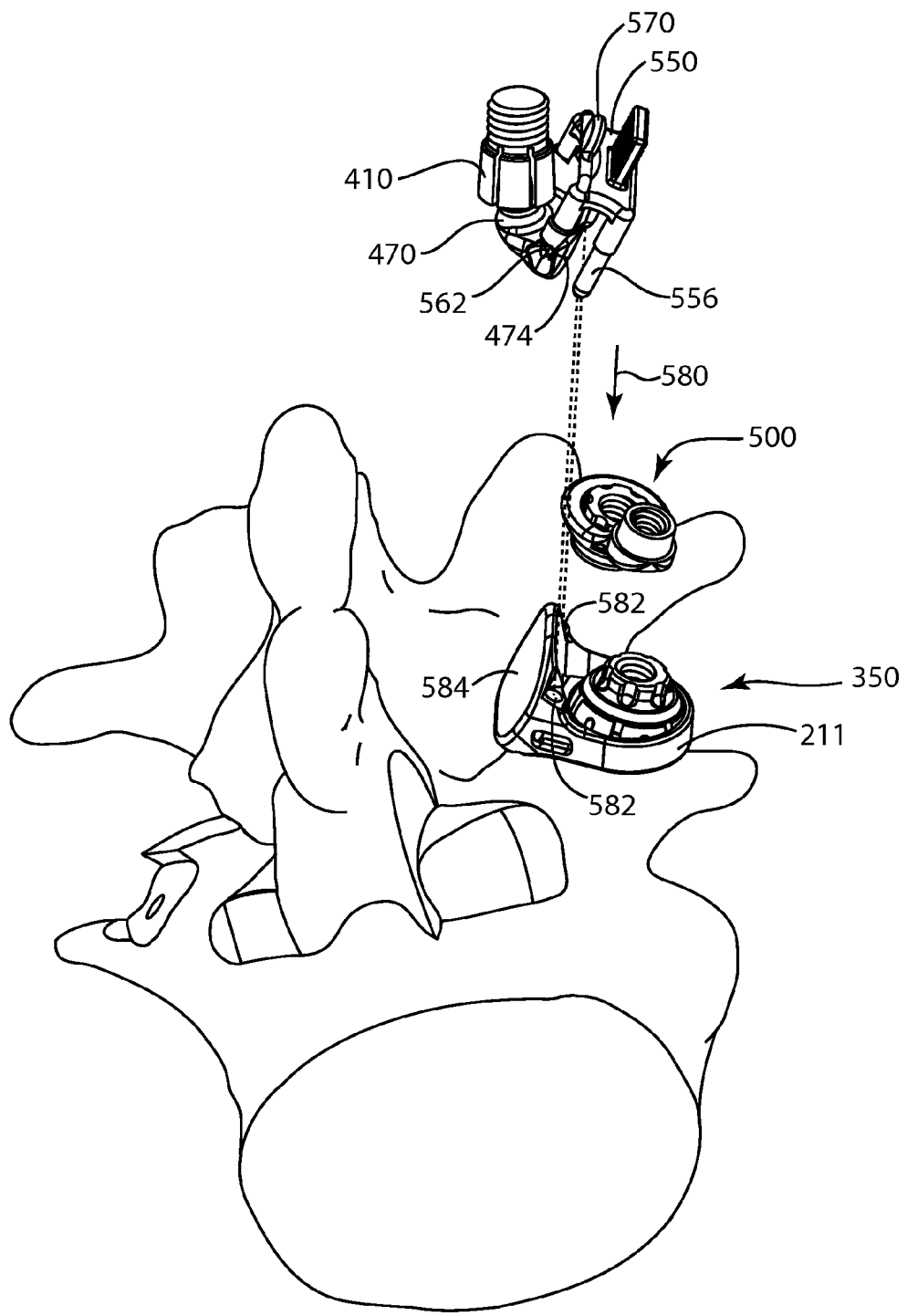
FIG. 26 is a perspective view of the clip of FIG. 5 coupled to an inferior facet joint implant, and the superior facet joint implant and fixation assembly of FIG. 23.

Referring to FIG. 26, a perspective view shows the inferior articular body 470 attached to a clip 550. A direction arrow 580 indicates the direction in which the articular body and clip may be moved to align them with a superior implant 211. The superior implant 211 may be implanted in a pedicle via fixation assembly 350 prior to alignment with the inferior articular body 470. Using the handle 554, the clip may be moved until the superior pins 556 fit into openings 582 on the superior implant 211. Alternatively, clip 550 and inferior articular body 470 may be joined with an inferior strut (not shown) and with superior implant 211 into an assembly, and the assembly moved onto fixation members 352 implanted in the pedicles.

Figure 27:
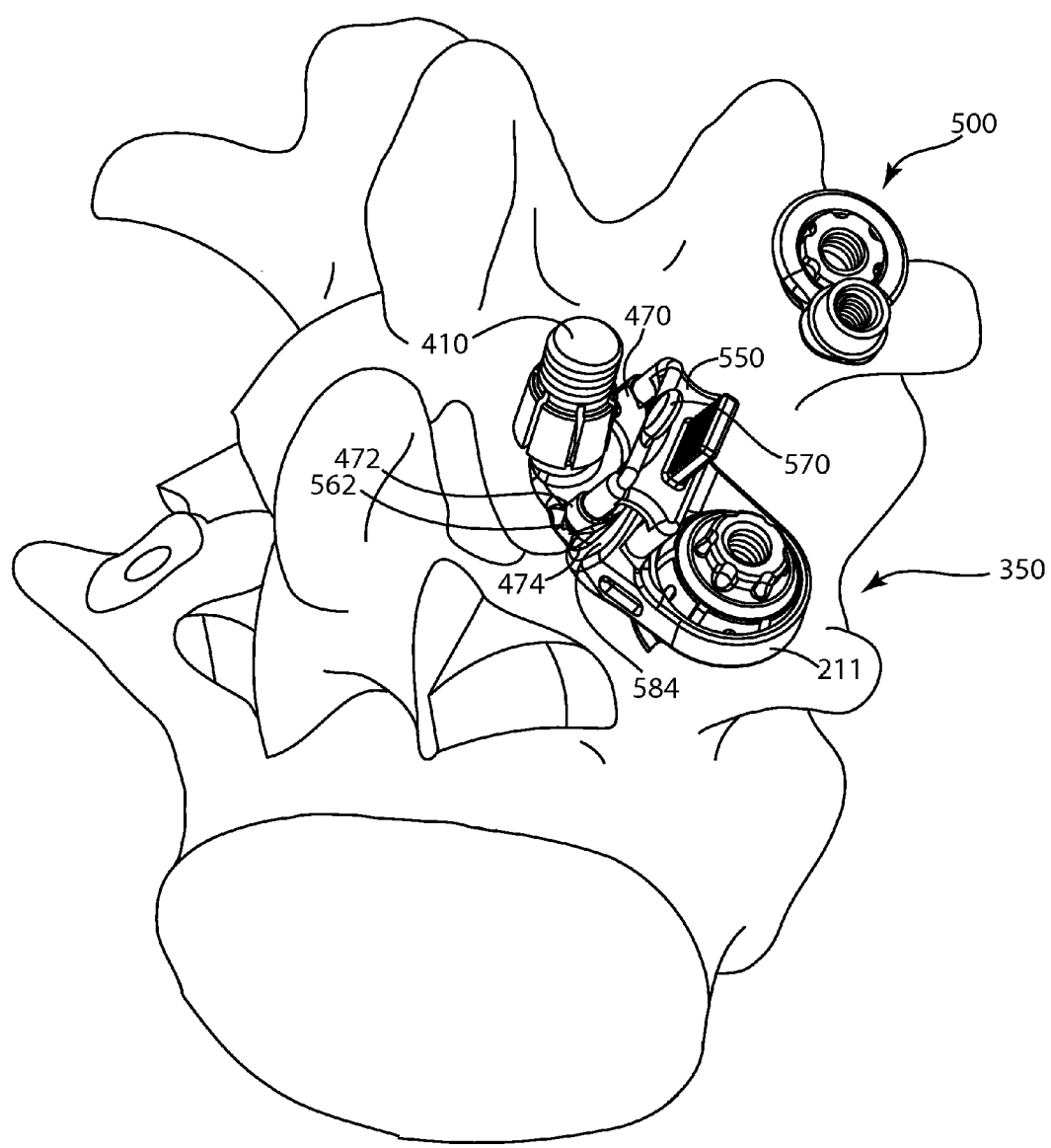
FIG. 27 is a perspective view of the inferior and superior facet joint implants of FIG. 26 joined by the clip of FIG. 5.

As seen in FIG. 27, when the pins 556 are fully inserted into the openings 582, inferior articulation surface 474 is aligned with superior articulation surface 584 in a preferred orientation. At this point, an appropriately sized and configured inferior strut (not shown) may be chosen. The orientation of the inferior strut may be adjusted before being locked down to a fixation member. Additionally, a crosslink rod (not shown) may be added and locked down as the attachment mechanism is locked down. To remove the clip 550, first the plug 570 is removed, allowing the split ends 562 to return to the first narrow configuration and making them narrow enough to be withdrawn through the tubes 472. Then the clip 550 may be removed.

Referring to FIG. 28, clip 1200 and implant 1230 are shown gripped by a delivery tool 1300. Additionally, superior facet implant 210 is shown coupled to fixation assembly 350. The delivery tool 1300 comprises handles (not shown), a shaft 1302, a hook 1304 which may be actuated to grip and release the clip 1200, and a pair of pegs 1306, 1308. Upon removal of the packaging described above, the delivery tool 1300 may be connected to the clip 1200 via the hook 1304 which hooks on the connection portion 1206, and the pegs 1306, 1308 which protrude into the recesses 1220, 1222. The spacing of the pegs keeps the posts 1212, 1218 of the clip 1200 in a proper position for coupling with the superior implant 210. The hook 1304 may prevent premature flexure of the connection portion 1206. The delivery tool 1300 may be manipulated to position the clip 1200 and implant 1230 such that the posts 1212, 1218 fit into the holes 216, 218 on the superior implant, thus properly aligning the inferior 1234 and superior 214 articulation surfaces relative to one another.

Figure 29:
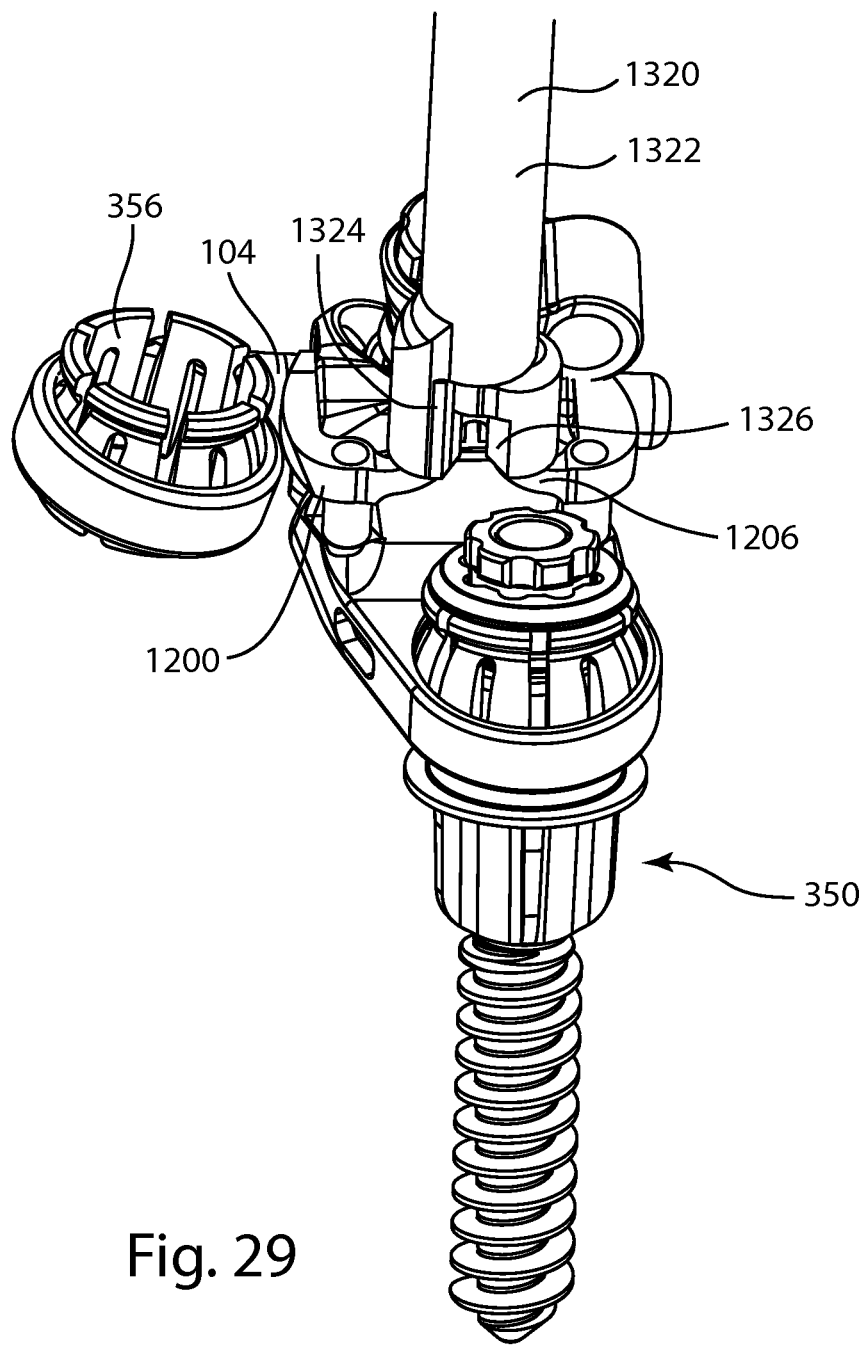
FIG. 29 is a perspective view of the clip and inferior implant of FIG. 7 coupled to a flexing tool, coupled to the superior facet joint implant and fixation assembly of FIG. 23.

Referring to FIG. 29, a flexing tool 1320 is shown coupled to the connecting portion 1206 of the clip 1200. Flexing tool 1320 is co-axial, and comprises handles (not seen), a shaft 1322, and two gripping features 1324, 1326. The gripping features 1324, 1326 are shaped and positioned to grip two locations on the connecting portion 1206. The flexing tool 1320 may be activated to move the gripping features 1324, 1326 relative to one another such that the connecting portion 1206 is flexed.

Figure 30A:
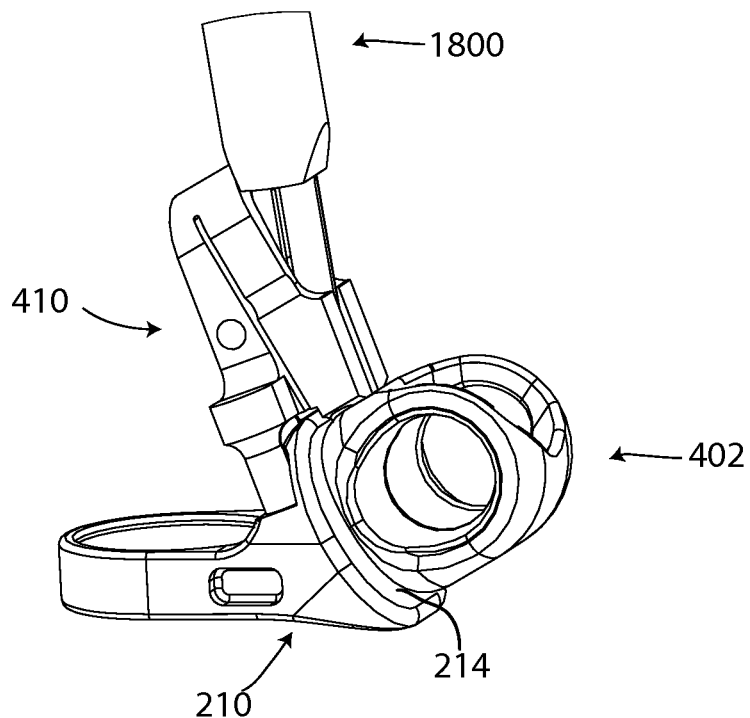
FIG. 30A is a perspective view of the clip of FIG. 10 coupled to the inferior implant of FIG. 8, the superior implant of FIG. 23, and an inserter tool.
Figure 30B:
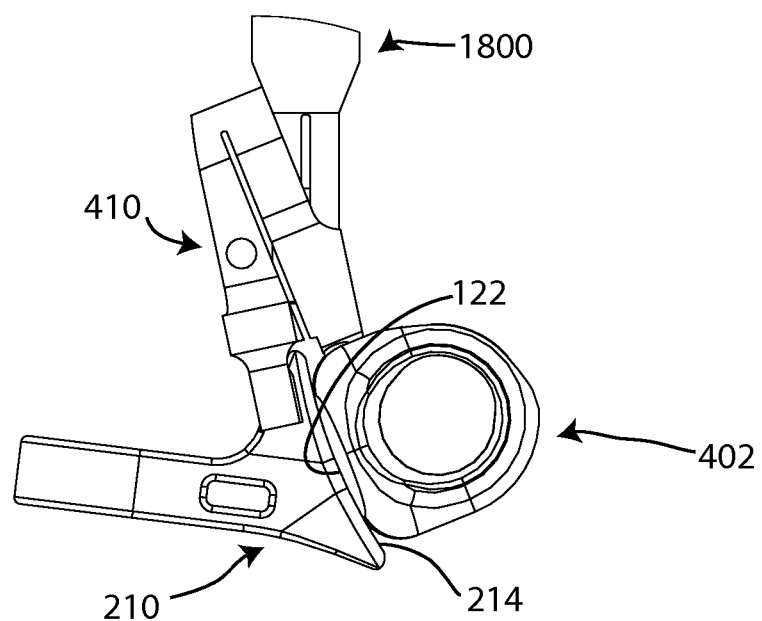
FIG. 30B is a side view of the clip, inferior implant, superior implant, and inserter tool of FIG. 30A.
Figure 31:
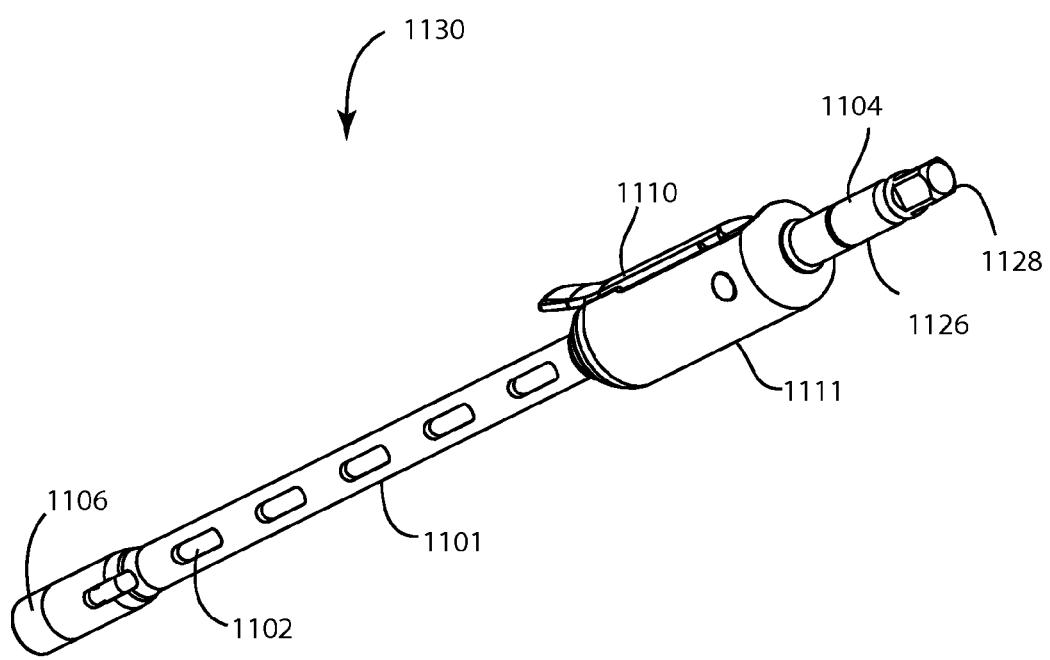
FIG. 31 is a perspective view of a screw driver.
Figure 32:
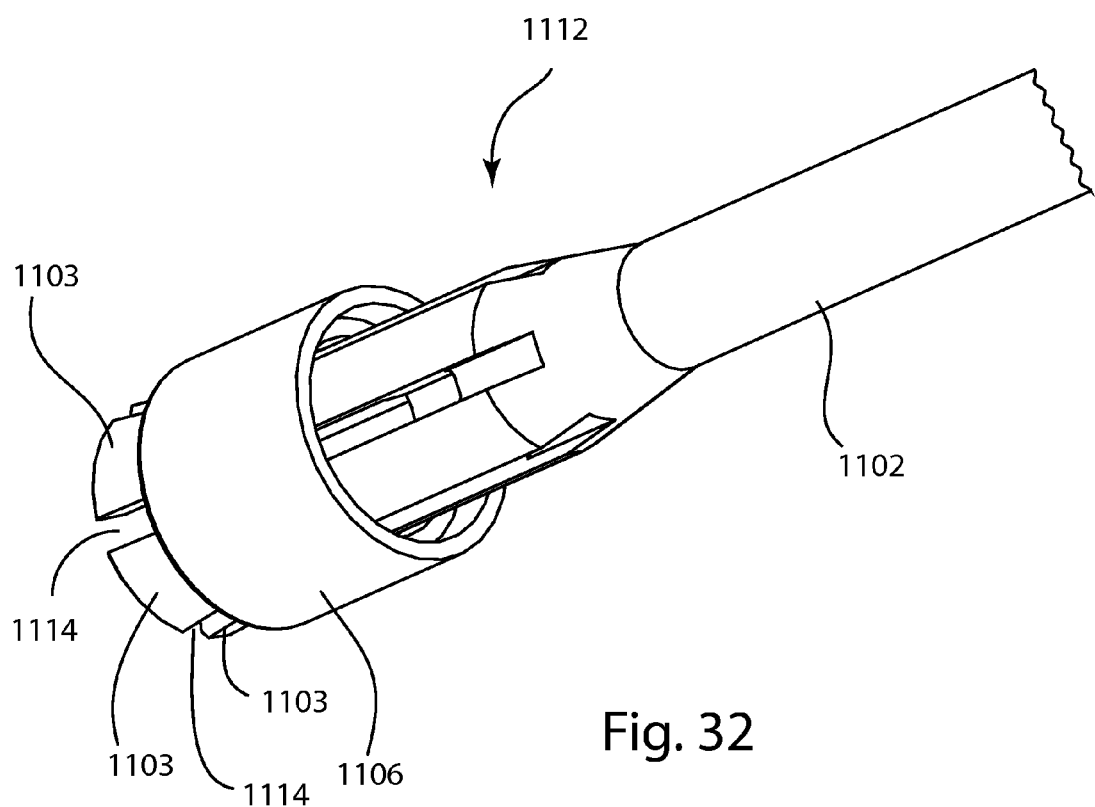
FIG. 32 is a detail view of a collet and a distal tip component of the screw driver of FIG. 31.
Figure 33:
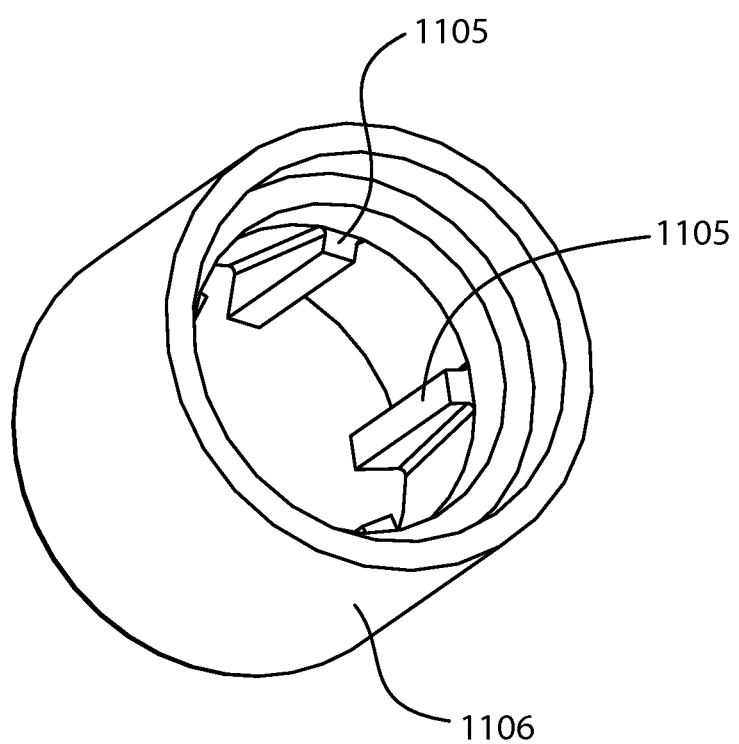
FIG. 33 is a detail view of the distal tip of FIG. 32.

Referring to FIG. 30, inferior articular body 402 is shown coupled to superior implant 210 by clip 410. An inferior inserter 1800 is also coupled to the clip 410. Optionally, the inferior articular body 402 may be assembled to other components of the inferior facet joint implant 400 (FIG. 8). A split sphere 306 or 356 may be provided with the inferior implant 400 or the superior implant 210. Furthermore, the superior implant 210 may already be locked to a fixation assembly implanted in a pedicle. However, these additional components are not shown in FIG. 30 for clarity. Inferior articular body 402 is coupled to superior implant 210 by clip 410 in a manner similar to that described for inferior articular body 470, clip 550, and superior implant 211 (FIG. 26) and inferior articular body 1230, clip 1200, and superior implant 210 (FIG. 28). The inferior inserter 1800 may be used to position the clip 410 and inferior articular body 402 so that the prongs 416 of clip 410 engage the holes 216 and 218 of the superior implant 210 so that the inferior articulation surface 122 is properly aligned to the superior articulation surface 214.

The coupling clips disclosed herein may be made in a variety of sizes, and with varied dimensions, to fit implants configured for different vertebral levels. Other embodiments of clips may include different deformable retention features, different alignment features, and/or different features shaped to receive the superior and inferior implants. Coupling clips without deformable features or plugs, and/or with other attachment features are contemplated within the scope of the invention. In addition, trial clips in a variety of sizes and configurations may be provided, to allow the practitioner to choose the correct size or configuration of implant. Trial clips may include integrated superior and/or inferior implant trial components. A trial clip and implant may be used to select the proper length of inferior strut to match an offset distance between the vertebrae. Specifically, fixation members and base members may be secured in adjacent vertebrae, and a succession of trials, each comprising a clip retaining an inferior and optionally a superior implant may be positioned on the bases, until the proper length of inferior strut is determined. Then the sterile package containing the proper choice of clip and implants may be opened and the appropriate clip and implants secured to the base members. Use of the trials prevents practitioners from unnecessarily opening more than one sterile package of implants to determine a correct fit.

The facet joint replacement system 10 described above, and alternate embodiments thereof, may be implanted using a set of surgical instruments. At least some of the surgical instruments may be specifically designed to facilitate implantation of one or more implant embodiments disclosed herein. Selected surgical instruments that may facilitate implantation of one or more embodiments of the facet joint replacement system will now be described.

FIGS. 31-36 illustrate a first embodiment of a pedicle screw driver 1130. The screw driver 1130 comprises an outer sleeve 1101, an inner shaft 1102, a handle 1111, a lever 1110, a coupling element 1121, and a torque fitting 1104.

The outer sleeve 1101 is generally tubular and may be windowed. The inner surface of the outer sleeve 1101 may have one or more tabs 1105 near the distal end 1106. The tabs 1105 may be formed on a separate distal tip portion which is subsequently affixed to the remaining portion of outer sleeve 1101, as is shown in FIGS. 31-36, or the tabs 1105 may be formed as separate parts which are affixed to a unitary outer sleeve 1101. The tabs 1105 may also be integrally formed with the outer sleeve 1101. The distal end 1106 of the outer sleeve 1101 may optionally comprise a replaceable burr or reamer with end cutting flutes or side cutting flutes, or both. End cutting flutes, if present, may extend only partway from the outer diameter of outer sleeve 1101 toward the inner surface so that a non-fluted annular region is present.

The inner shaft 1102 slides within the outer sleeve 1101, and is held in a fixed rotational alignment to the outer sleeve 1101, as will be described below. The inner shaft 1102 has a collet 1112 on the distal end, as is best seen in FIGS. 31 and 33-35. The collet 1112 comprises a center bore 1113 surrounded by a plurality of flexible prongs 1103 separated by slots 1114. The center bore 1113 may be fabricated with a precisely controlled predetermined depth from the open end of the collet 1112. In the free state, i.e., when subject to no external forces, the prongs 1103 flare toward the open end of the collet 1112. When the collet 1112 slides within the distal end 1106 of outer sleeve 1101, the prongs 1103 are compressed toward the center bore 1113 by the inner surface of the outer sleeve 1101. The one or more tabs 1105, if present, slide into one or more corresponding slots 1114 in the collet 1112 to fix the rotational alignment of the collet 1112 to the outer sleeve 1101. One or more of the inner walls 1115 of the prongs 1103 may be flattened so that the center bore 1113 is non-circular or polygonal in cross section.

The handle 1111 is rigidly fixed to the proximal end of the outer sleeve 1101, and is generally tubular. The ends of handle 1111 may be reduced in diameter to blend with the outer diameter of the outer sleeve 1101. The handle 1111 may have a slot 1118 through which the lever 1110 protrudes.

The lever 1110 is pivotally attached to the handle 1111 by pins 1122 and to the coupling element 1121 by pin 1119. In the embodiment shown, the lever 1110 protrudes through slot 1118 in the handle 1111. The lever 1110 pivots between a first position, in which the lever 1110 lies generally flat against the handle 1111, and a second position, in which the free end of the lever 1110 lifts away from the handle 1111. The coupling element 1121 comprises a curved bar which is pivotally attached to the inner shaft 1102 by pin 1120. Thus, the lever 1110, coupling element 1121, and inner shaft 1102 form a mechanical linkage 1124 which is pinned to handle 1111 by pins 1122. The linkage 1124 turns rotational motion of the lever 1110 into linear translation of the inner shaft 1102 within the outer sleeve 1101. The linkage 1124 also holds inner shaft 1102 in a fixed rotational alignment to the outer sleeve 1101.

The torque fitting 1104 is rigidly fixed to the proximal end of the handle 1111. In the embodiment shown, the torque fitting 1104 is a shaft 1126 terminating in a square tip 1128 suitable for connection to a modular handle or power driver (not shown). However, other torque fittings are contemplated, such as a hexagonal tip, threads, or other fittings as are known in the art. The handle 1111 itself may serve as a manual torque fitting 1104.

The outer sleeve 1101 and inner shaft 1102 of the screw driver 1130 cooperate to form a screw coupling 1116 that releasably couples the screw driver 1130 to a fixation element such as pedicle screw 1100 (FIG. 21). In the embodiment illustrated in FIGS. 31-36, the screw coupling 1116 is formed by the collet 1112 at the distal end of the inner shaft 1102 and the distal end 1106 of the outer sleeve 1101 adjacent to the collet 1112. The distal end 1106 of outer sleeve 1101 forms a socket 1117 around the collet 1112, and the center bore 1113 of collet 1112 forms a socket around the pedicle screw 1100. The screw coupling 1116 has an unlocked configuration, in which the pedicle screw 1100 and the screw driver 1130 are separable. The screw coupling 1116 also has a locked configuration, in which the pedicle screw 1100 and the screw driver 1130 are inseparable. Furthermore, in the locked configuration, the screw coupling 1116 transmits torque from the screw driver 1130 to the pedicle screw 1100 in order to thread the pedicle screw 1100 into a pedicle or other part of a bone.

When the free end of the lever 1110 is lifted away from the handle 1111, the lever 1110 rotates about pins 1122. A first end 1132 of coupling element 1121 also rotates about pins 1122, because coupling element 1121 is pivotally attached to the lever 1110 by pin 1119. As the first end 1132 of coupling element 1121 rotates, it moves toward the distal end 1106 of the outer sleeve 1101; it also pushes a second end 1134 of coupling element 1121 toward the distal end 1106 of the outer sleeve 1101. A proximal end 1136 of the inner shaft 1102 is also pushed toward the distal end of the screw driver 1130, because it is pivotally attached to the second end 1134 of the coupling element 1121 by pin 1120. The curved shape of coupling element 1121 allows it to flex, or behave as a spring, in response to the applied forces on the first end 1132 and any resisting forces on the second end 1134. Inner shaft 1102 is only capable of linear translation within outer sleeve 1101, due to the constraints imposed by outer sleeve 1101, handle 1111, lever 1110, and coupling element 1121. Thus, when the free end of the lever 1110 is lifted away from the handle 1111, the proximal end 1136 of the inner shaft translates toward the distal end 1106 of the outer sleeve 1101 such that at least a portion of the distal collet 1112 protrudes past the distal end 1106 of the outer sleeve 1101. In this position, the inner surface of outer sleeve 1101 does not touch the collet 1112, so the prongs 1103 flare toward the open end of the collet 1112. This configuration of the screw driver 1130 is called the unlocked configuration because the collet 1112 is unconstrained by the outer sleeve 1101 and the prongs 1103 flare open to receive the pedicle screw 1100 in the center bore 1113, as will be described presently. Thus, the unlocked configuration of the screw driver 1130 corresponds to the unlocked configuration of the screw coupling 1116.

When the lever 1110 is rotated to lie generally flat against the handle 1111, the first end 1132 of coupling element 1121 moves away from the distal end 1106 of the outer sleeve 1101; it also pulls the second end 1134 of coupling element 1121 away from the distal end 1106 of the outer sleeve 1101. The proximal end 1136 of the inner shaft 1102 is also pulled away from the distal end 1106 of the outer sleeve 1101. The curved shape of coupling element 1121 allows it to flex, or behave as a spring, in response to the applied forces on the first end 1132 and any resisting forces on the second end 1134. Thus, when the lever 1110 lies generally flat against the handle 1111, the proximal end 1136 of the inner shaft 1102 translates away from the distal end 1106 of the outer sleeve 1101 such that a substantial portion of the distal collet 1112 is retracted within the distal end 1106 of the outer sleeve 1101. In a preferred embodiment, the open end of the collet 1112 is precisely aligned with the distal end 1106 of the outer sleeve 1101 such that the center bore 1113 is at a precisely controlled predetermined depth from the distal end 1106 of the outer sleeve 1101. In this position, the inner surface of outer sleeve 1101 contacts the collet 1112, compressing the prongs 1103 toward the center bore 1113 as described above. The one or more tabs 1105, if present, engage one or more corresponding slots 1114 in the collet 1112 as described above. This configuration of the screw driver 1130 is called the locked configuration because the collet 1112 is compressed by the outer sleeve 1101 so that the prongs 1103 will grasp a pedicle screw 1100 in the center bore 1113, as will be described below. Thus, the locked configuration of the screw driver 1130 corresponds to the locked configuration of the screw coupling 1116.

FIGS. 37A-38E illustrate a second embodiment of a pedicle screw driver 1140. In this embodiment, the screw driver 1140 comprises an outer sleeve 1142 and an inner shaft 1144 which differ from the previous embodiment, as well as a handle 1146, a lever 1148, a coupling element 1150, and a torque fitting 1152 which may be similar or identical to those described for screw driver 1130.

The outer sleeve 1142 is generally tubular and may be windowed. The inner surface of the outer sleeve 1142 has internal threads extending from a distal end 1164 along at least a portion of the length of the outer sleeve 1142. The internal threads are complementary to the external threads on the proximal attachment portion 516 of pedicle screw 1100. In other regards, the outer sleeve 1142 may be similar or identical to the outer sleeve 1101 described for screw driver 1130. The distal end 1164 of the outer sleeve 1142 may optionally comprise a replaceable burr or reamer, as described for screw driver 1130.

The inner shaft 1144 slides within the outer sleeve 1142, and is held in a fixed rotational alignment to the outer sleeve 1142. The inner shaft 1144 terminates in a blunt distal end 1160. In other regards, the inner shaft 1144 may be similar or identical to the inner shaft 1102 described for the previous embodiment.

The handle 1146, lever 1148, and coupling element 1150 depicted for screw driver 1140 may differ in appearance from, but may retain the same function as, those described for screw driver 1130. In this embodiment, handle 1146 serves as a manual torque fitting 1152.

The outer sleeve 1142 and inner shaft 1144 of the screw driver 1140 cooperate to form a screw coupling 1162 that releasably couples the screw driver 1140 to pedicle screw 1100. In the embodiment illustrated in FIGS. 37A-38E, the screw coupling 1162 is formed by the blunt end 1160 of the inner shaft 1144 and the internally threaded distal end 1164 of the outer sleeve 1142. The distal end 1164 of the outer sleeve 1142 forms a socket 1166 around the fixation element and the distal end 1160 of the inner shaft 1144 serves as the bottom of the socket 1166. The screw coupling 1162 has an unlocked configuration, in which the fixation element and the screw driver 1140 are separable. The screw coupling 1162 also has a locked configuration, in which the fixation element and the driver 1140 are inseparable. Furthermore, in the locked configuration, the screw coupling 1162 transmits torque from the driver 1140 to the fixation element in order to thread the fixation element into a pedicle or other part of a bone.

The operation of the lever 1148 to select the unlocked or locked configuration is as described above with regard to screw driver 1130. However, due to the relative locations of the pivot points between the lever 1148 and handle 1146 and between the lever 1148 and a first end of the coupling element 1150, the motion of inner shaft 1144 is reversed compared to screw driver 1130. When the free end of the lever 1148 is lifted away from the handle 1146, the inner shaft 1144 is pulled away from the distal end of the outer sleeve 1142. When the lever 1148 is rotated to lie generally flat against the handle 1146, the inner shaft 1144 is pushed toward the threaded distal end 1164 of the outer sleeve 1142. In a preferred embodiment, the blunt distal end 1160 of the inner shaft 1144 may lie at a precisely controlled predetermined depth relative to the threaded distal end 1164 of the outer sleeve 1142 when screw driver 1140 is in the locked position.

It can be appreciated that the screw driver 1140 may also be used with fixation member 302 or 352, since the screw coupling 1162 is configured to engage the proximal threads and the proximal end of the fixation member.

The lever and coupling element may be replaced in alternate embodiment screw drivers with other means of selecting between the unlocked and locked configurations. For example, the lever and coupling element may be replaced with a mechanism that includes a knob that threads directly or indirectly to the inner shaft to move the inner shaft with respect to the outer sleeve. In such an embodiment, turning the knob clockwise, for example, may move the inner shaft away from the distal end of the outer sleeve, while turning the knob counterclockwise may move the inner shaft toward the distal end of the outer sleeve.

FIG. 39 illustrates an embodiment of a base reamer 1250. The base reamer 1250 comprises a replaceable reamer tip 1252, an outer sleeve 1254, an optional inner shaft 1256, and a torque fitting 1258. The base reamer 1250 may cooperate with a shield (not shown), which may be a tube sized to slide over at least the reamer tip 1252 to isolate the reamer tip 1252 from surrounding soft tissues.

The replaceable reamer tip 1252 comprises a first cutting portion 1260, a second cutting portion 1262, a center bore 1274 and a shaft portion 1264. The first cutting portion 1260 and second cutting portion 1262 may be configured to correspond to a particular implant base embodiment. Therefore, a set of reamer tips may be provided, wherein each reamer tip in the set corresponds to a different implant base configuration. The first cutting portion 1260 is at the distal end of the reamer tip 1252, and may comprise side cutting flutes 1266, or end cutting flutes 1268, or both. An embodiment having both side-1266 and end-cutting 1268 flutes is shown in FIG. 39. First cutting portion 1260 may cut a cylindrical hole, a conical hole, or some other shape. First cutting portion 1260 may be windowed, as shown. The second cutting portion 1262 is proximally adjacent to first cutting portion 1260, and may comprise side cutting flutes 1270, or end cutting flutes 1272, or both. An embodiment having both side-1270 and end-cutting 1272 flutes is shown in FIG. 39. Second cutting portion 1262 cuts a larger diameter hole adjacent to the hole cut by first cutting portion 1260. The transition between the smaller diameter of first cutting portion 1260 and the larger diameter of second cutting portion 1262 may be flat as shown, i.e., perpendicular to the center axis 1261 of the cutting portions 1260, 1262, conical, convex, concave, or it may comprise a gradually curving transition, depending on the configuration of the corresponding implant base. For at least some embodiments, the combined transition and larger diameter hole can be considered a counterbore or a spot face. A counterbore is a larger diameter added at the open end of a smaller diameter hole, with a flat surface between the two diameters, which may be for the purpose of creating a recessed space for the head of a fastener. A spot face is a shallow, larger diameter added at the top of a hole, which may be for the purpose of creating a flat surface around the hole. Center bore 1274 extends through the full length of reamer tip 1252. Bore 1274 is sized to spin freely over the proximal threaded attachment portion and shaft of any of the fixation members or pedicle screws described herein. Shaft portion 1264 comprises a threaded interconnection 1265 to removably connect reamer tip 1252 to outer sleeve 1254, although other interconnections that permit the reamer tip 1252 to be exchanged on the outer sleeve 1254 are contemplated within the scope of this invention.

Outer sleeve 1254 is generally tubular. Outer sleeve 1254 may have one or more proximal windows 1276 and an external target such as line 1278 shown in FIG. 39.

Optional inner shaft 1256, if present, is slidably retained within outer sleeve 1254. Inner shaft 1256 comprises a depth indicator portion 1286 at or near the proximal end 1290 of inner shaft 1256. The depth indicator portion 1286 is marked with a line 1288. Inner shaft 1256 also comprises a blunt distal end 1292 that extends into the bore 1274 of the reamer tip 1252.

Torque fitting 1258 is rigidly affixed to the proximal end of the outer sleeve 1254. In the embodiment shown, the torque fitting 1258 is a shaft 1282 terminating in a quick connect tip 1284 suitable for connection to a modular handle or power driver (not shown). However, other torque fittings are contemplated, such as a square tip, hexagonal tip, threads, manual handle, or other fittings known in the art. In the embodiment shown, a proximal interior end surface 1280 of torque fitting 1258 closes the proximal end of outer sleeve 1254, although in alternate embodiments the proximal end of outer sleeve 1254 may be closed by another component part, or by an intrinsic portion of outer sleeve 1254.

Inner shaft 1256 slides between a distal limit and a proximal limit. The distal limit may occur when a protruding distal edge of depth indicator portion 1286 contacts a distal edge of proximal window 1276 on outer sleeve 1254. However, the distal limit may occur when another portion of the inner shaft 1256 contacts a portion of the base reamer 1250. When inner shaft 1256 is at its distal limit, its blunt distal end 1292 is at its closest approach to the distal end of the reamer tip 1252, and the line 1288 is distal to the target line 1278 on outer sleeve 1254. In the embodiment shown, the proximal limit occurs when the proximal end 1290 of inner shaft 1256 abuts the proximal interior end surface 1280 of torque fitting 1258. However, the proximal limit may occur when another portion of the inner shaft 1256 contacts a portion of the base reamer 1250. When inner shaft 1256 is at its proximal limit, the blunt distal end 1292 may be at a precisely controlled predetermined depth from a reference feature, such as the distal end of the reamer tip 1252, and the line 1288 may be precisely aligned with the target line 1278 on outer sleeve 1254.

Figure 40D:
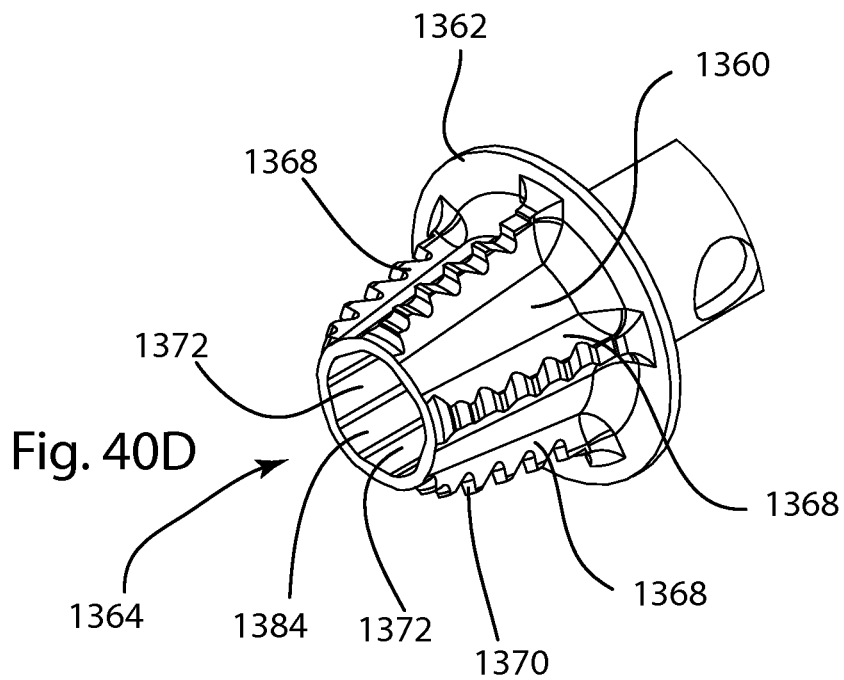
FIG. 40D is a detail view of the distal end of the base broach of FIG. 40A.
Figure 40E:
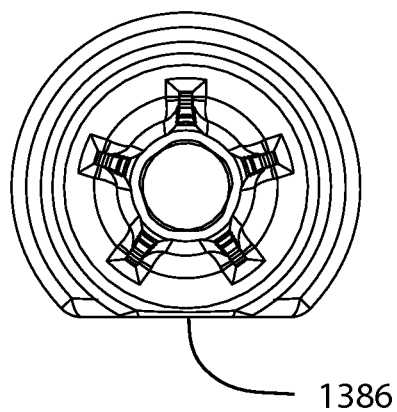
FIG. 40E is an end view of the base broach of FIG. 40A.

FIG. 40 illustrates an embodiment of a base broach 1350. The base broach 1350 comprises a replaceable broach tip 1352, an outer sleeve 1354, an optional inner shaft (not shown), and a hammer handle 1358. The base broach 1350 may cooperate with the shield described previously.

The replaceable broach tip 1352 comprises a body 1360, an optional flange 1362, a center bore 1364, and a shaft portion 1366. The body 1360 and optional flange 1362 may be configured to correspond to a particular implant base embodiment. Therefore, a set of broach tips may be provided, wherein each broach tip in the set corresponds to a different implant base configuration. The body 1360 may comprise a plurality of optional fins 1368 if the corresponding implant base has fins or other similar projections. The fins 1368, if present, may be provided with cutting features, such as teeth, serrations 1370, or blades. The optional flange 1362 forms a shelf proximally adjacent to the body 1360 and corresponding to a flanged implant base. The center bore 1364 comprises a diameter 1384 sized to slip over the proximal threaded attachment portion and shaft of any of the fixation members disclosed herein. The center bore 1364 may further comprise a plurality of flats 1372 corresponding in number to, and sized to slip over, the flats 1107 on pedicle screw 1100. In this case, the broach tip 1352 would be dedicated for use only with fixation members having a corresponding plurality of flats 1107. The shaft portion 1366 comprises an interconnection 1374 to removably connect broach tip 1352 to outer sleeve 1354, and it may be similar or identical to the shaft portion 1264 described above with regard to the base reamer 1250.

The outer sleeve 1354 is generally tubular. Outer sleeve 1354 may have one or more proximal windows 1376 and an external target such as a line (not shown) similar to line 1278 of outer sleeve 1254 of base reamer 1250. Outer sleeve 1354 may be functionally or physically similar or identical to outer sleeve 1254.

The optional inner shaft, if present, is slidably retained within outer sleeve 1354. The inner shaft may be functionally or physically similar or identical to inner shaft 1256 of base reamer 1250.

The hammer handle 1358 comprises a solid shaft 1378 between two sturdy flange portions 1380, 1382. The shaft 1378 and flange portions 1380, 1382 may be integrally formed, permanently assembled, such as by welding separate pieces, or separably assembled. In the embodiment shown, hammer handle 1358 is configured with a distal bore to rigidly affix to outer sleeve 1354. Alternatively, the hammer handle 1358 may be integrally formed with the outer sleeve 1354. At least one of the flange portions 1380, 1382 may have a feature, such as flat 1386, to indicate the orientation of any fins or other projections on the broach tip 1352.

Figure 41:
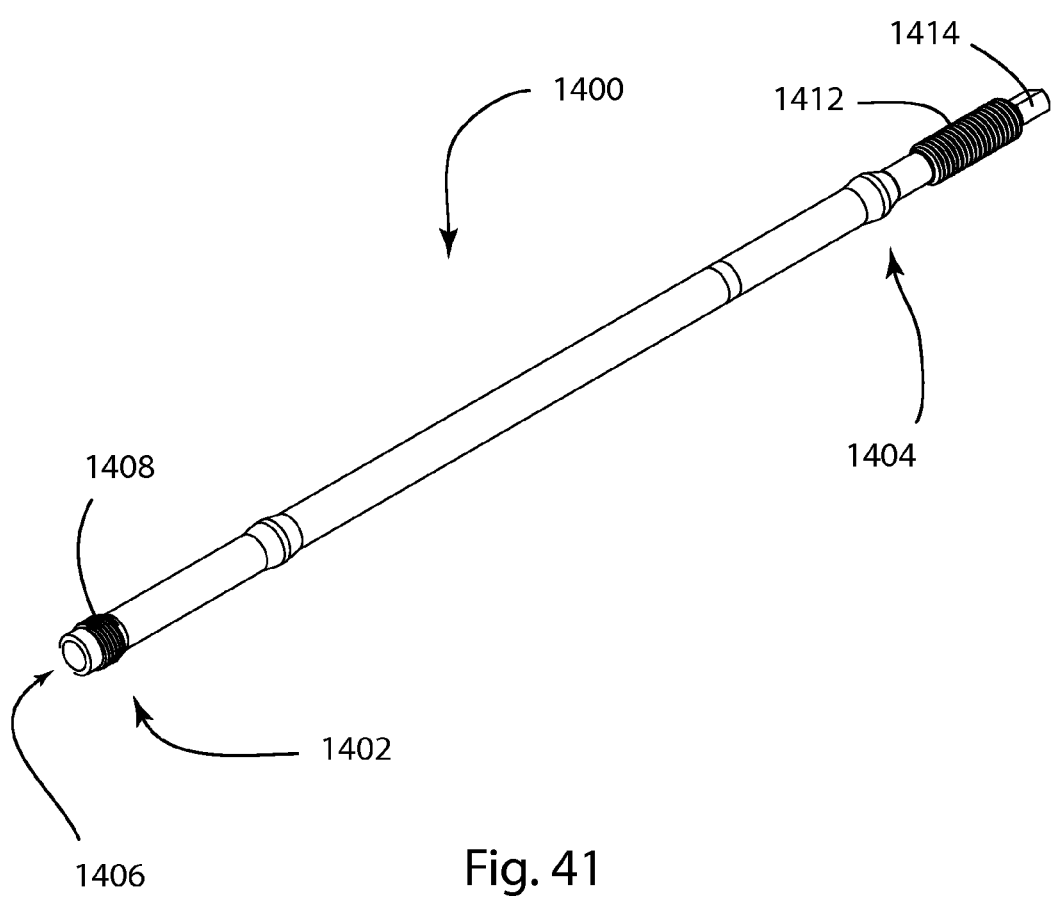
FIG. 41 is a perspective view of a base inserter.
Figures 42A, 42B, 42C:
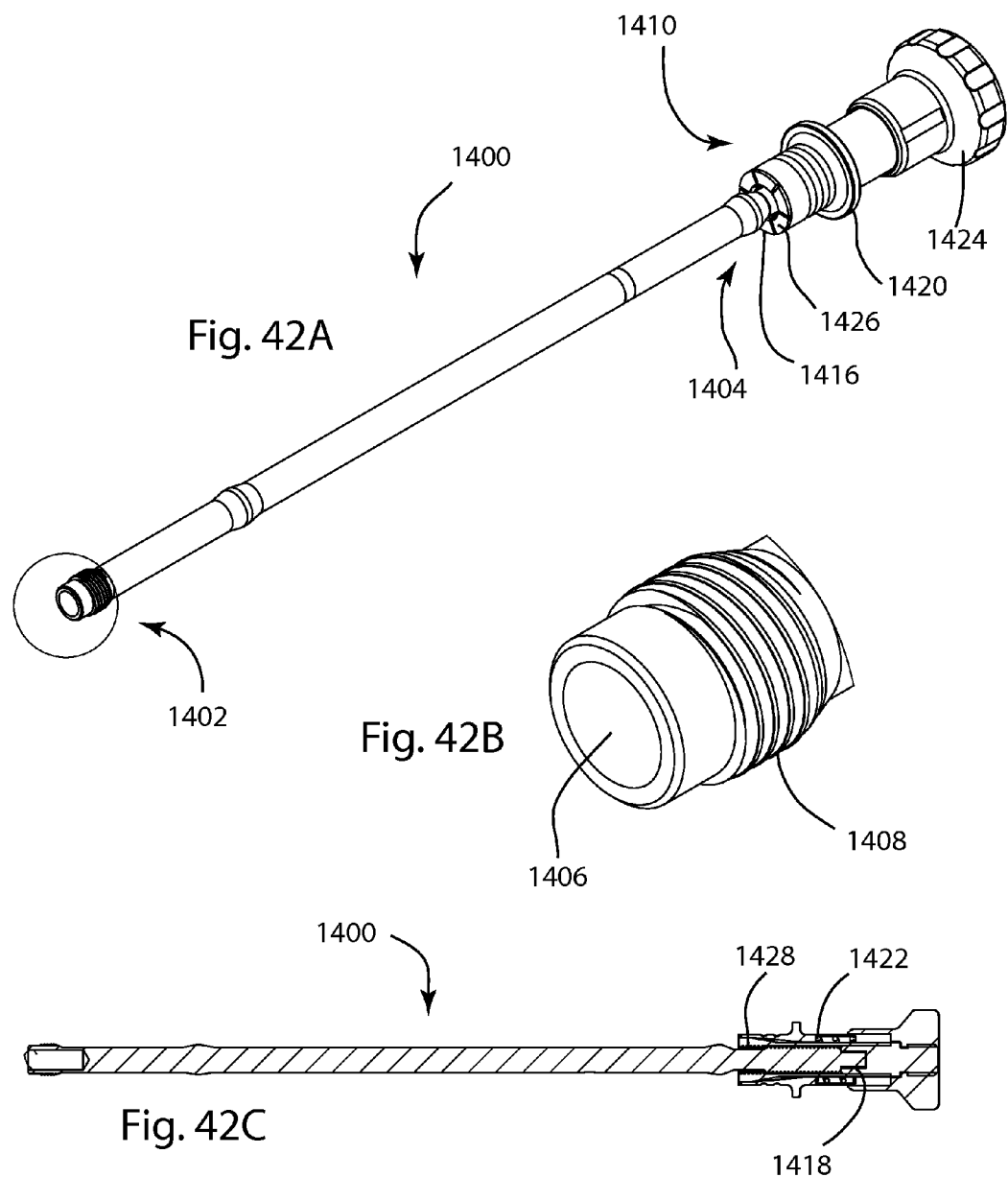
FIG. 42A is a perspective view of the base inserter of FIG. 41 coupled to a modular handle.
FIG. 42B is a detail view of the distal tip of the base inserter of FIG. 42A.
FIG. 42C is a cross-sectional view of the base inserter of FIG. 42A.

FIGS. 41-42 illustrate the base inserter 1400 alone and in combination with modular handle 1410.

In this embodiment, the base inserter 1400 comprises a monolithic shaft with a distal end 1402 and a proximal end 1404. The distal end 1402 has a bore 1406, which may comprise a precisely controlled predetermined depth, and a threaded portion 1408, whose threads cooperate with the threaded lumens of implant base 354 or 870. The proximal end 1404 comprises a threaded portion 1412 and terminates in a flattened portion 1414.

The modular handle 1410 comprises a distal collet 1416, an interior slot 1418, an outer sleeve 1420, a spring 1422, and a proximal platform 1424. Handle 1410 may be characterized as a quick connect handle because it can be attached and removed from an instrument shaft, such as base inserter 1400, faster than, for example, threading a handle onto a shaft. The collet 1416 has a plurality of prongs 1426 which flare toward the open end of the collet 1416 in the free state. The prongs 1426 have threads 1428 on their inner faces which cooperate with the threads 1412 on the base inserter 1400 when the collet 1416 is retracted within outer sleeve 1420. The collet 1416 is rigidly assembled to slot 1418, which is shaped and sized to surround and cooperate with the flattened portion 1414 on the base inserter 1400. The collet 1416 and the slot 1418 are rigidly assembled to, or integrally formed with, the platform 1424. The outer sleeve 1420 slides over the collet 1416 such that the prongs 1426 are compressed together when the collet 1416 is retracted within the outer sleeve 1420, and uncompressed when the collet 1416 extends at least partially out of the outer sleeve 1420. The spring 1422 biases the outer sleeve 1420 toward the open end of the collet 1416 so that the collet 1416 is normally compressed. The collet 1416 opens only when the outer sleeve 1420 slides toward the proximal platform 1424 against the resistance of spring 1422.

In an alternate embodiment (not shown), a base inserter may comprise a depth stop or depth indicator assembly that is functionally or physically similar or identical to the outer sleeve 1254 and inner shaft 1256 described previously with regard to the base reamer 1250.

In another alternate embodiment (not shown), a base inserter may comprise a lobed distal tip corresponding to the tool engagement rims of implant base 304, 850, 880, 890, 900, 910, 920, or 930 instead of the threads 1408 disclosed for base inserter 1400.

Figure 43:
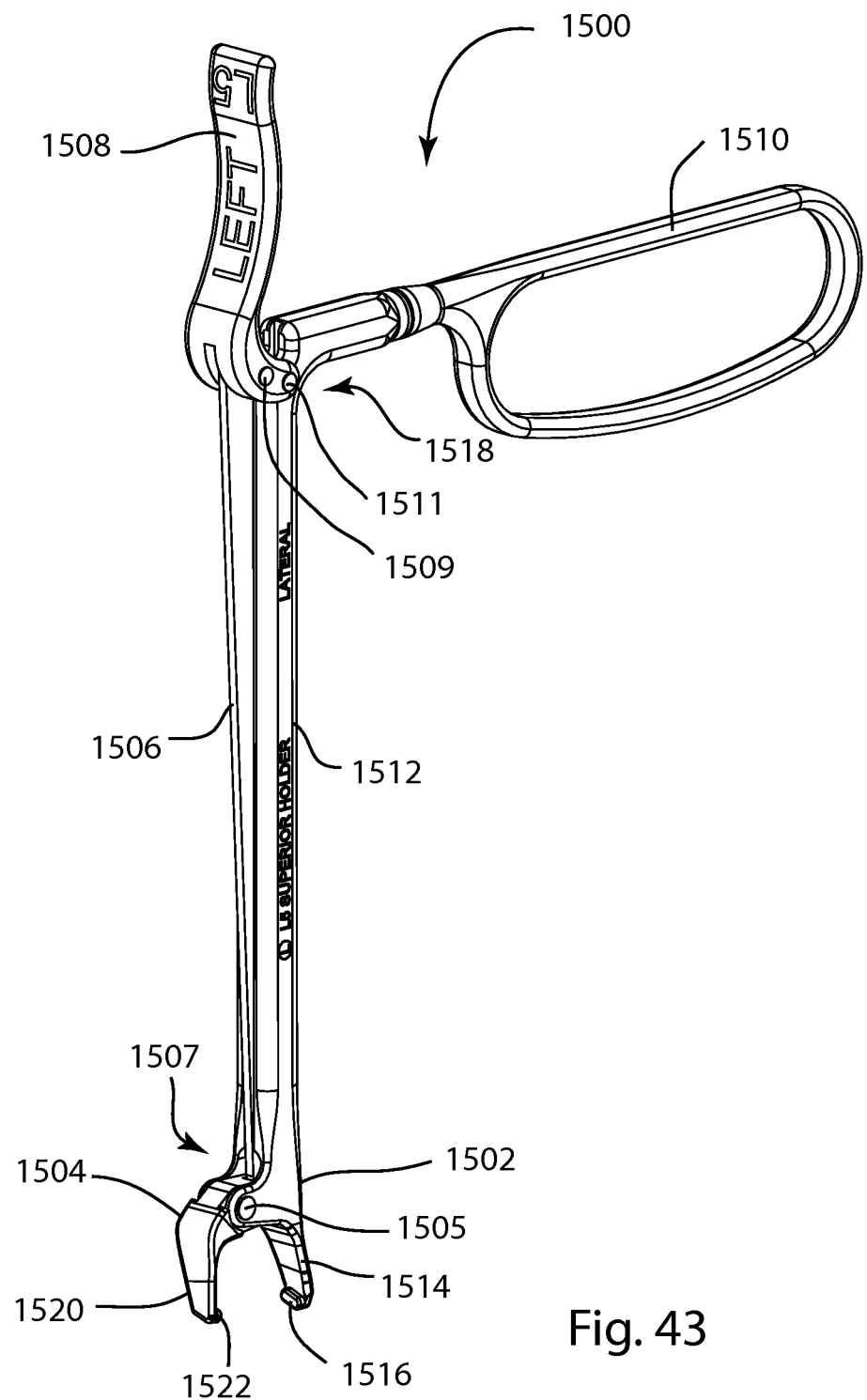
FIG. 43 is a perspective view of a superior implant inserter.

FIG. 43 illustrates an inserter 1500 for a superior facet joint implant, such as implant 210 disclosed herein. The superior inserter 1500 comprises a fixed jaw 1502, a moveable jaw 1504, a bar 1506, a lever 1508, and a handle 1510.

The fixed jaw 1502 comprises a shaft 1512, with a distal arm 1514 terminating in a tab 1516, and an elbow 1518 at the proximal end. The shaft 1512 may be grooved along at least one side, as shown. The tab 1516 is sized and shaped to fit into a first notch 206 on superior facet joint implant 210. Because the tab 1516 and notch 206 are noncircular, their engagement assures a particular orientation between the superior implant 210 and the inserter 1500. The elbow 1518 creates a visually obvious angle with respect to the shaft 1512, and may preferably be 90 degrees.

The moveable jaw 1504 is hinged to the fixed jaw 1502 between the shaft 1512 and arm 1514. The moveable jaw 1504 comprises an arm 1520 terminating in a tab 1522. The moveable jaw 1504 is hinged to the fixed jaw 1502 such that the arm 1520 is aligned opposite the arm 1514 and the tab 1522 is aligned opposite the tab 1516. The tab 1522 is sized and shaped to fit into a second notch 206 on superior facet joint implant 200 or 210. Because the tab 1522 and notch 206 are noncircular, their engagement assures a particular orientation between the implant 200 or 210 and the inserter 1500.

A first end of the bar 1506 is hinged to the moveable jaw 1504 at an end opposite the tab 1522. Furthermore, the hinge 1507 (not shown) between the bar 1506 and the moveable jaw 1504 is offset from the hinge 1505 between the moveable jaw 1504 and the fixed jaw 1502, although the two hinges may be close together. A second end of the bar 1506 is hinged to the lever 1508.

The lever 1508 is hinged to the fixed jaw 1502 at or near the elbow 1518. The lever 1508 is also hinged to the second end of the bar 1506. The hinge 1509 between the lever 1508 and the bar 1506 is offset from the hinge 1511 between the lever 1508 and the fixed jaw 1502, although the two hinges may be close together.

The handle 1510 is secured to the fixed jaw 1502 at or near a free end of the elbow 1518, such that the handle 1510 lies in the same plane as the shaft 1512 and elbow 1518. The handle 1510 extends along the angle established by the elbow 1518 with respect to the shaft 1512 so that the angle is more readily dinstinguished.

The lever 1508, bar 1506, moveable jaw 1504, and hinges 1505, 1507, 1509, 1511 cooperate to provide a mechanism that allows the surgeon to open the moveable jaw 1504 by lifting the lever 1508, and close the moveable jaw 1504 by depressing the lever 1508.

Figure 44A:
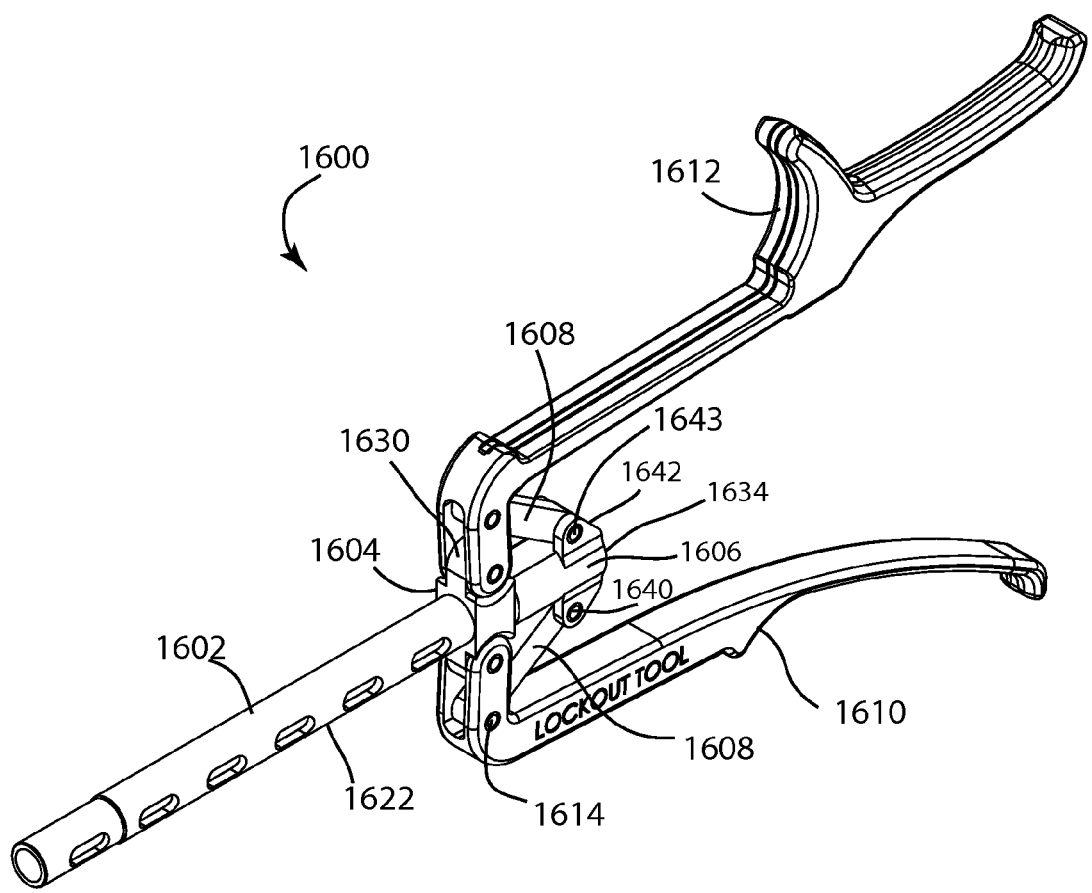
FIG. 44A is a front perspective view of a lockout tool.
Figure 44B:
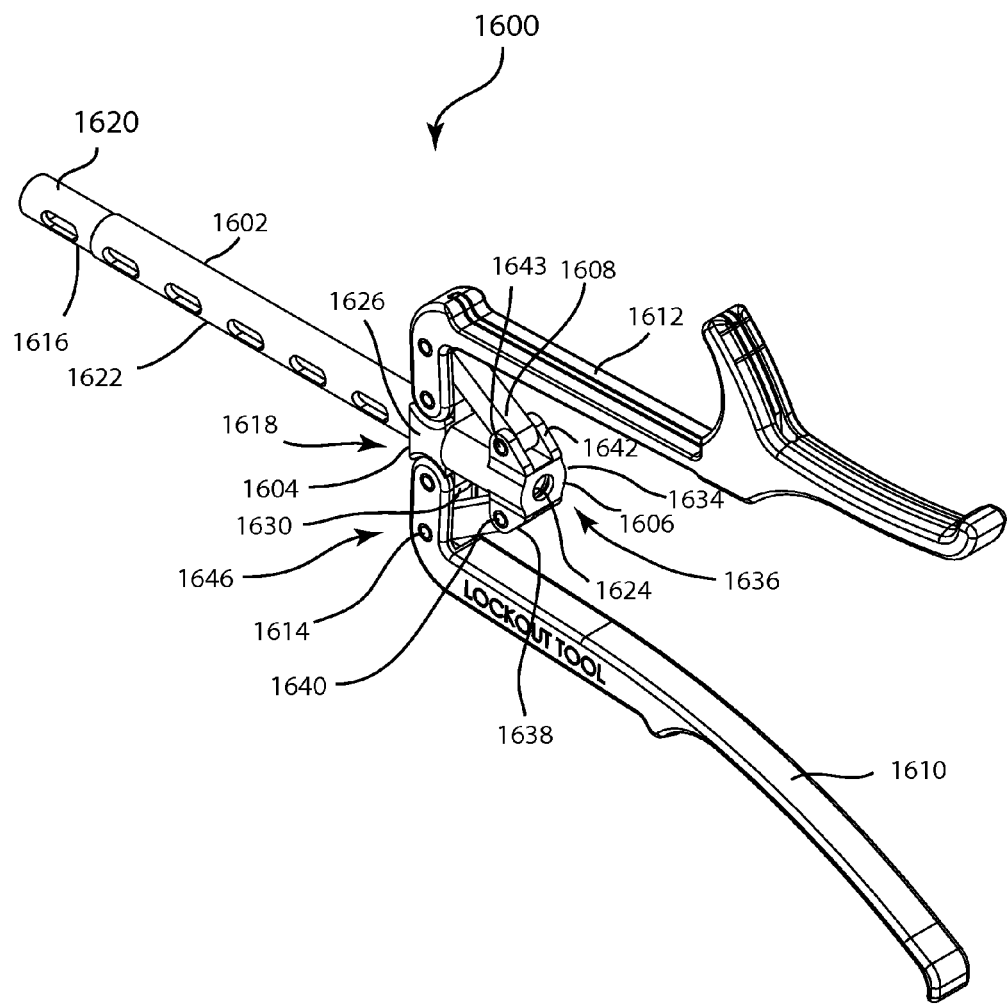
FIG. 44B is a rear perspective view of the lockout tool of FIG. 44A.

FIGS. 43-44 illustrate an embodiment of a lockout tool 1600. The lockout tool 1600 comprises a tube 1602, a hub 1604, a drive sleeve 1606, two links 1608, a first handle 1610, a second handle 1612, and six pins 1614.

The tube 1602 comprises a distal end 1616 and a proximal end 1618. The distal end 1616 may or may not have a reduced diameter 1620 compared to a midportion 1622 of the tube 1602. The proximal end 1618 has a reduced diameter 1624 compared to the midportion 1622 of the tube 1602.

The hub 1604 comprises a center body 1626 with a through hole 1628. The center body 1626 has two ears or projections 1630 that extend from opposite sides of the body. Each projection 1630 has a through hole 1632 sized to receive a pin 1614. The through holes 1632 in the projections 1630 are oriented perpendicular to the through hole 1628 in the body 1626, and parallel to each other. The hub 1604 fits over the proximal reduced diameter 1624 immediately adjacent to the midportion 1622 of the tube 1602. The hub 1604 is securely fixed to the tube 1602, or the hub 1604 may be integrally formed with the tube 1602.

The drive sleeve 1606 comprises a center body 1634 with a through hole 1636. Two ears or projections 1638 extend from one side of the body 1634. The projections 1638 are aligned with each other so as to bracket a space between them. A hole 1640 extends through both projections 1638. The hole 1640 is sized to receive a pin 1614. The hole 1640 in the projections 1638 is oriented perpendicular to the through hole 1636 in the body 1634. Two more identical projections 1642 extend from the opposite side of the body 1634 and have hole 1643 passing through them. The drive sleeve 1606 fits over the proximal reduced diameter 1624 immediately adjacent to the hub 1604. The drive sleeve 1606 is able to slide along the reduced diameter 1624.

The link 1608 in this embodiment is a flat bar with an oval profile. Each end of the link 1608 is pierced with a hole 1644 sized to receive a pin 1614. The holes 1644 are oriented perpendicular to the opposed flat faces of the link 1608 and parallel to each other. One end of a first link 1608 is hinged between projections 1638 on drive sleeve 1606 by pin 1614, and one end of a second link 1608 is hinged between projections 1642 by a second pin 1614.

The first handle 1610 is a flat, generally elongate bar with an elbow 1646 or dogleg at its distal end 1648. The elbow 1646 comprises two ears or projections 1650 that extend from the main portion of the first handle 1610. The projections 1650 are aligned with each other so as to bracket a space between them. Two holes 1652 extend through both projections 1650. The holes 1652 are sized to receive pins 1614. The holes 1652 are oriented perpendicular to the opposed flat faces of the first handle 1610 and parallel to each other. A first hole 1652, which is closer to the free end of the elbow 1646, hinges the first handle 1610 to a first projection 1630 on hub 1604 by a pin 1614. A second hole 1652, which is closer to the bend of the elbow 1646, hinges the first handle 1610 to a second end of the first link 1608. As the first handle 1610 rotates about its hinge with the hub 1604, its hinge with link 1608 rotates as well, causing the link 1608 to push or pull on its hinge with the drive sleeve 1606. Thus, rotating the first handle 1610 causes the drive sleeve 1606 to slide along the proximal reduced diameter 1624 of the tube 1602.

The second handle 1612 is also a flat, generally elongate bar with an elbow 1654 or dogleg at its distal end 1656. The second handle 1612 further comprises a projection 1658 from its midsection 1660. The elbow 1654 comprises two ears or projections 1662 that extend from the main portion of the second handle 1612. The projections 1662 are aligned with each other so as to bracket a space between them. Two holes 1664 extend through both projections 1662. The holes 1664 are sized to receive pins 1614. The holes 1664 are oriented perpendicular to the opposed flat faces of the second handle 1612 and parallel to each other. A first hole 1664, which is closer to the free end of the elbow 1654, hinges the second handle 1612 to a second projection 1630 on hub 1604 by a pin 1614. A second hole 1664, which is closer to the bend of the elbow 1654, hinges the second handle 1612 to a second end of the second link 1608. As the second handle 1612 rotates about its hinge with the hub 1604, its hinge with link 1608 rotates as well, causing the link 1608 to push or pull on its hinge with the drive sleeve 1606. Thus, rotating the second handle 1612 also causes the drive sleeve 1606 to slide along the proximal reduced diameter 1624 of the tube 1602.

The projection 1658 extends from the midsection 1660 of the second handle 1612 on the side opposite the elbow 1654. In the embodiment shown, the projection 1658 is generally arcuate. The projection 1658 is preferably spaced about a hands'-span from the proximal end 1666 of the second handle 1612. The second handle 1612 may also comprise an integral plate 1668. If present, the plate 1668 is located between the opposed flat faces of the second handle 1612. The plate 1668 may extend from the distal end 1656 to a point just past the projection 1658. The plate 1668 is separated from the rest of the second handle 1612 by a slot 1670 which borders three sides of the plate 1668 so that the plate connects to the second handle 1612 only at the distal end 1656. The slot 1670 is cut parallel to the opposed flat faces of the second handle 1612. The plate 1668 serves a passive role as an indicator of the force applied to the first and second handles 1610, 1612 of the lockout tool 1600. As the user grips the handles 1610, 1612 with increasing force, the handles 1610, 1612 will deflect proportionately. The plate 1668 is subject to no force and therefore experiences no deflection. As the handle 1612 deflects, it appears as though plate 1668 emerges from its slot 1670 in handle 1612, particularly at projection 1658. The deflection of handle 1612 may be calibrated so that a first line 1670 marked across plate 1668 and projection 1658 aligns with a second line 1672 marked across projection 1658 when an appropriate grip force has been applied to the handles 1610, 1612.

Figure 45:
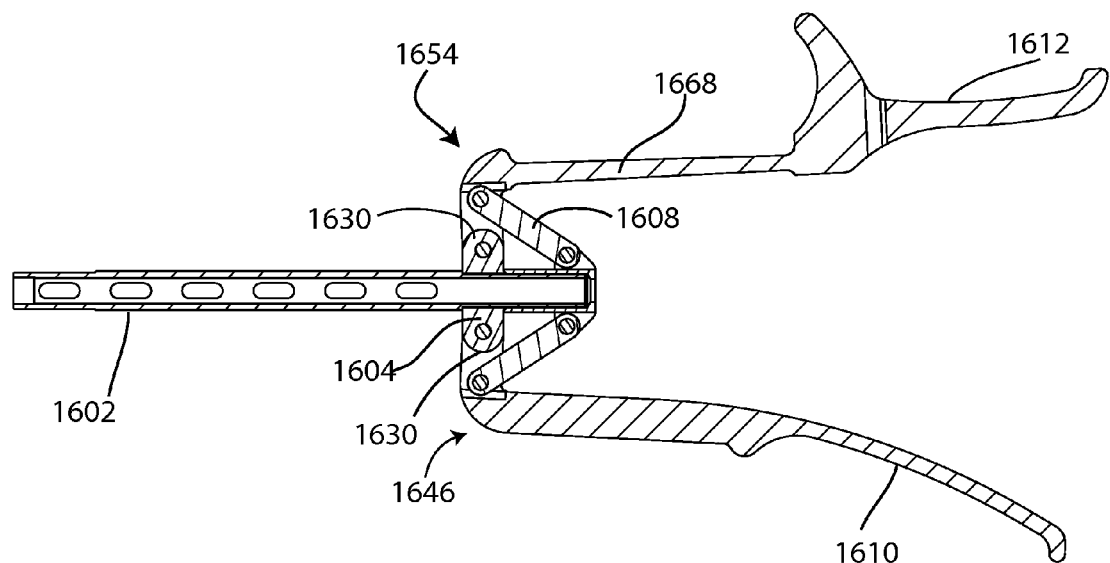
FIG. 45 is a cross-sectional view of the lockout tool of FIG. 44.

FIGS. 45-46 illustrate an embodiment of an inferior trial assembly 1700. Inferior trial 1700 comprises a trial strut 1702, a trial sphere 1704, a trial shell 1708, a trial ball 1706, and a retaining ring 1710. Inferior trial 1700 substantially mimics inferior facet joint implant 100 (FIGS. 1-6).

The trial strut 1702 substantially mimics the inferior strut 104 of inferior facet joint implant 100. The trial strut 1702 is generally elongated, with a central portion 1740, a first end which is a ring 1742, and a second end which is a strut post 1744. The central portion 1740 may be shaped to smoothly transition from the ring 1742 to the strut post 1744, and may be straight, bent or curved. The ring 1742 may be a generally circular feature with a center point 1746 and opposed end faces 1748 which are substantially planar and parallel. The ring 1742 may be set at an angle relative to the central portion 1740 or the strut post 1744. The strut post 1744 may be a generally cylindrical feature with a center axis 1750. The strut post 1744 may have a groove 1752 at or near its free end. The strut post 1744 may be at an angle relative to the central portion 1740 and the ring 1742. A kit of trials struts may be provided, wherein each trial strut corresponds to a matching inferior implant strut.

More precisely, each trial strut may be constructed so that the tip of the strut post is offset from the center point of the ring by one or more of the X2 offset, the Y2 offset, and the Z2 offset described previously with regard to the inferior implant strut 104

The trial sphere 1704 substantially mimics the split spheres 306 or 356 shown in FIGS. 5-10. The trial sphere 1704 is sized to fit over the tapered portion of an implant base, and may have a tapered inner wall 1756. The inner wall 1756 may alternatively comprise one or more discrete diameters. The trial sphere 1704 may also have a flange 1754 which encircles one open end of the trial sphere 1704. The trial sphere 1704 lacks any slits, and is therefore not expandable like the split spheres 306 or 356. The trial sphere 1704 is polyaxially mobile within the ring 1742 of the trial strut 1702 in the same way that split spheres 306 or 356 engage the ring 182 of the inferior strut 104.

The trial shell 1708 comprises an articular body portion 1722 that substantially mimics the inferior articular body 102 shown in FIGS. 1-4. Trial shell 1708 also incorporates a clip portion 1724 which is similar to clip 550 shown in FIGS. 12-14 or clip 1200 shown in FIGS. 23-25.

The articular body portion 1722 has a substantially concave interior cavity 1712 which is defined by an interior wall 1714. A first chamfered opening 1716 and a second chamfered opening 1718 in the articular body portion 1722 create a passageway through which a portion of the trial strut 1702 may fit when the inferior trial 1700 is assembled. A third opening 1720, which may also be chamfered, is situated orthogonal to the first and second chamfered openings 1716, 1718. The chamfered openings 1716, 1718, 1720 may provide additional range of motion between the trial shell 1708 and the trial strut 1702 as the trial shell 1708 is polyaxially adjusted to fit the patient's anatomy. A trial inferior articular surface 1722 is located on the exterior of the articular body portion 1722, and is shaped like inferior articular surface 122 of inferior facet implant 100. However, trial inferior articular surface 1722 may be offset, or recessed into the articular body portion 1722, compared to inferior articular surface 122.

The clip portion 1724 comprises a body 1726, which is connected to the articular body portion 1722 between the third opening 1720 and the trial inferior articular surface 1722, and a pair of parallel pins 1728 which extend beside the trial inferior articular surface 1722. The body 1726 may be integrally formed with the articular body portion 1722. The body 1726 forms a collar 1734 surrounding a hole 1730, which may be substantially parallel to the pins 1728. The hole 1730 may extend through the body 1726, and may step down to a smaller diameter 1732 at the end closest to the pins 1728. At the same end, the collar 1734 may flare into a platform 1736 to which the pins 1728 are connected. The pins 1728 may be integrally formed with the platform 1736. The pins 1728 may step down to a smaller diameter 1738 at their free ends.

The trial ball 1706 substantially mimics the attachment mechanism 106 shown in FIGS. 1-4. More specifically, the trial ball 1706 mimics the functions of the conical expander 126 and split shell 128. The trial ball 1706 comprises a sphere 1758 with a blunt post 1760 extending from the sphere 1758. The sphere 1758 has a through hole 1762 through its center and perpendicular to the post 1760. The sphere 1758 may also have a slit 1764 which is on the side opposite the post 1760 and which extends the length of the hole 1762. The trial ball 1706 is polyaxially mobile within the cavity 1712 of the trial shell 1708 in the same way that conical expander 126 and split shell 128 engage the cavity 112 of the inferior articular body 102. The sphere 1758 fits inside the cavity 1712, the post 1760 extends through the third opening 1720, and the hole 1762 slides over the strut post 1744.

The retaining ring 1710 is circular with a gap 1766. The retaining ring 1710 fits snugly in the groove 1752 on the trial strut 1702. The retaining ring 1710 prevents the trial ball 1706 and trial shell 1708 from sliding off the free end of the strut post 1744 after the inferior trial 1700 has been assembled.

Figure 47:
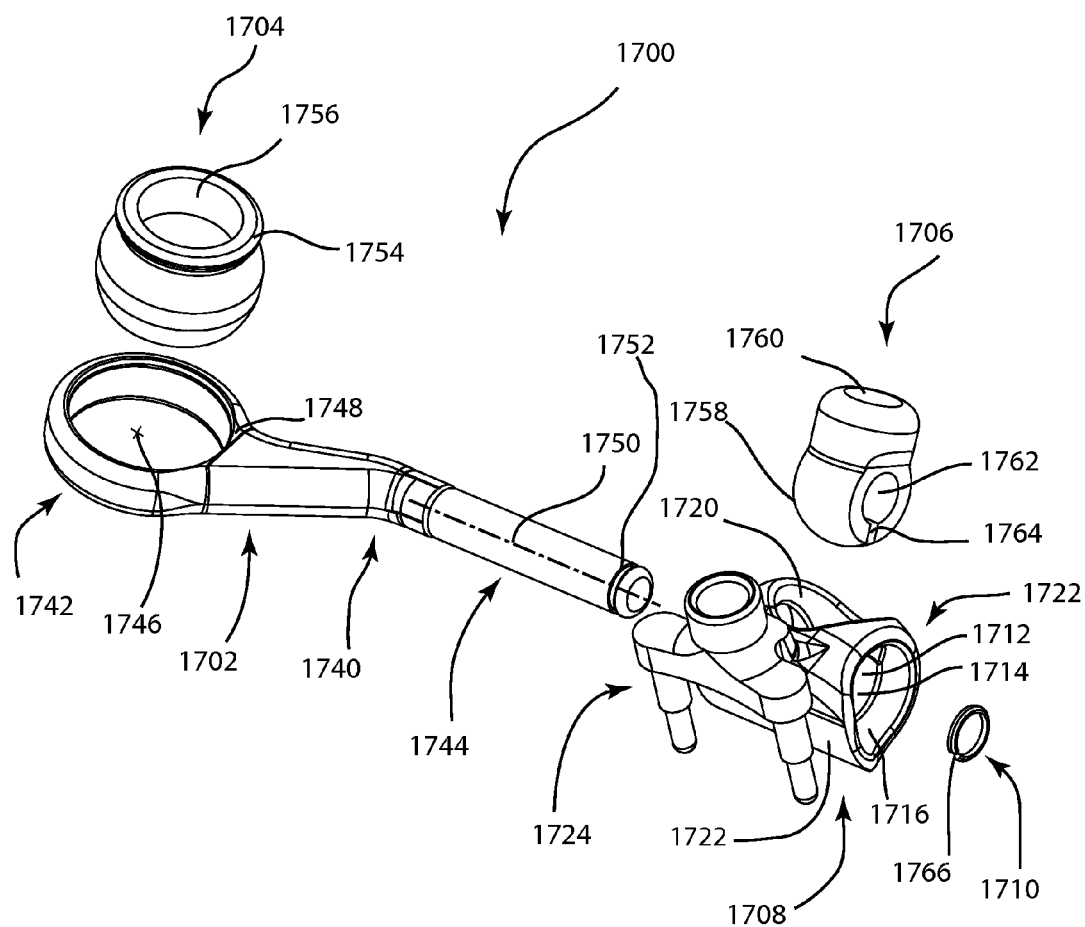
FIG. 47 is an exploded view of the inferior trial of FIG. 46.
Figure 48A:
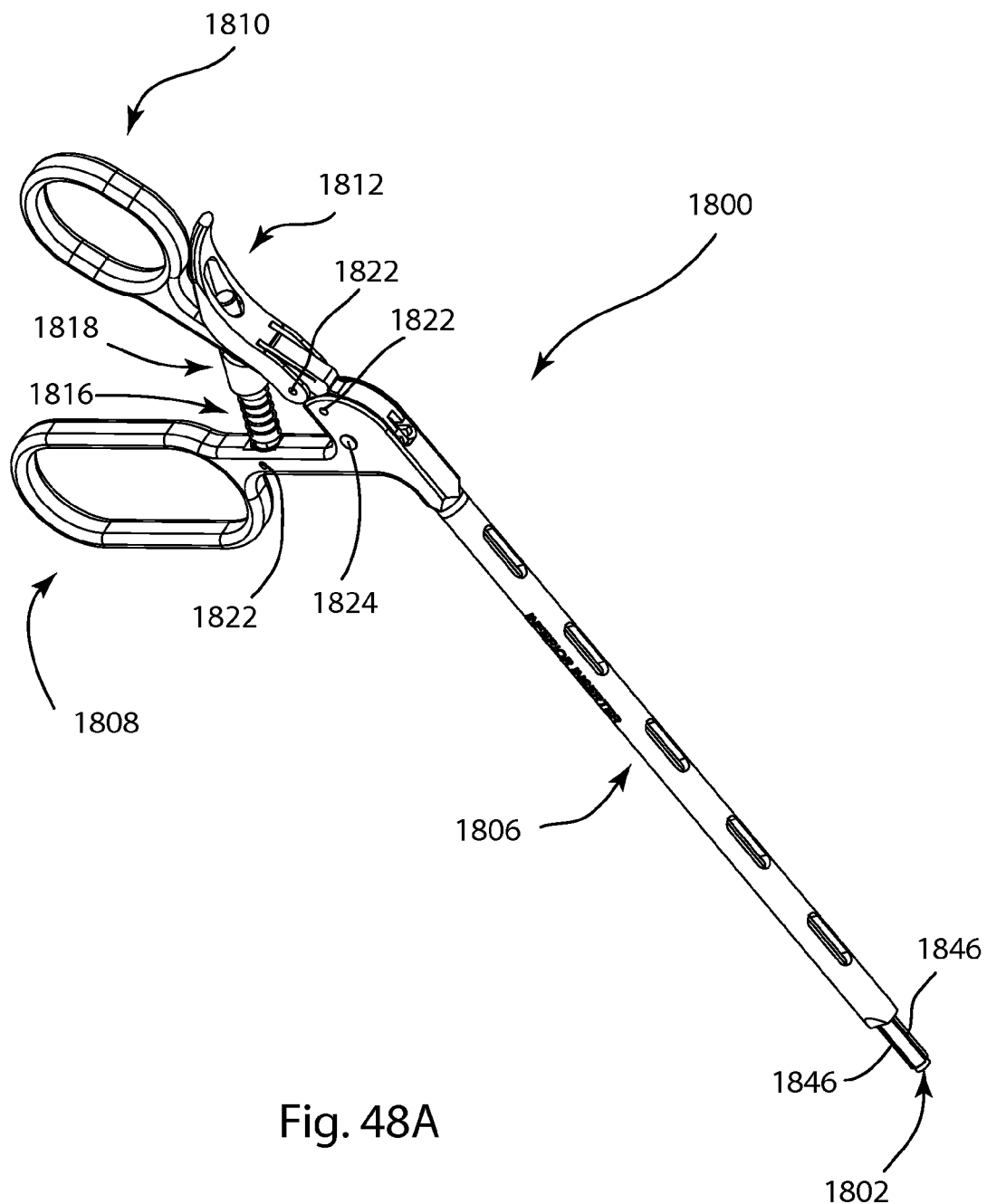
FIG. 48A is a perspective view of an inferior inserter.
Figure 48B:
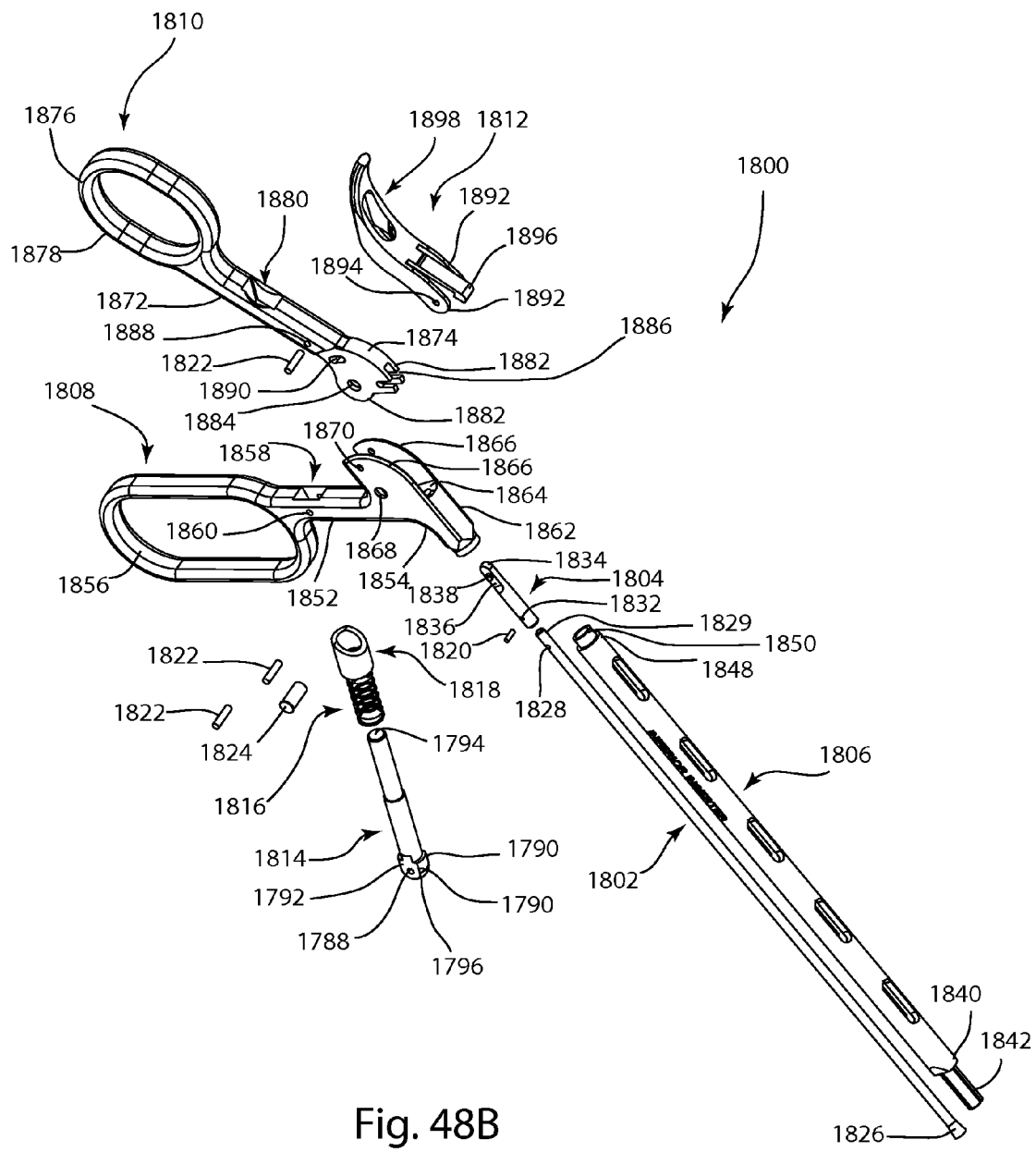
FIG. 48B is an exploded view of the inferior inserter of FIG. 48A.

A first embodiment of an inferior inserter 1800 is shown in FIGS. 47-48. The inferior inserter 1800 comprises an inner shaft 1802, a follower shaft 1804, an outer sleeve 1806, a fixed handle 1808, a movable handle 1810, a lever 1812, a rod 1814, a spring 1816, a collar 1818, a small pin 1820, three medium pins 1822, and a large pin 1824.

The inner shaft 1802 is generally cylindrical with a flared distal end 1826 and a cross hole 1828 through a proximal end 1829.

The follower shaft 1804 is generally cylindrical with a distal socket 1830 and cross hole 1832, and a proximal tab end 1834 with opposing flat faces 1836. Each proximal face 1836 has a cylindrical prong 1838 extending from it. Alternatively, a separate pin may be secured through the tab end 1834 so that the pin extends from the flat faces 1836. The socket 1830 is sized to receive the proximal end 1829 of the inner shaft 1802. The follower shaft 1804 is fixed to the inner shaft 1802 by passing a small pin 1820 through the cross holes 1828, 1832.

The outer sleeve 1806 is generally tubular and may be windowed. The distal end 1840 has a reduced diameter tip 1842 which is split into four prongs 1844 by four slots 1846. The inside diameter of the outer sleeve 1806 flares toward the distal end 1840. The proximal end 1848 of the outer sleeve 1806 may also have a reduced diameter 1850, which may be different from the distal tip diameter 1842. The inside diameter of the outer sleeve 1806 may step up to a larger diameter at a location proximal to the reduced-diameter distal tip 1842. The outer sleeve 1806 slides over the inner shaft 1802. The flared inside diameter of the distal tip 1840 of the outer sleeve 1806 fits over the flared distal end 1826 of the inner shaft 1802.

The fixed handle 1808 comprises an arm 1852 with an elbow 1854 at a first end. A second end of the arm 1852 may terminate in a loop 1856 sized to fit one or more fingers or the whole hand. The arm 1852 has a window 1858 through its midsection, in a direction generally parallel to the free end of the elbow 1854. The arm 1852 has a cross hole 1860 which passes across the window 1858. The free end of the elbow 1854 comprises a collar 1862 with a through hole 1864 sized to receive the proximal end 1848 of the outer sleeve 1806. The through hole 1864 may step up to a larger diameter at its distal end. The elbow 1854 may preferably comprise an angle near 90 degrees. Two ears or projections 1866 extend from the obtuse side of the elbow 1854, generally parallel to the collar 1862. The projections 1866 are aligned with each other so as to bracket a space between them. Two parallel holes 1868, 1870 extend through the projections 1866. The fixed handle 1808 is rigidly attached to the outer sleeve 1806. Alternatively, the handle and the outer sleeve 1806 may be made as a single part.

The movable handle 1810 comprises an arm 1872 with an enlarged, flattened first end 1874. A second end 1876 of the arm 1872 may terminate in a loop 1878 sized to fit one or more fingers or the whole hand. The arm 1872 has a window 1880 through its midsection, in a direction generally parallel to a plane established by the first end 1874. A terminal portion of the first end 1874 is divided into two ears or projections 1882 which are aligned with each other so as to bracket a space between them. A through hole 1884 and an open-ended slot 1886 pass through both projections 1882. The first end 1874 of the arm 1872 also has a through hole 1888 and slot 1890 located between the window 1880 and the projections 1882. The first end 1874 of the movable handle 1810 slides between the projections 1866 on the fixed handle 1808. The movable handle 1810 is pivotally attached to the fixed handle 1808 by passing the large pin 1824 through the hole 1890 and the hole 1868. A medium pin 1822 passes through the hole 1870 and the slot 1890 to limit the pivotal motion of the movable handle 1810. The projections 1882 on the movable handle 1810 slide over the tab end 1834 of the follower shaft 1804 and the open-ended slot 1886 receives the prongs 1838 or pin ends of the follower shaft 1804. This arrangement turns pivotal movement of the movable handle 1810 into linear movement of the follower shaft 1804 and inner shaft 1802 within the outer sleeve 1806.

The lever 1812 may be generally arcuate. A first end of the lever 1812 is divided into three projecting tabs. The first two tabs 1892 are parallel and aligned with each other so as to bracket a space between them. A hole 1894 passes through both tabs 1892 near their free ends. The third tab 1896 is perpendicular to the first two tabs 1892, and extends beside the first two tabs 1892 so that the three tabs form a three-sided, slotted channel. The midportion of the lever 1812 has a window 1898 oriented generally parallel to the first two tabs 1892. The edge of the window 1898 closest to the tabs may have serrations 1798, threads, or other tooth-like features. The first two tabs 1892 of the lever 1812 slide over the arm 1872 of the movable handle 1810 so that the lever 1812 may be pivotally attached to the movable handle 1810 by passing a medium pin 1822 through the hole 1894 and the hole 1888. The third tab 1896 rests against the arm 1872 between the window 1880 and the first end 1874. In this arrangement, the third tab 1896 may function as an intrinsic spring that biases the lever 1812 to lie against the movable handle 1810.

The rod 1814 is generally cylindrical. The outside diameter of the rod 1814 may step down one or more times from a first end 1796 to a second end 1794. The first end 1796 comprises a tab 1792 with opposing flat faces 1790. A through hole 1788 pierces the flat faces 1790 of the tab 1792. The first end 1796 of the rod 1814 is sized and shaped to slide into the window 1858 in the arm 1852 of the fixed handle 1808 so that the rod 1814 may be pivotally attached to the fixed handle 1808 by passing a medium pin 1822 through the hole 1788 and the hole 1860. The second end 1794 of the rod 1814 is sized and shaped to slide into the window 1880 in the arm 1872 of the movable handle 1810 and further into the window in the midportion of the lever 1812. The rod 1814 fits into the windows 1858, 1880, 1898 with clearance over the full range of motion of the movable handle 1810.

The spring 1816 is sized to slide over all but the largest outside diameter of the rod 1814. In the free state, the spring 1816 may be approximately the same length as the rod 1814.

The collar 1818 is generally tubular. A first end 1786 of the collar 1818 may be angled to correspond to a facing surface on the arm of the movable handle 1810. The inside diameter of the collar 1818 may step up from the first end 1786 to a second end 1784 of the collar 1818. The entire collar 1818 slides over the second end 1794 of the rod 1814 and the second end 1784 of the collar 1818 slides over at least a portion of the spring 1816. When the inferior inserter 1800 is fully assembled, the spring 1816 and collar 1818 are positioned between the fixed handle 1808 and the movable handle 1810, with the first end of the collar 1818 against the arm 1872 of the movable handle 1810. The rod 1814, spring 1816, and collar 1818 act together to bias the movable handle 1810 away from the fixed handle 1808.

Figure 49A:
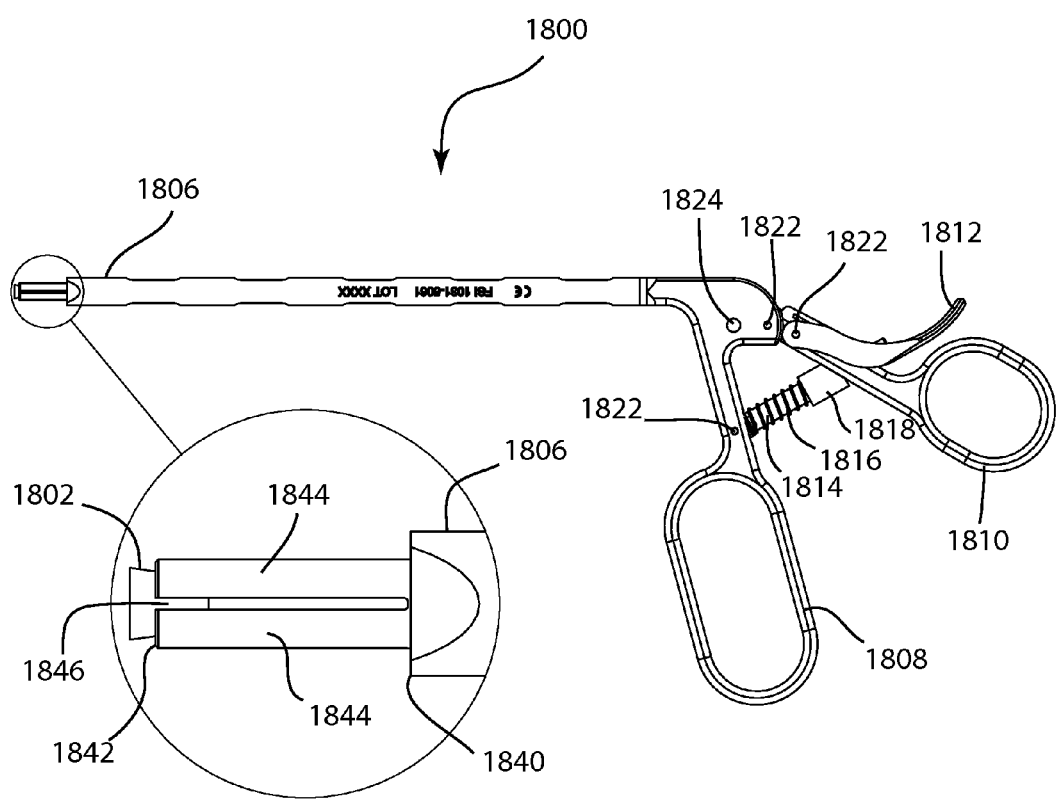
FIG. 49A is a side view of the inferior inserter of FIG. 48.
Figure 49B:
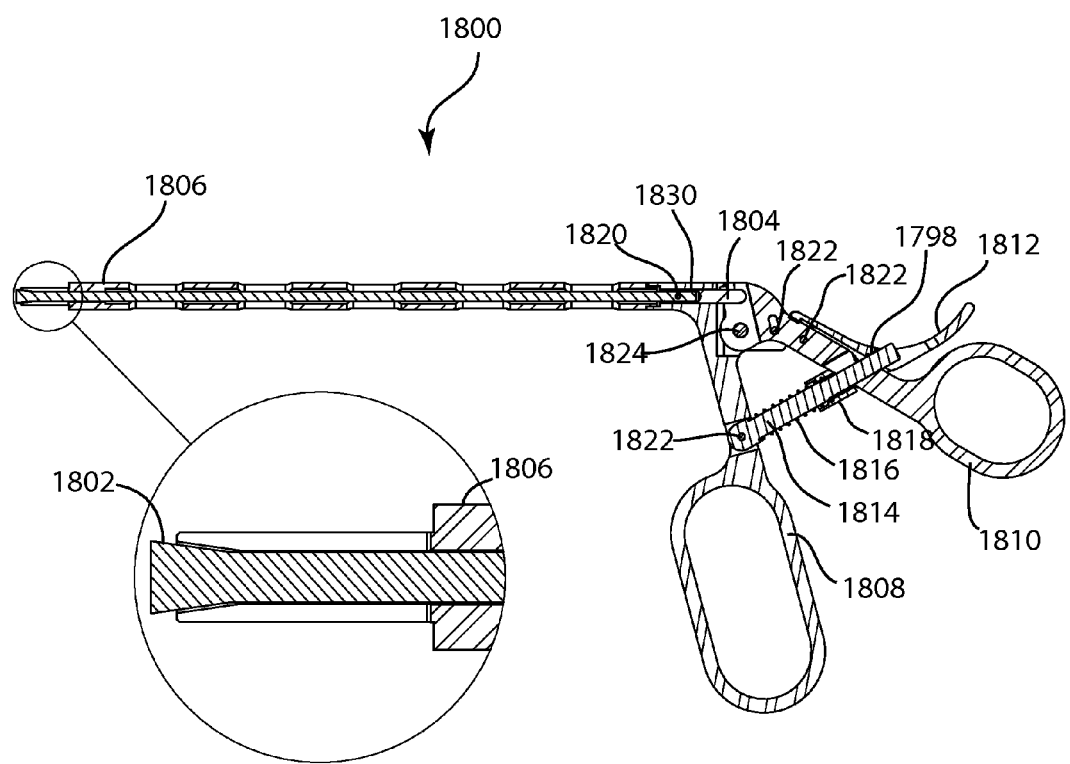
FIG. 49B is a cross-sectional view of the inferior inserter of FIG. 48.
Figure 50:
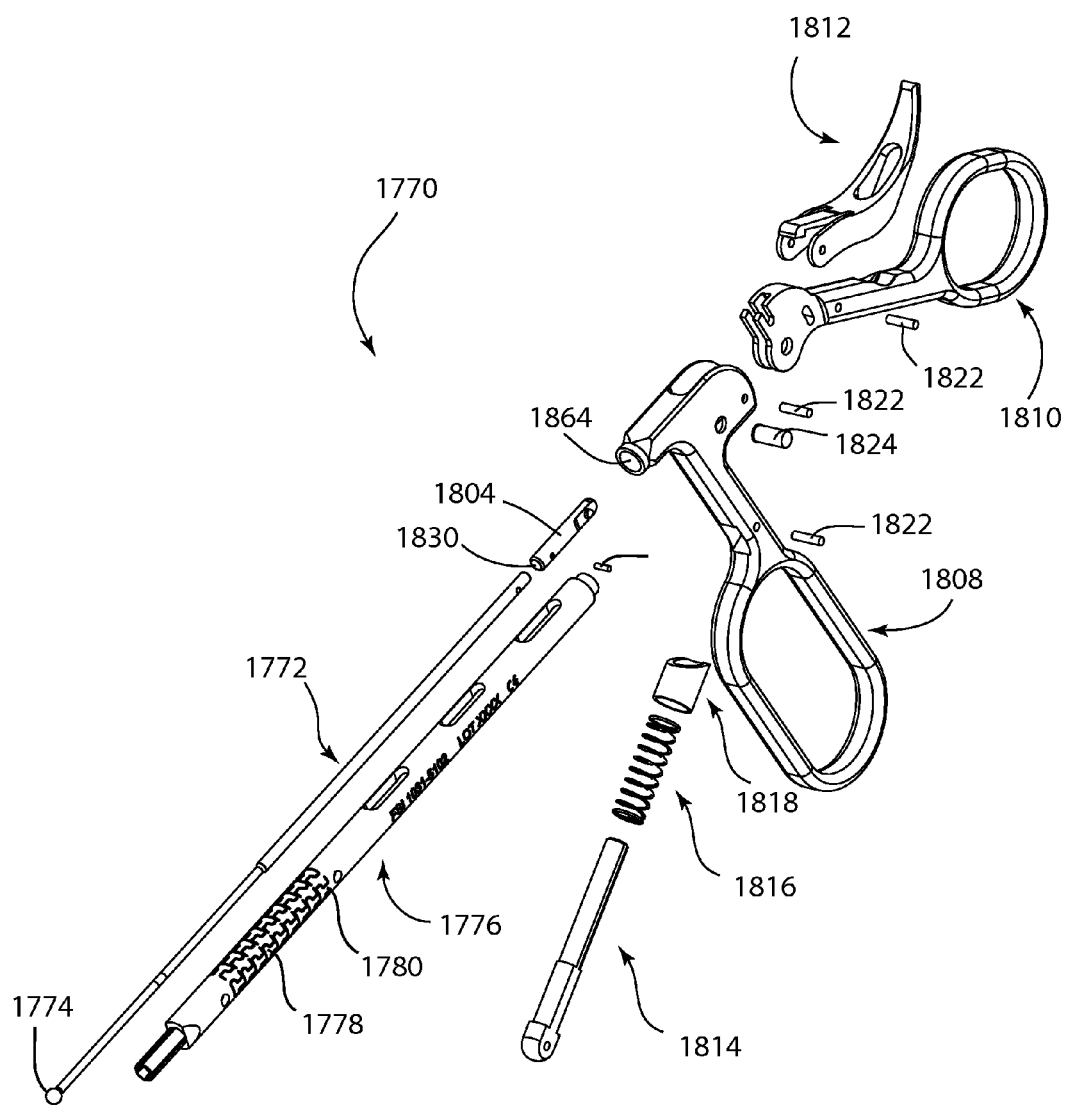
FIG. 50 is an exploded view of an alternate embodiment of an inferior inserter.

A second embodiment of an inferior inserter 1770 is shown in FIG. 49. This embodiment may differ from the first inferior inserter 1800 in that it has a flexible inner shaft 1772 and a flexible outer sleeve 1776. The remaining components may be identical to those disclosed for the first inferior inserter 1800.

The flexible inner shaft 1772 is generally cylindrical with a spherical distal end 1774 and a cross hole 1828 through a proximal end 1829. The outer diameter of the inner shaft 1772 may neck down to a smaller diameter from the proximal end 1829 to the distal end 1774 in order to increase the flexibility of the inner shaft 1772. The inner shaft 1772 may be made from any known flexible material, such as titanium, nitinol, or other superelastic alloy.

The flexible outer sleeve 1776 is generally tubular and may differ from the outer sleeve 1806 in that at least a portion of the outer sleeve 1776 has a pattern of interlocking tabs 1778 separated by slots 1780 which enhance the flexibility of the outer sleeve 1776.

Inferior inserter 1770 may be particularly useful at certain spinal levels, such as the lumbosacral level, because the inferior inserter 1770 may flex to avoid obstacles such as bony or soft tissue anatomy. The inferior inserter 1770 may also be useful in minimally invasive surgical procedures due to its flexibility.

Returning to FIGS. 1 and 22, the fixation assembly 300 and superior implant 200 may be implanted into the left pedicle of vertebra 2 as follows. It is understood that steps may occur in the order presented, or in a different sequence. It is further understood that right and left facet joint replacements may be implanted during the same procedure and optionally linked via a crosslink. The pedicle is prepared for implantation, which may include removal of natural facet surfaces and bone preparation, and may include a broaching step to shape the pedicle to receive the implant base 304. Broaching may ensure bone ingrowth and better mechanical retention of the base and therefore the full implant system. The fixation member 302 is driven into the pedicle to a prescribed or desired depth. A tapered base 304 is placed on the fixation member 302, and the bone engaging portion may be urged into the bone by pressing, tapping, or other means. A split sphere 306 is placed on the base 304, and the ring 204 of the superior implant 200 is placed over the split spheres 306 and locked down relative to the fixation assembly 300. Alternatively, the split sphere 306 may be captured in the ring 204 of the superior implant 200, and the implant/ring assembly placed on the base 304 and locked down. A second fixation assembly 300 and superior implant 210 may be implanted into the right pedicle of vertebra 2 in a similar manner.

Referring to FIGS. 23-25, the fixation assembly 350 and superior implant 210 may be implanted into the left pedicle of vertebra 2 as described above for fixation assembly 300 and superior implant 200, with the following differences. To lock the orientation and position of the superior implant 210, a lockout tool (not shown) is actuated to effect the taper lock. The lockout tool has an externally threaded inner shaft tip which is engaged in the threaded lumen 366 of the tapered base 354. The lockout tool is actuated, using tensile force to simultaneously pull on the tapered base 354 with the inner shaft, and push on the flange 368 of the split sphere 356 with an outer shaft. This force moves the split sphere 356 farther onto the tapered portion 364. The split sphere 356 expands and engages the ring 212 of the superior implant 210 until all motion ceases and the position of the ring 212 is locked down.

The lockout tool is unthreaded and removed, and the capture nut 358 is threaded into the threaded lumen 366, also capturing the flange 368 of the split sphere 356. The capture nut 358 is included to ensure the long-term integrity of the lock. The top nut 360 is threaded onto the fixation member 352, and assists in holding the tapered base 354, split sphere 356, superior implant 210, and capture nut 358 against the bone surface. The top nut 360 and capture nut 358 may use the same driver. A second fixation assembly 350 and superior implant 210 may be implanted into the right pedicle of vertebra 2 in a similar manner.

Referring to FIG. 1, fixation assembly 300 may be implanted into each pedicle of vertebra 4 in the same manner described above for vertebra 2. The pedicles are prepared for implantation, which may include removal of natural facet surfaces and bone preparation, and may include a broaching step to shape the pedicles to receive the implant bases 304. Broaching may ensure bone ingrowth and better mechanical retention of the bases and therefore the full implant system. Fixation members 302 are driven into the pedicles to a prescribed or desired depth. Tapered bases 304 are placed on the fixation members 302, and the bone engaging portions may be urged into the bone by pressing, tapping, or other means. Alternatively, fixation assembly 350 may be implanted into each pedicle of vertebra 4 in the same manner described above for fixation assembly 300.

Next, the components of inferior implant 100 are assembled but not yet locked together. A split sphere 306 is captured in the ring 182 of the strut 104, and the inferior implant/sphere assembly is placed on the tapered portion 320 of the base 304 in the left pedicle of cephalad vertebra 4. An offset distance between the inferior articular surface 122 and the fixation assembly 300 may be adjusted by moving the inferior articular body 102, with attachment mechanism 106 contained within it, relative to the inferior strut 104. At this point, the inferior articular surface 122 may be aligned with the superior articular surface 202 of superior implant 200, and may be temporarily clipped to the superior articular surfaces 202 to maintain the alignment. The inferior implant/sphere assembly is then locked down to the fixation assembly 300. In a similar manner, the components of inferior implant 101 may be assembled, adjusted, and locked down to the fixation assembly 300 in the right pedicle of cephalad vertebra 4.

The inferior articular body 102 may be packaged with superior implant 200, such that the articular surfaces 122, 202 are temporarily clipped together in a desired alignment. In this instance, the inferior articular body 102 is inserted with the superior implant 200 when the superior implant 200 is placed and locked with the fixation assembly 300. Then the inferior strut 104 and the remaining components of the inferior implant 100, including the conical expander 126, split shell 128, and split clamp 110 are assembled with the inferior articular body 102. The ring 182 of the inferior strut 104 is assembled with a split sphere 306 and locked down with the inferior fixation assembly 300. After insertion of the crosslink rod 108 and final lockdown, as described below, the temporary clip is removed.

Alternatively, the inferior implant 100 may be made available secured to a clip. The implant 100, with the attached clip, may be inserted adjacent to an already implanted and locked down superior implant, and the inferior and superior implants temporarily clipped together. The inferior strut is adjusted and locked down to its fixation assembly. After insertion of the crosslink rod 108 and final lockdown of the inferior implant, as described below, the clip is removed.

Referring to FIG. 5, the clip 550 or gripping tool may be used as a handle to place the inferior implant articular body 470 with attached strut adjacent to an implanted superior implant 210 such that posts or pins on the clip 550 engage in openings on the superior implant 210, and the inferior and superior articulation surfaces are aligned. Then the inferior strut is polyaxially adjusted and locked to a fixation assembly (not shown) in a manner similar to that described above. A crosslink may be used to connect bilateral inferior implants, as described above. As the final step, the clip 550 is unlocked and removed, allowing articulation between the inferior and superior implants along their respective articular surfaces.

The crosslink 108 may now be inserted through the collar 164 of the split clamp 110 of one inferior implant 100 or 101 and optionally through a prepared spinous process, and through the other collar 164 on the remaining inferior implant 100 or 101. It is appreciated that as the crosslink 108 is inserted, the split clamp 110 is rotatable about the clamp axis 111. Therefore, the crosslink 108 may be positioned to pass through a spinous process, or may pass through soft tissue caudal to the spinous process. Alternatively, the crosslink 108 may be inserted before the inferior implants are locked down to the fixation assemblies. The attachment mechanisms 106 of each inferior implant 100, 101 are actuated to lock down the implants, fixing the positions of the articular surfaces 122, the inferior struts 104 and the crosslink 108 relative to their respective fixation assemblies 300. Post-operatively, the articular surfaces will be capable of articulating against one another, allowing a level of natural spinal motion.

Figure 7:
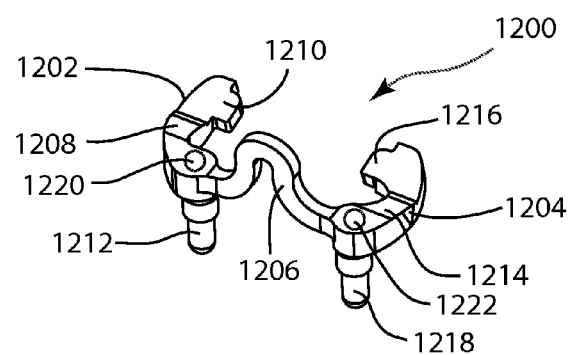
FIG. 7A is a perspective view of an alternate embodiment of a clip.
FIG. 7B is a perspective view of the clip of 7A coupled to an alternate embodiment of an inferior facet joint implant.
Figure 7:
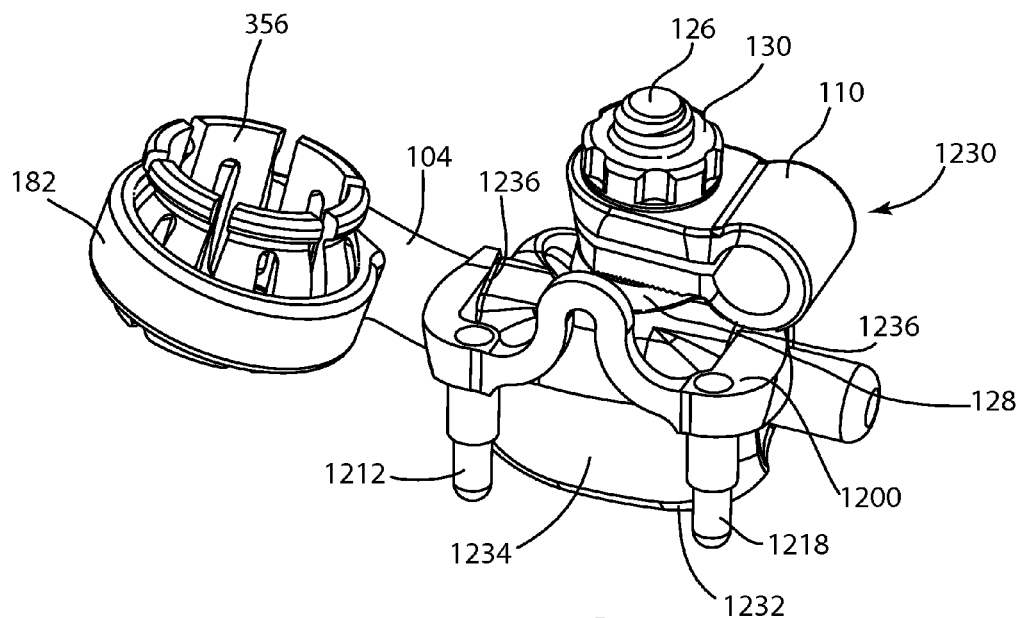

With reference to FIGS. 7, 28, and 29, one method of implanting inferior facet replacement implant 1230 and superior facet replacement implant 210 is as follows. It is understood that steps may occur in the order presented, or in a different sequence. It is further understood that right and left facet joint replacements may be implanted during the same procedure and optionally linked via a crosslink. Fixation assembly 350 is implanted into a prepared pedicle, and ring 212 of superior implant 210 is positioned and taper-locked onto the fixation assembly 350, as described previously. A second fixation assembly 350 (not shown) is implanted into the pedicle of the adjacent cephalad vertebra, minus sphere 356, capture nut 358 and top nut 360. Clip 1200 and attached inferior implant 1230 are removed from sterile packaging and coupled to delivery tool 1300. The delivery tool 1300 is manipulated to position sphere 356 onto fixation assembly 350, and posts 1212, 1218 of the clip 1200 into the holes 216, 218 of the superior facet implant 210. As the clip is positioned, polyaxial adjustment may occur at several junctures, allowing adjustment of the inferior articular surface 1234 relative to the fixation assembly 350. Ring 182 of strut 104 may rotate about sphere 356 relative to the fixation assembly 350, the position of inferior articular body 1232 may be adjusted along strut post 184 of strut 104 to match the offset distance between the adjacent vertebrae, the conical expander 126 may rotate about the strut post 184, and the split shell 128 may rotate within the inferior articular body 1232. When the clip 1200 is properly positioned so that the posts 1212, 1218 fit into the holes 216, 218 and the articular surfaces 214, 1234 are aligned, the delivery tool 1300 may be triggered to release the clip from the hook 1304, and the delivery tool 1300 is removed. A crosslink such as 108 may be positioned in the split clamp 110. The fixation assembly 350 is taper-locked relative to the sphere 356 and inferior strut 104, and capture nut 358 and top nut 360 are added to secure the assembly. Nut 130 is actuated on conical expander 126 to lock down the relative orientation of inferior strut 104 and inferior articular body 1232, and lock the position of crosslink 108. Flexing tool 1320 is attached to the connecting portion 1206 of the clip 1200, and activated to flex the connecting portion. As the connecting portion 1206 of the clip 1200 is flexed, shoulder 1208 rotates relative to the axis of post 1212, and shoulder 1214 rotates relative to the axis of post 1218, and tabs 1210, 1216 are urged apart, and out of slots 1236. Thus, clip 1200 is detached from inferior implant 1230 and also can be urged away from superior implant 210.

Various methods for implanting the facet joint replacement system 10 described above, and alternate embodiments thereof, will now be described in relation to the instruments set forth above.

The pedicles of vertebrae 2 and 4 may be prepared for implantation of the fixation members according to the surgeon's preferred technique. Imaging apparatus, such as a fluoroscope or C-arm, may be used to visualize the operative pedicles. Pedicle preparation may include probing or tapping each pedicle to prepare a socket to receive the fixation member. In a preferred embodiment, the pedicles of the caudal vertebra, in this example vertebra 2 (FIG. 1), may be prepared so that the fixation member will be inserted substantially parallel to the superior endplate of vertebra 2, or at an optimal angle relative to the sagittal plane 3, or both. Bone resection may be performed at this time, and may include decompression as well as partial or total facetectomy at the operative spinal level. Alternatively, bone resection may be performed later in the surgical procedure.

Figure 34A:
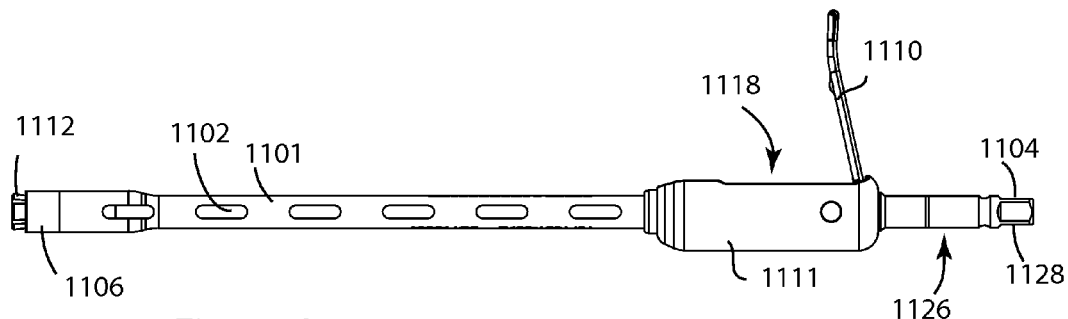
FIG. 34A is a side view of the screw driver of FIG. 31 in an unlocked configuration.
Figure 34B:
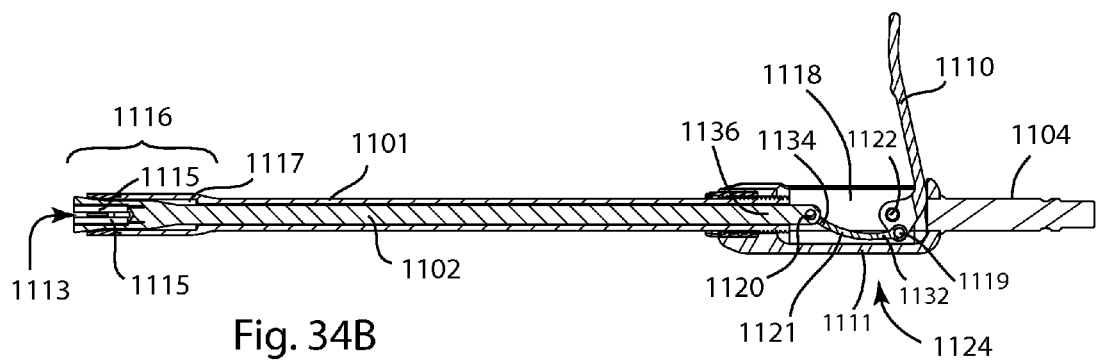
FIG. 34B is a cross-sectional view of the screw driver of FIG. 34A.
Figure 34C:
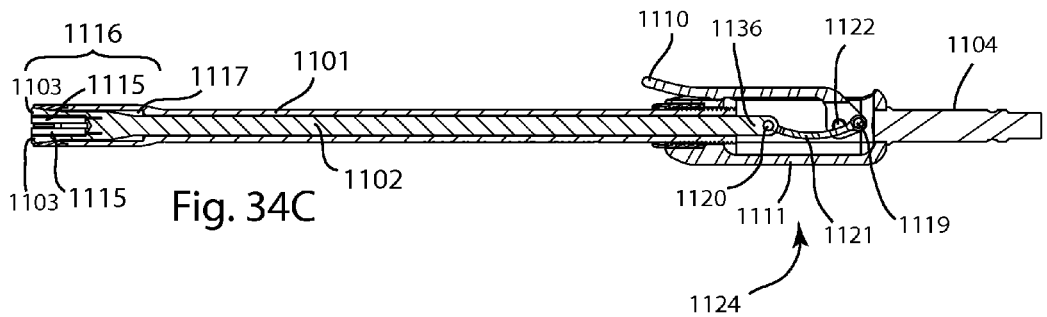
FIG. 34C is a cross sectional view of the screw driver of FIG. 31 in a locked configuration.
Figure 35:
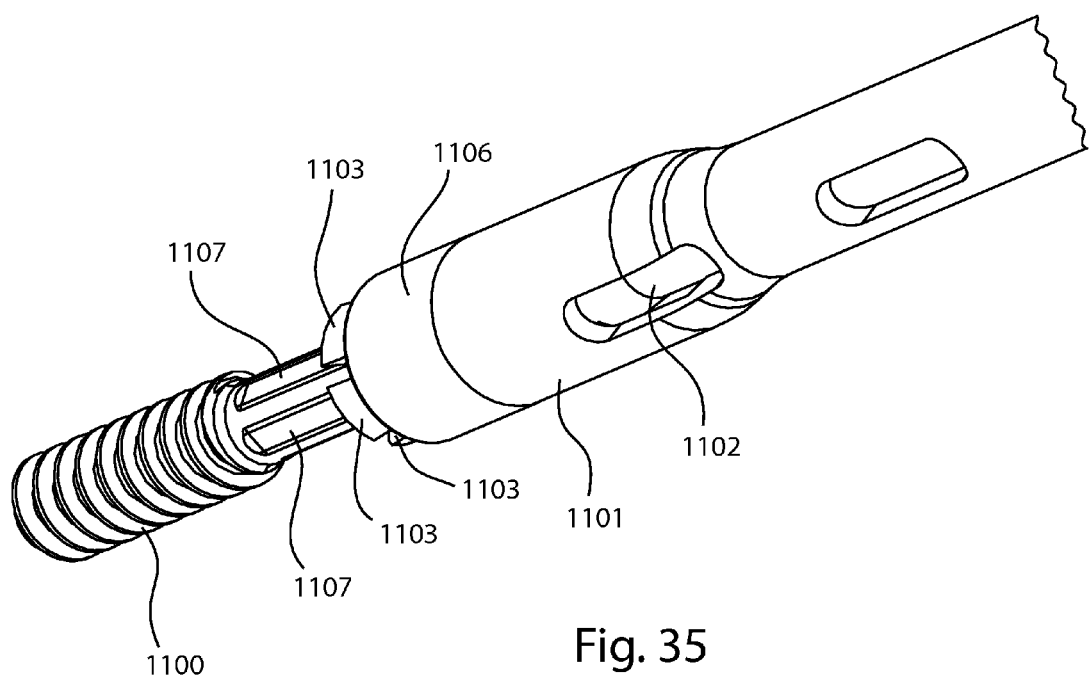
FIG. 35 is a detail view of the screw driver of FIG. 31 coupled to a fixation element.
Figure 36A:
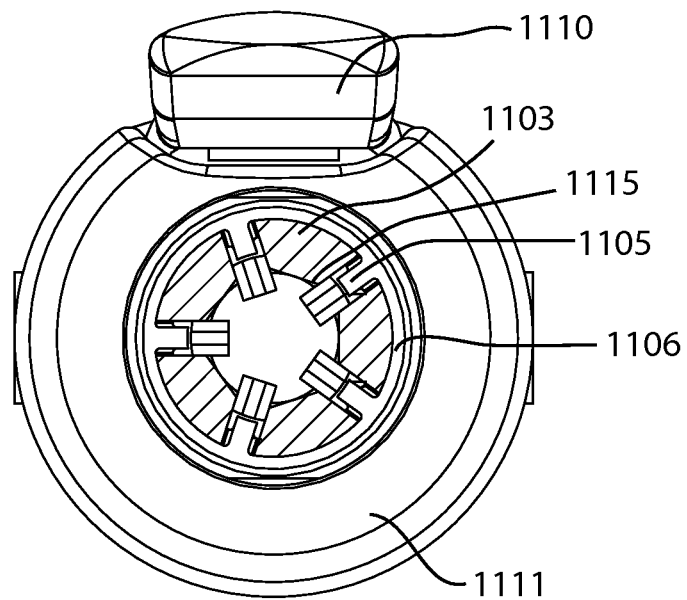
FIG. 36A is a cross-sectional view through the distal end of the collet of the screw driver of FIG. 31.
Figure 36B:
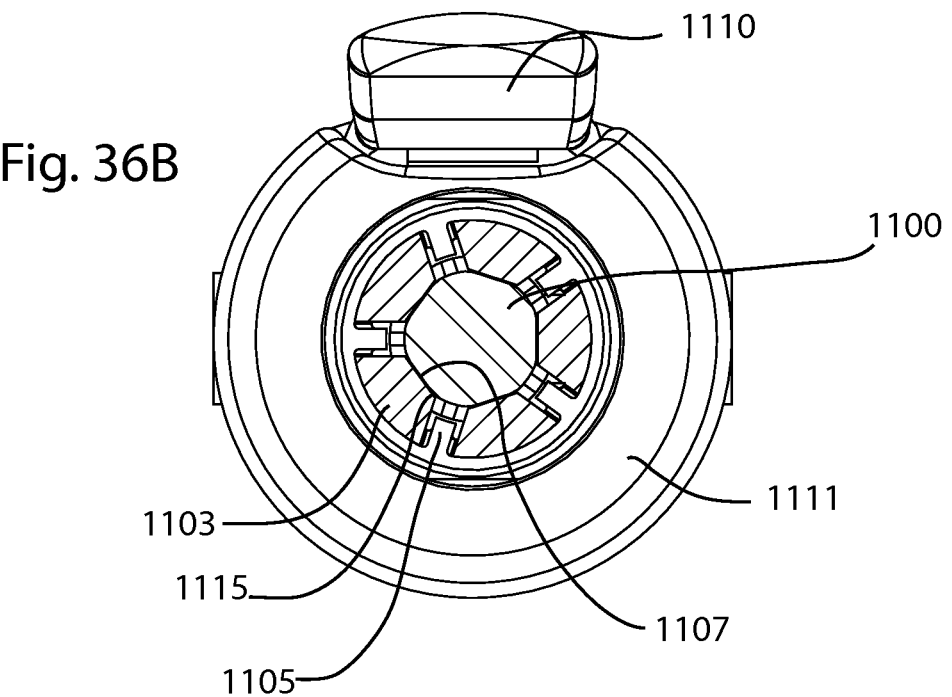
FIG. 36B is a cross-sectional view through the distal end of the collet of the screw driver of FIG. 31 and the fixation element of FIG. 35.

Referring to FIGS. 34-36, screw driver 1130 may be used to insert a pedicle screw 1100 into each pedicle. The unlocked configuration of screw driver 1130 is selected by lifting the lever 1110 away from the handle 1111. The proximal end of pedicle screw 1100 is inserted into the collet 1112 so that it contacts the bottom of the center bore 1113. In this way, a predetermined length of the pedicle screw 1100 is enclosed within the distal end 1106 of the screw driver 1130. In a preferred embodiment, the predetermined length may be about 13 mm. The locked configuration of screw driver 1130 is then selected by pressing the lever 1110 against the handle 1111. As the lever 1110 is depressed, the collet 1112 retracts into the distal end 1106 of the outer sleeve 1101 and the inner walls 1115 of the prongs 1103 are compressed by the outer sleeve 1101 tightly against the flats 1107 of pedicle screw 1100. The distal end of the pedicle screw 1100 is threaded into the pedicle until the distal tip 1106 of the screw driver 1130 contacts the bone surface around the pedicle screw 1100. The distal tip 1106 of the screw driver 1130 resists further advancement of the pedicle screw 1100 into the pedicle. The unlocked configuration of screw driver 1130 is again selected by lifting the lever 1110 away from the handle 1111, and the screw driver 1130 is detached from the pedicle screw 1100. In this way, the pedicle screw 1100 is inserted into the bone so that a predetermined length of the proximal end of the pedicle screw 1100 is exposed.

Figure 37A:
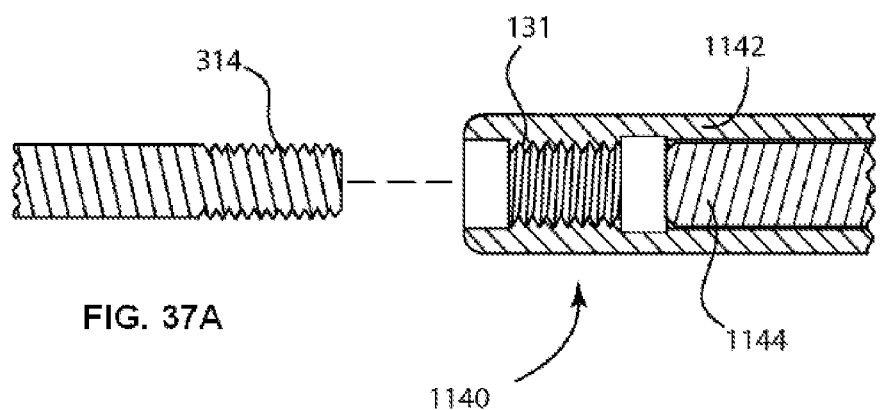
FIG. 37A is a cross-sectional view through an alternate embodiment of a screw driver.
Figure 37B:
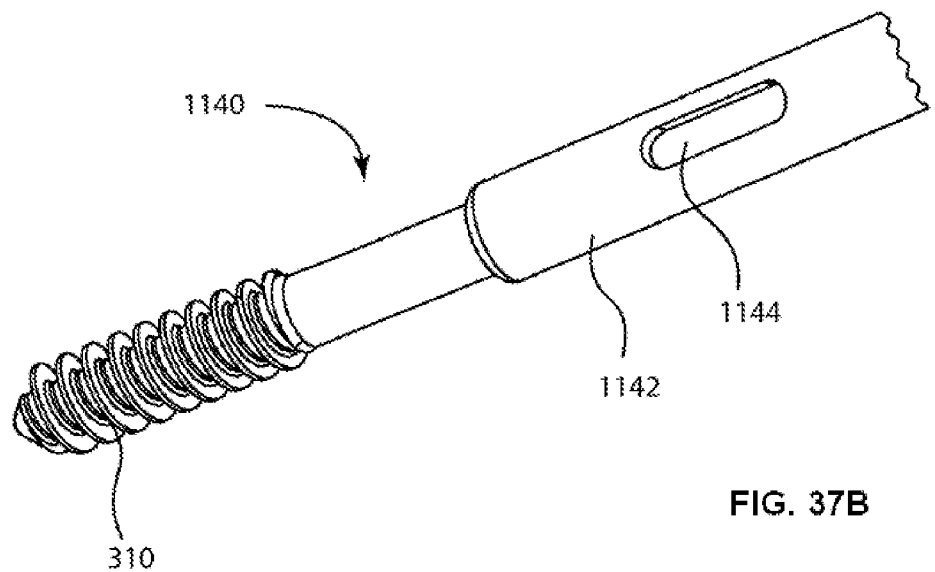
FIG. 37B is a detail view of the distal end of the screw driver of FIG. 37A coupled to a fixation element.

Alternatively, referring to FIGS. 37-38, screw driver 1140 may be used to insert a pedicle screw 1100 into each pedicle. The locked configuration of screw driver 1140 is selected by depressing the lever 1148 against the handle 1146. The proximal end of the pedicle screw 1100 is threaded into the distal end 1164 of the outer sleeve 1142 until it abuts the distal end 1160 of the inner shaft 1144. In this way, a predetermined length of the pedicle screw 1100 is enclosed within the distal end 1164 of the screw driver 1140. At this point, the inner shaft 1144 resists further advancement of the pedicle screw 1100 into the outer sleeve 1142, causing the proximal threads of the pedicle screw 1100 to bind in the threads in the distal end 1164 of the outer sleeve 1142. The distal tip of the pedicle screw 1100 is then threaded into the pedicle until the distal tip 1164 of the outer sleeve 1142 contacts the bone surface around the pedicle screw 1100. The distal tip 1164 of the screw driver 1140 resists further advancement of the pedicle screw 1100 into the pedicle. The unlocked configuration of the screw driver 1140 is selected by lifting the lever 1148 away from the handle 1146. This separates the distal end 1160 of the inner shaft 1144 from the proximal end of the pedicle screw 1100 so that the screw driver 1140 may be easily unthreaded from the pedicle screw 1100. In this way, the pedicle screw 1100 is inserted into the bone so that a predetermined length of the proximal end of the pedicle screw 1100 is exposed.

Alternatively, screw driver 1140 may be used to insert other fixation elements into bone, such as fixation element 302 or 352.

Figure 51:
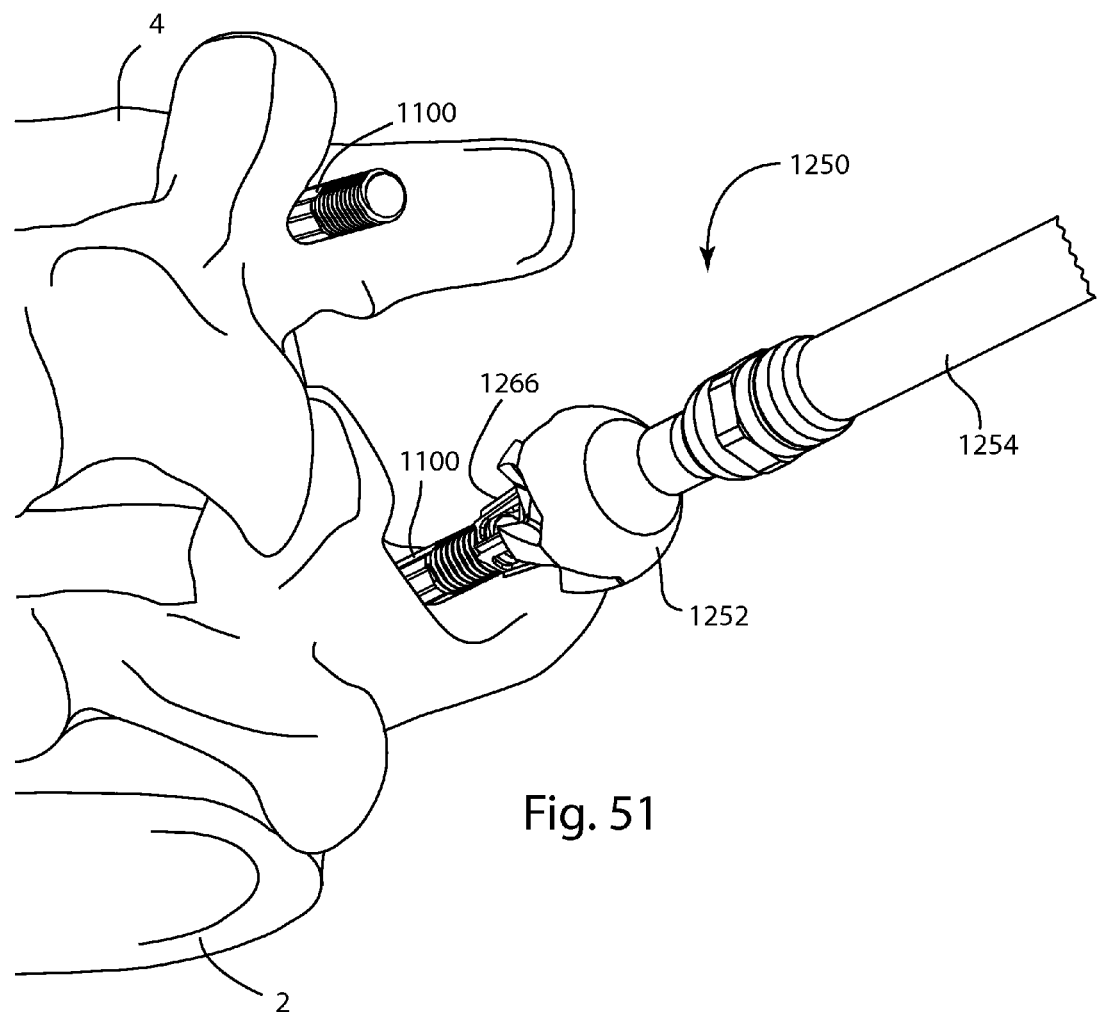
FIG. 51 is a posterior view of the base reamer of FIG. 39 passing over a fixation element in a caudal vertebra.
Figure 52:
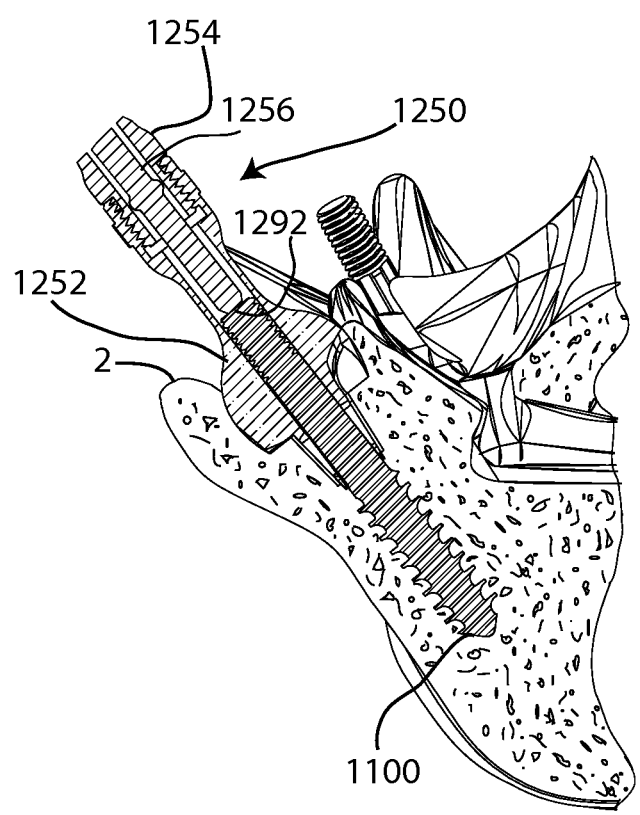
FIG. 52 is a partial cross-sectional view of the base reamer, fixation element, and vertebra of FIG. 51, cut along the longitudinal axis of the fixation element.

Referring to FIGS. 51-52, the pedicles may be further prepared by reaming a bone socket that is sized and shaped to receive a particular implant base. The bore 1274 of the base reamer 1250 is placed over the exposed proximal end of the pedicle screw 1100, or other fixation member. When the base reamer 1250 is first placed over the pedicle screw 1100, the inner shaft 1256 tends to slide toward its distal limit due to gravity. Thus, the line 1288 is distally displaced from the target line 1278 on the outer sleeve 1254. As the base reamer 1250 is rotated and advanced over the pedicle screw 1100, the distal end 1292 of inner shaft 1256 contacts the proximal end of the pedicle screw 1100. As the base reamer 1250 advances further over the pedicle screw 1100, the outer sleeve 1254 advances over the now stationary inner shaft 1256 so that line 1288 approaches line 1278. When the inner shaft 1256 reaches its proximal limit, line 1288 is aligned with line 1278. Furthermore, the inner shaft 1256 physically resists further advancement of the base reamer 1250 into the bone. In this way, the penetration of the base reamer 1250 may be limited to a predetermined depth relative to the exposed proximal end of the pedicle screw 1100.

Figure 53:
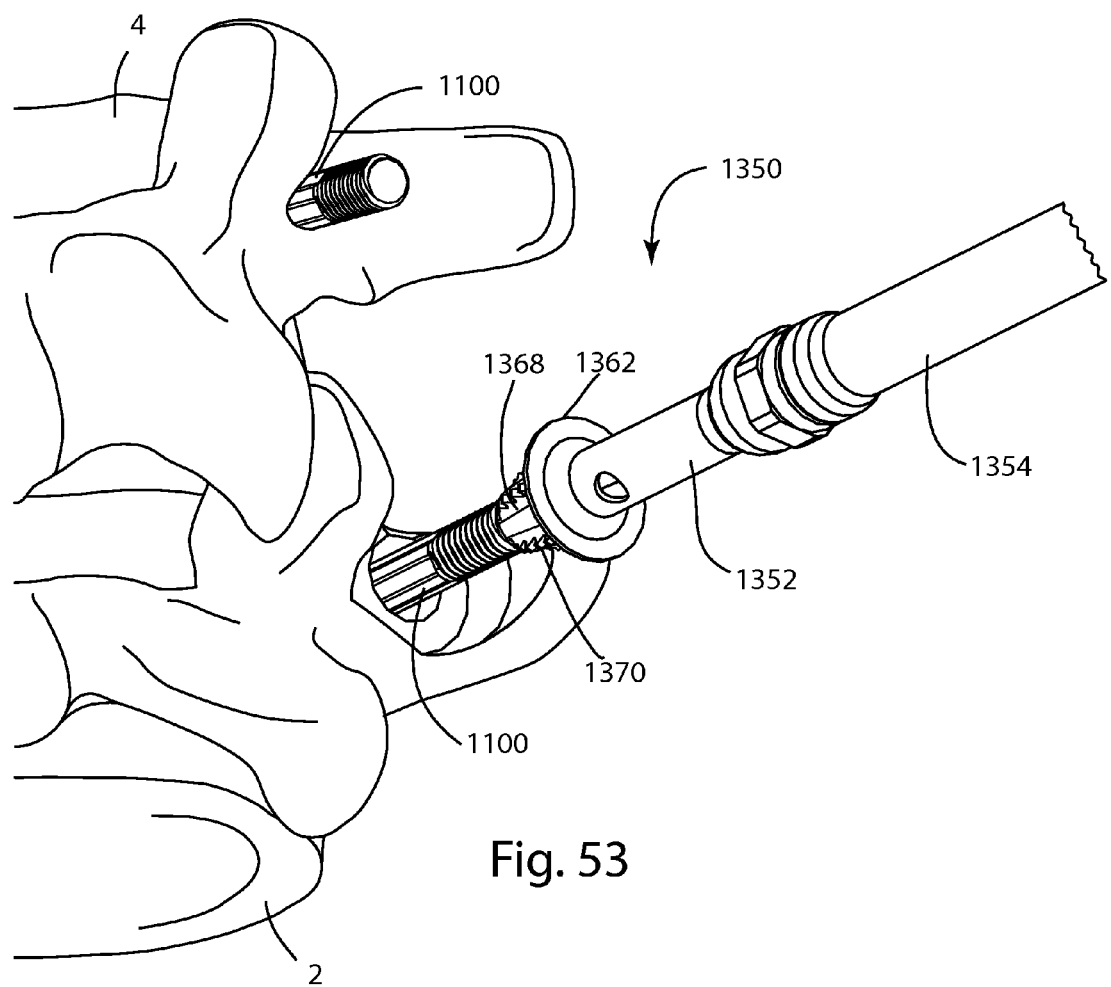
FIG. 53 is a posterior view of the base broach of FIG. 40 passing over a fixation element in a caudal vertebra.

FIG. 52 shows a cross section through the left and right pedicle axes of vertebra 2 with base reamer 1250 fully seated with respect to pedicle screw 1100 after reaming the bone socket. The distal tip 1292 of the inner shaft 1256 of the base reamer 1250 contacts the proximal end of the pedicle screw 1100 and the inner shaft 1256 is at its proximal limit. FIG. 53 provides a perspective view of the reamed bone socket.

As an alternative, the base reamer may lack a movable inner shaft 1256, and may instead have a reamer tip with a center bore having the predetermined depth. This embodiment would provide a physical depth stop to prevent overpenetration of the base reamer into the bone, although no external indicator would be provided.

It can be appreciated that the surgeon would select a particular base reamer to correspond to the specific implant base that will be implanted in a given pedicle.

As an optional step, the pedicles may be broached in order to precisely configure the bone socket to receive a particular implant base. A broaching step may or may not be necessary, depending on factors such as implant base configuration or bone quality. Certain embodiments of the implant base may be designed with self-cutting fins or other features, so that broaching is unnecessary. However, broaching may ensure that an adequate bone socket is prepared in hard or dense bone, or for an implant base having a raised bone ingrowth surface treatment.

Figure 54:
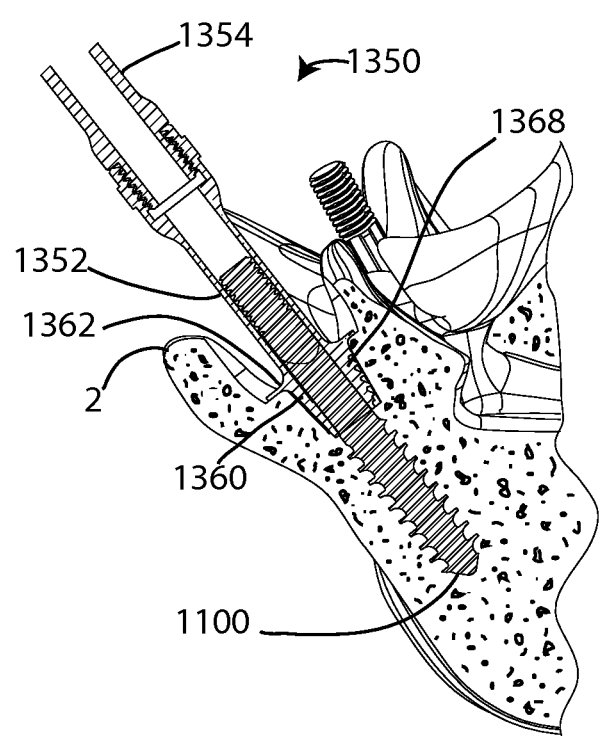
FIG. 54 is a partial cross-sectional view of the base broach, fixation element, and vertebra of FIG. 53, cut along the longitudinal axis of the fixation element.

With reference to FIGS. 53-54, the bore 1364 of base broach 1350 is placed over the exposed proximal end of the pedicle screw 1100, or other fixation member if used. If present, corresponding flats 1372 and 1107 must be aligned in order for the base broach to advance over the pedicle screw 1100. By aligning the corresponding flats 1372 and 1107, any anti-rotation features present on the base broach will be oriented with respect to the pedicle screw 1100, and as will be described presently, the corresponding anti-rotation features of the implant base will be aligned with the broached socket by the pedicle screw 1100. Alternatively, if flats are not present on the base broach and fixation member, then any anti-rotation features on the broach may be aligned according to the surgeon's preference.

Once properly aligned, the base broach 1350 is advanced into the bone until it penetrates to a predetermined depth relative to the exposed proximal end of the pedicle screw 1100. Various means of controlling base broach penetration are contemplated within the scope of the present invention. A flange 1362, if present, may contact a bone surface cut at a predetermined depth by the base reamer 1250. The flange 1362 resists further advancement of the base broach into the bone. The bore 1364 of the base broach 1350 may comprise the predetermined depth. A movable inner shaft, similar or identical to inner shaft 1256 of the base reamer 1250, may be provided in an alternate embodiment of the base broach.

Figure 55:
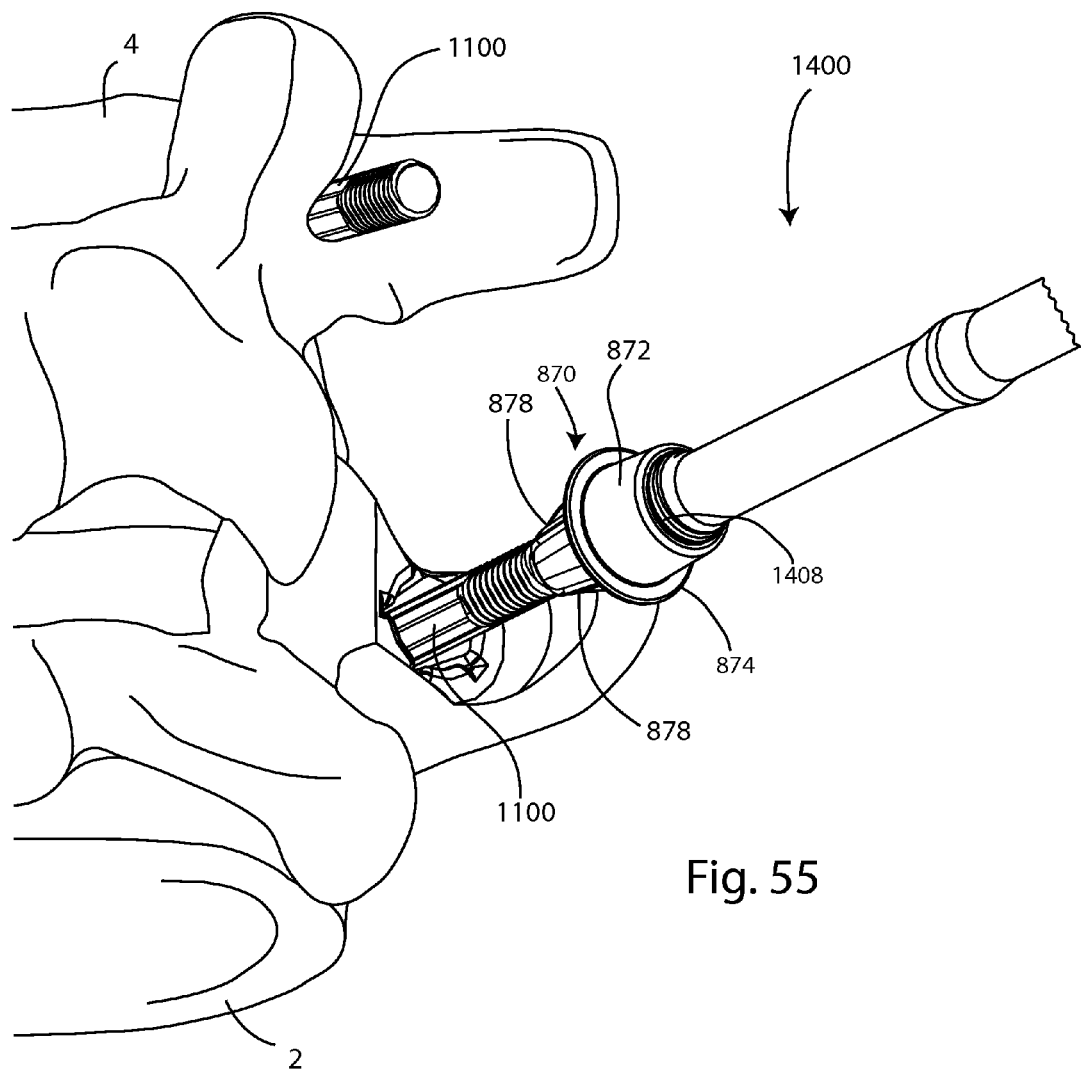
FIG. 55 is a posterior view of an implant base, coupled to the base inserter and handle of FIG. 42, passing over a fixation element in a caudal vertebra.

FIG. 54 shows a cross section through the left and right pedicle axes of vertebra 2 with base broach 1350 fully seated with respect to pedicle screw 1100 after broaching the bone socket. Due to the odd number of fins 1368 on broach tip 1352, the cross section cuts one fin 1368 at full height, while on the opposite side of the broach tip 1352, the body 1360 is cut. The flange 1362 of the base broach tip 1352 is in contact with a corresponding flat surface of the reamed bone socket, thus acting as a depth stop by limiting further advancement of the base broach 1350 into the bone. FIG. 55 offers a perspective view of the broached bone socket.

It can be appreciated that the surgeon would select a particular base broach to correspond to the specific implant base that will be implanted in a given pedicle.

Figure 56:
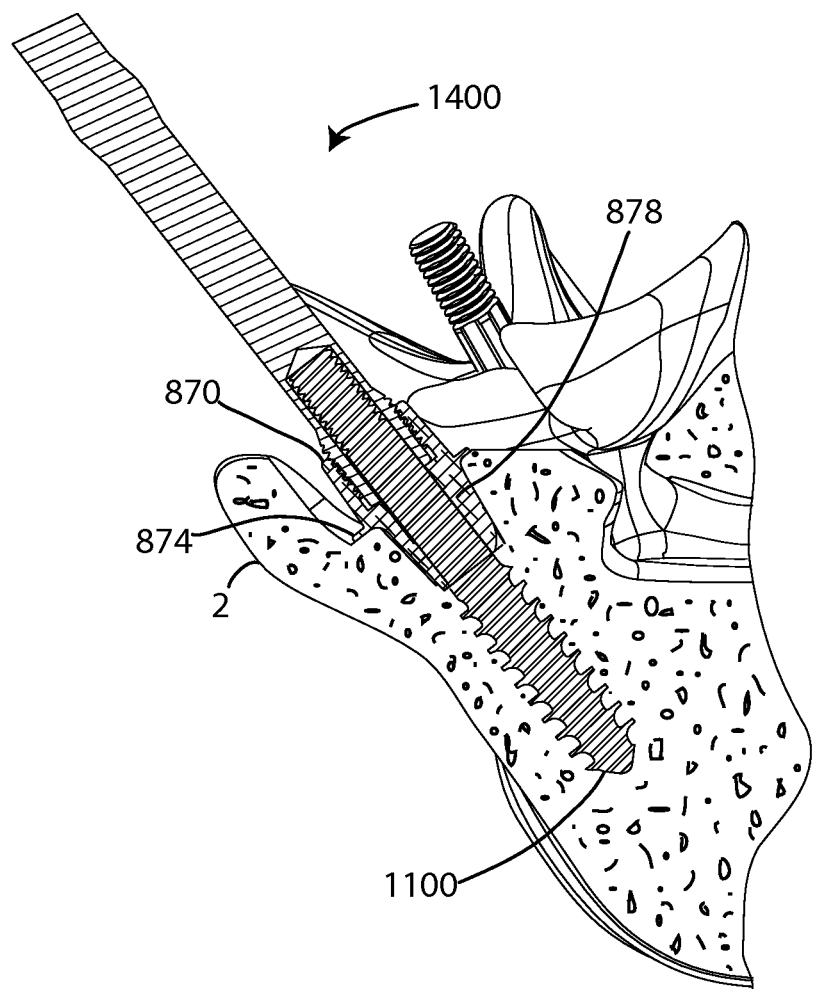
FIG. 56 is a partial cross-sectional view of the implant base, base inserter, handle, fixation element, and vertebra of FIG. 53, cut along the longitudinal axis of the fixation element.
Figure 57A:
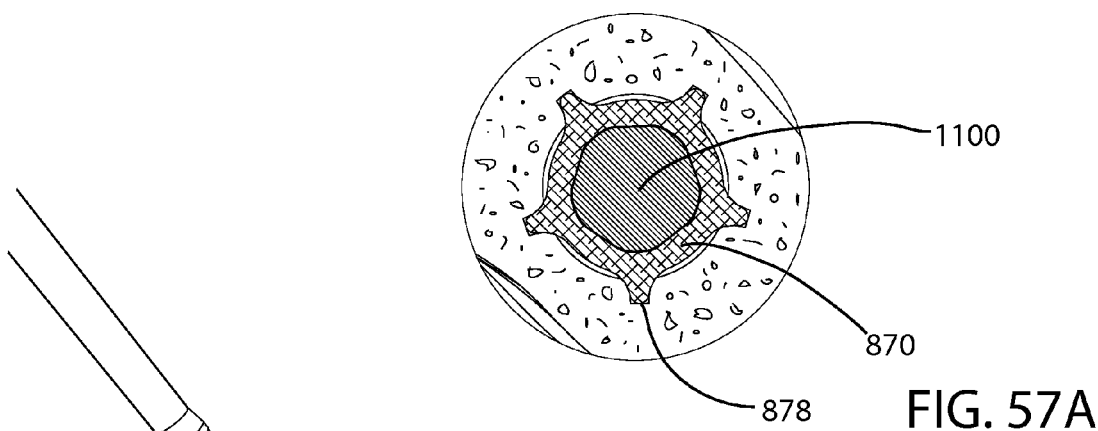
FIG. 57A is a detail cross-sectional view of the implant base, base inserter, handle, fixation element, and vertebra of FIG. 53, cut perpendicular to the longitudinal axis of the fixation element.
Figure 57B:
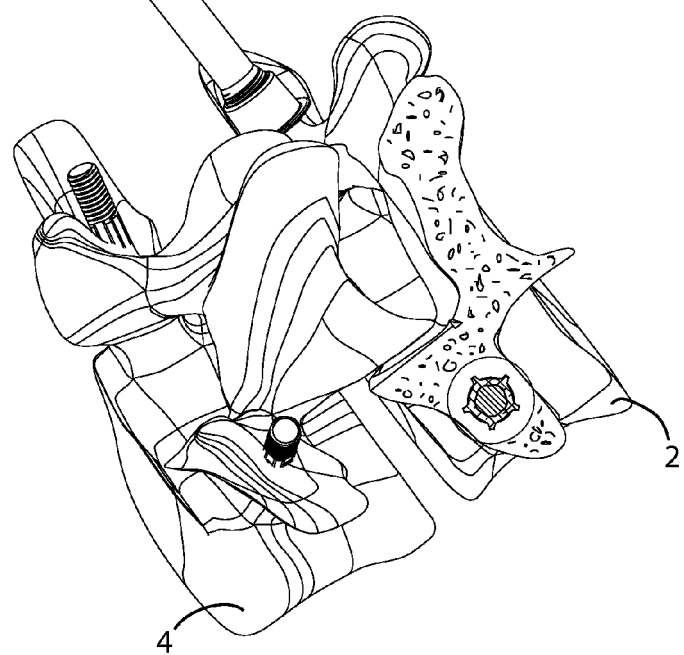
FIG. 57B is a partial cross-sectional view of the implant base, base inserter, handle, fixation element, and vertebra of FIG. 53, cut perpendicular to the longitudinal axis of the fixation element.
Figure 58:
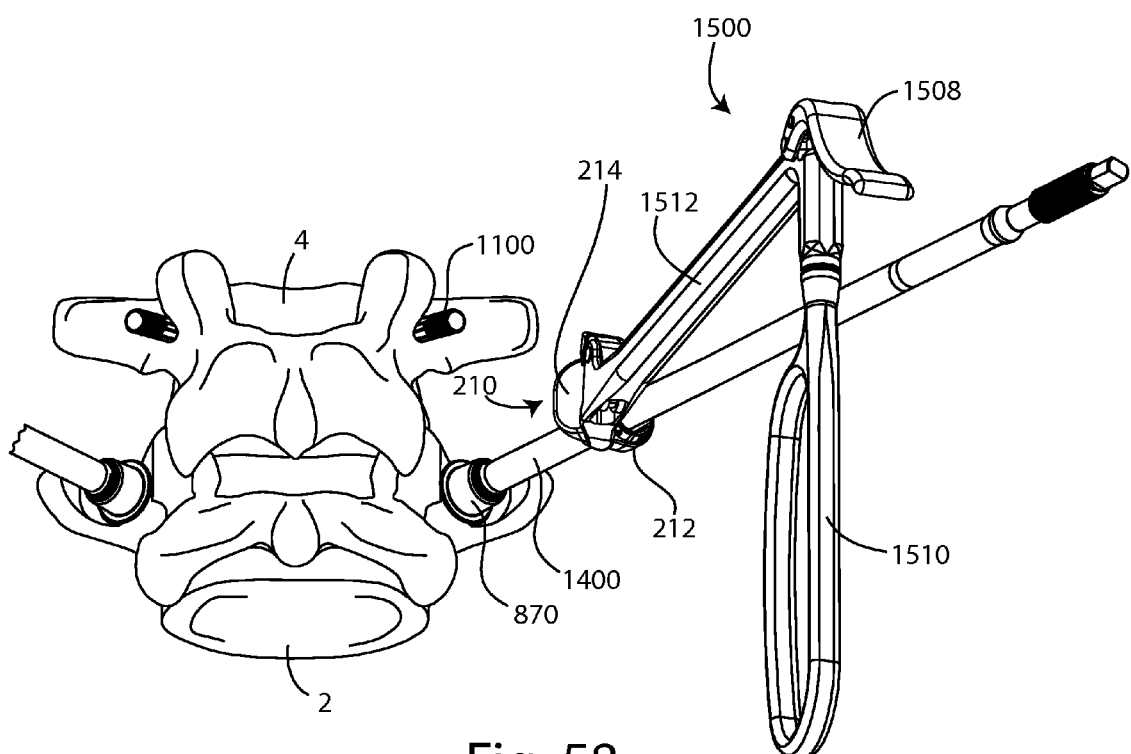
FIG. 58 is a posterior view of a superior implant, coupled to the superior implant inserter of FIG. 43, passing over the base inserter of FIG. 41 coupled to an implant base in a vertebra.
Figure 59:
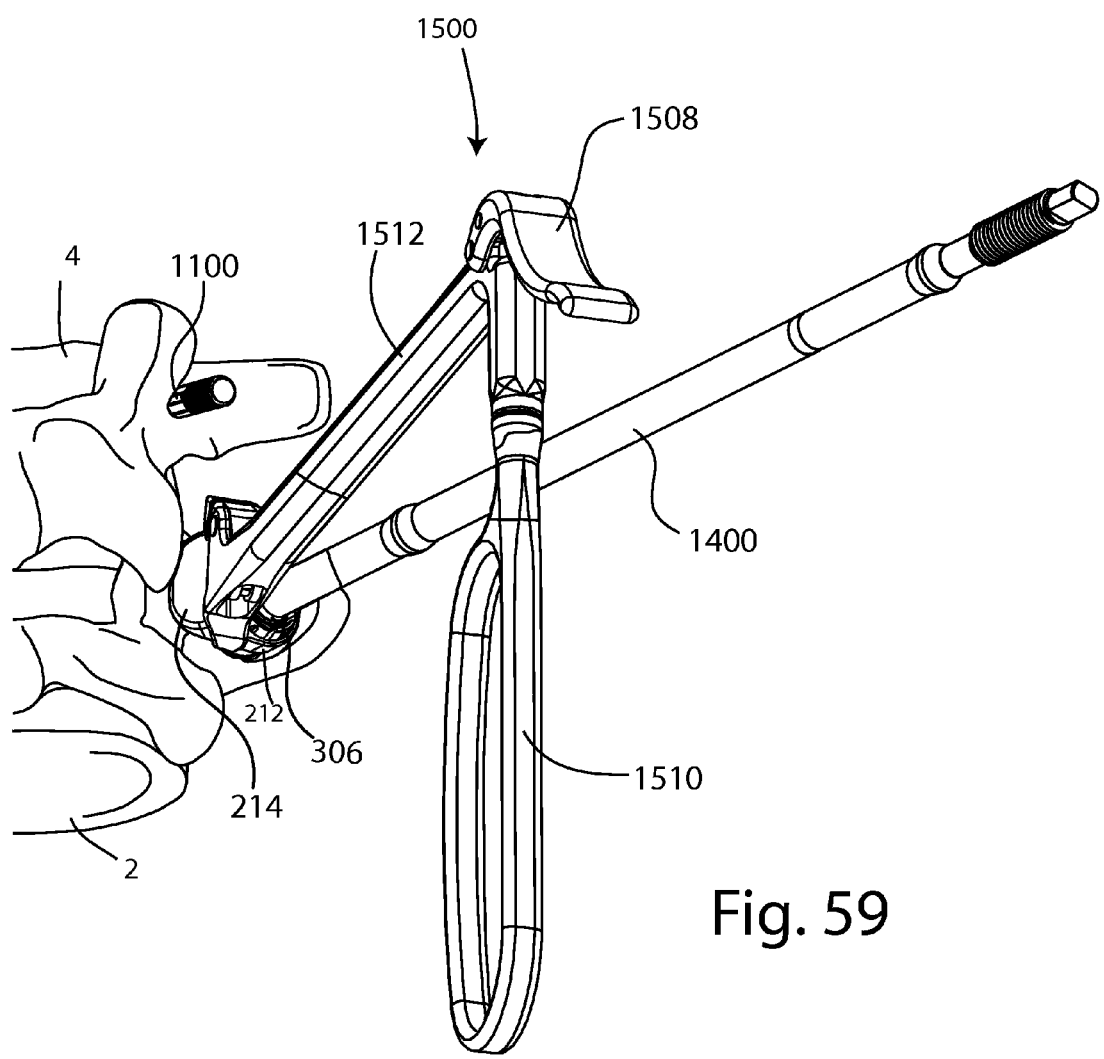
FIG. 59 is a posterior view of the superior implant, superior implant inserter, base inserter, and implant base of FIG. 58, with the superior implant engaging the implant base.

Referring to FIGS. 55-57, the base inserter 1400 is used to place the implant base 870 over the pedicle screw 1100 and seat the implant base 870 into the prepared bone socket in the pedicle. The threads 877 of the implant base 870 are threaded onto the distal end 1402 of the base inserter 1400 and modular handle 1410 is attached to the proximal end 1404 of the base inserter 1400. The lumen 871 of the implant base 870 is placed over the exposed proximal end of the pedicle screw 1100. The corresponding flats 873 and 1107 must be aligned in order for the implant base 870 to advance over the pedicle screw 1100. By aligning the corresponding flats 873 and 1107, the anti-rotation features present on the implant base will be aligned with the broached socket by the pedicle screw 1100.

Once properly aligned, the implant base 870 is advanced into the bone until it penetrates to a predetermined depth relative to the exposed proximal end of the pedicle screw 1100. Various means of controlling the implant base 870 penetration are contemplated. A flange 874, if present, may contact a bone surface cut at a predetermined depth by the base reamer 1250. The flange 874 resists further advancement of the base broach into the bone. There may also be audible or tactile sensory feedback when the flange 874 contacts the bone surface. The bore 1406 of the base inserter 1400 may comprise the predetermined depth. A movable inner shaft, similar or identical to inner shaft 1256 of the base reamer 1250, may be provided in an alternate embodiment of the base inserter.

FIGS. 56-57 show the fully seated implant base 870 in cross section. FIG. 56 shows a cross section through the left and right pedicle axes of vertebra 2 with implant base 870 fully seated with respect to pedicle screw 1100. The flange 874 of the implant base 870 is in contact with a corresponding flat surface of the prepared bone socket, thus acting as a depth stop by limiting further advancement of the implant base 870 into the bone. Furthermore, the bore 1406 of the base inserter 1400 acts as a depth stop by abutting the proximal end of the pedicle screw 1100. FIG. 57 shows a cross section perpendicular to the pedicle axis and distal to the flange 874.

When the implant base 870 is fully seated, the modular handle 1410 may be removed. However, in a preferred embodiment of the surgical technique, the base inserter 1400 remains attached to the implant base 870 and is used in subsequent surgical steps.

Alternatively, implant base 354 may be threaded onto the base inserter 1400. Implant base 354 may lack flats, and therefore may be suitable for use with fixation element 352, which also lacks flats. In this case, the surgeon would align any anti-rotation features of implant base 354 with the previously broached socket.

In a further alternative, implant base 304, 850, or 880 may connect to an alternate embodiment of a base inserter (not shown) which has a complementary distal tip to engage the tool engagement rim 322.

Referring to FIGS. 58-61, in a preferred embodiment, the superior implant 210 may be supplied with a split sphere 306 captive within the superior implant ring 212. The superior facet joint implant 210 with split sphere 306 may be grasped by the superior inserter 1500 by embracing the implant 210 with the arms 1514, 1520, positioning the tabs 1516, 1522 to engage the notches 206 on opposite sides of the implant 210, and depressing the lever 1508 to close the moveable jaw 1504. The superior inserter 1500 grasps the implant 210 in a predetermined orientation established by the engagement of the tabs 1516, 1522 and the notches 206, and by the particular configuration of the arms 1514, 1520 relative to the shaft 1512.

Figure 60:
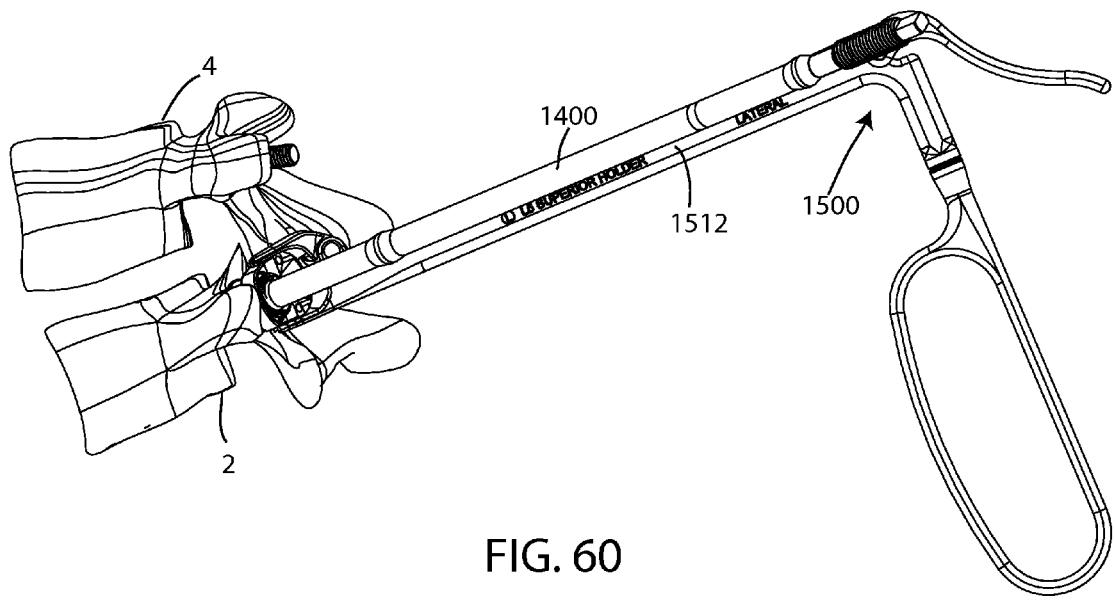
FIG. 60 is a lateral view of the superior implant, superior implant inserter, base inserter, and implant base of FIG. 59.
Figure 61:
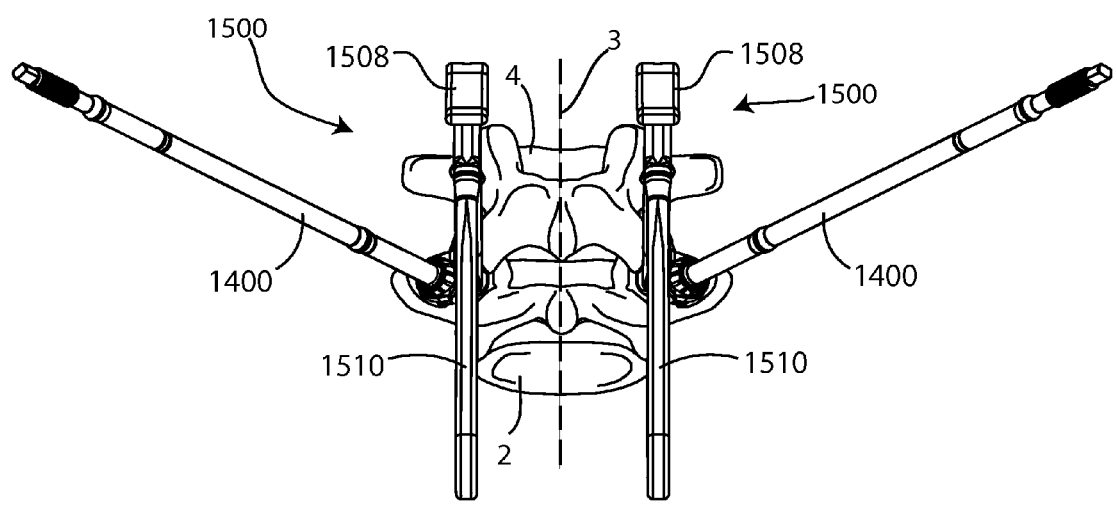
FIG. 61 is a posterior view of the superior implant, superior implant inserter, base inserter, and implant base of FIG. 59 and a contralateral set of minor image components.

The ring 212 of the superior implant 210, with captive split sphere 306, is placed over the base inserter 1400 and advanced over the tapered portion 872 of the implant base 870 so that the split sphere 306 contacts the tapered portion 872 and the superior articular surface 214 faces medially. The superior implant 210 may then be placed in a desired orientation by positioning shaft 1512 of the superior inserter 1500 parallel with the superior endplate of the vertebra (FIG. 60). Fluoroscopic or other imaging equipment may be used to ensure the shaft 1512 is properly aligned. The handle 1510 of the superior inserter 1500 may also be positioned parallel to the sagittal plane 3 (FIG. 61), while maintaining the shaft 1512 in alignment with the superior endplate. The sagittal plane 3 and superior endplate alignment may be maintained during the subsequent lockout step.

Figure 62:
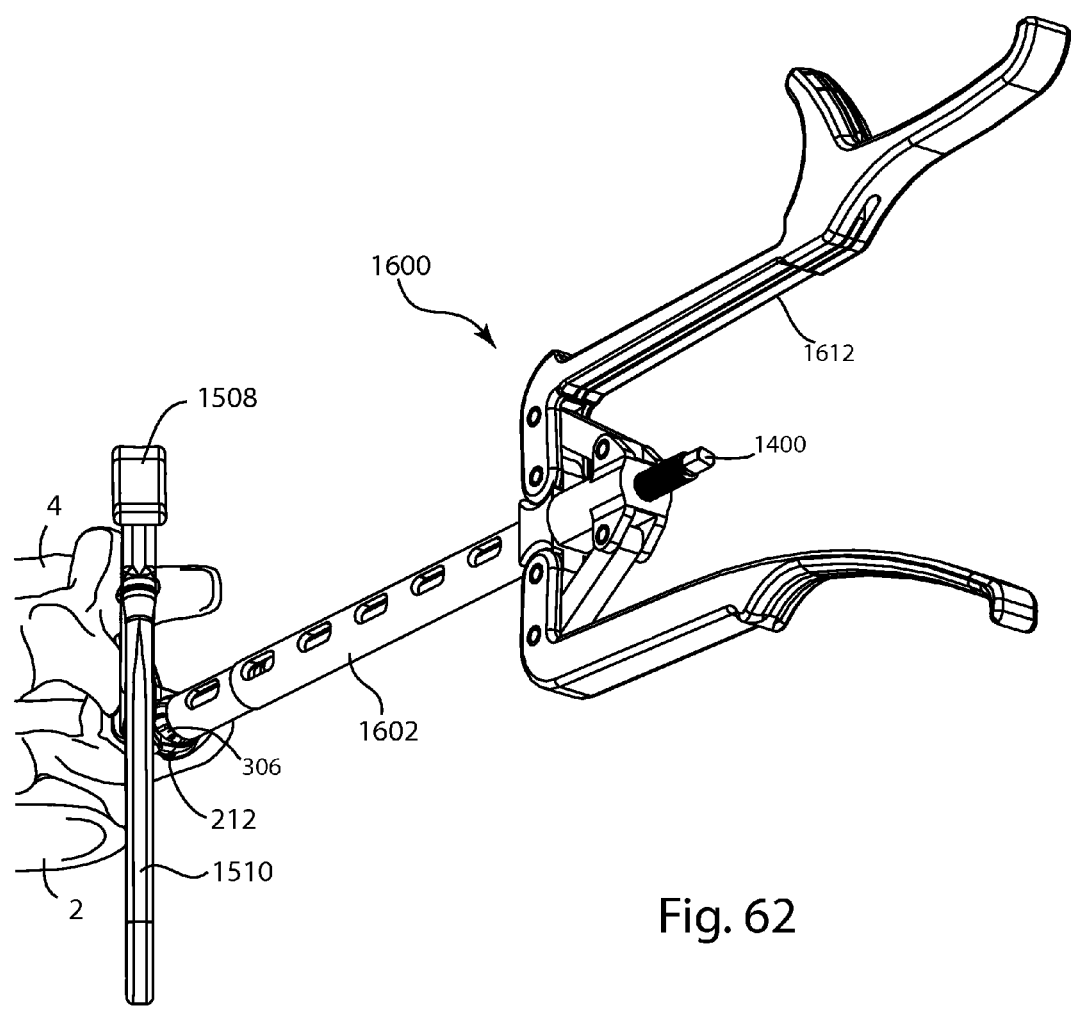
FIG. 62 is a posterior view of the superior implant, superior implant inserter, base inserter, and implant base of FIG. 59 and the lockout tool of FIGS. 44-45.
Figure 63:
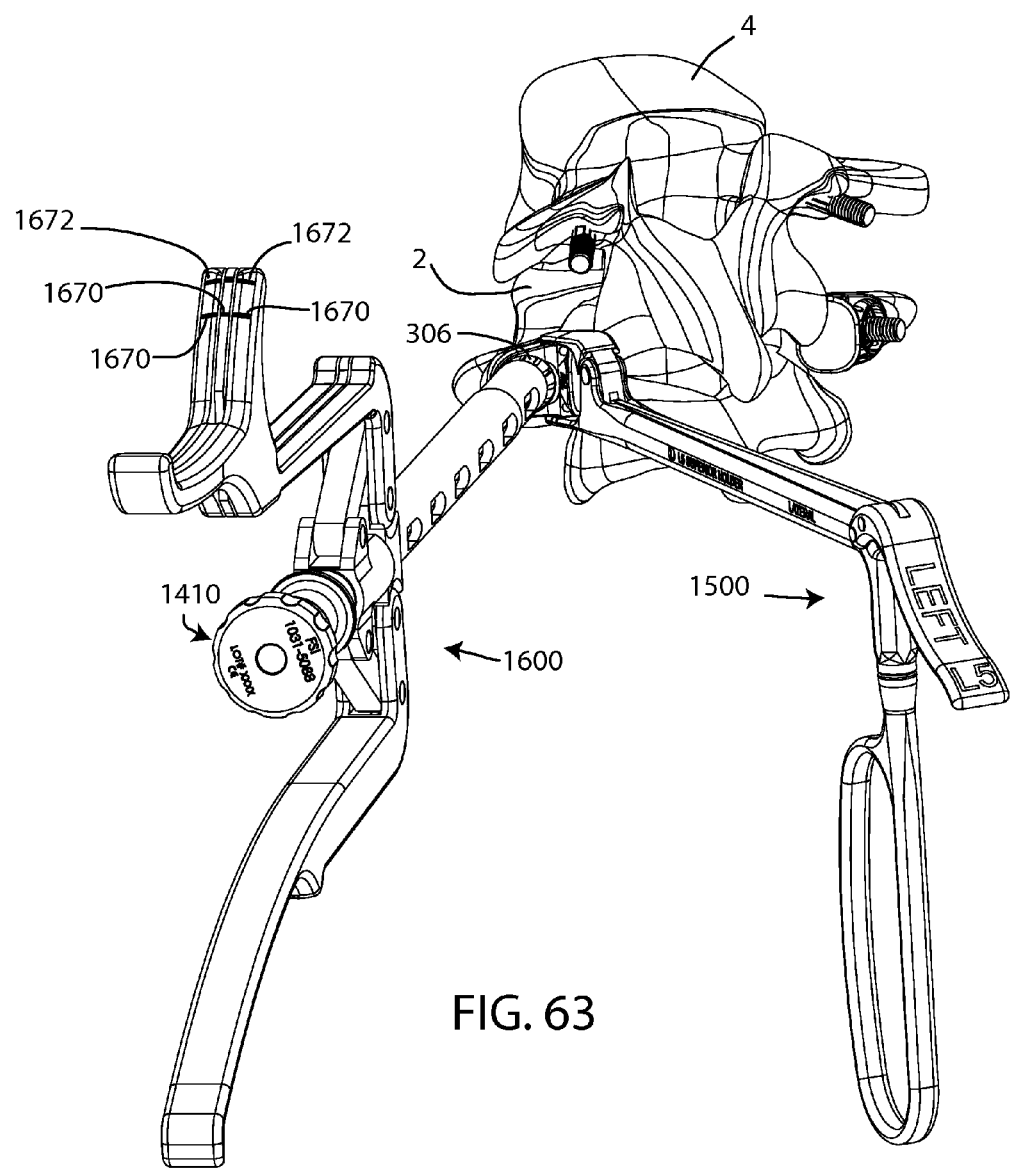
FIG. 63 is a perspective view of the superior implant, superior implant inserter, base inserter, implant base and lockout tool of FIG. 62, showing the lockout tool before actuation.
Figure 64:
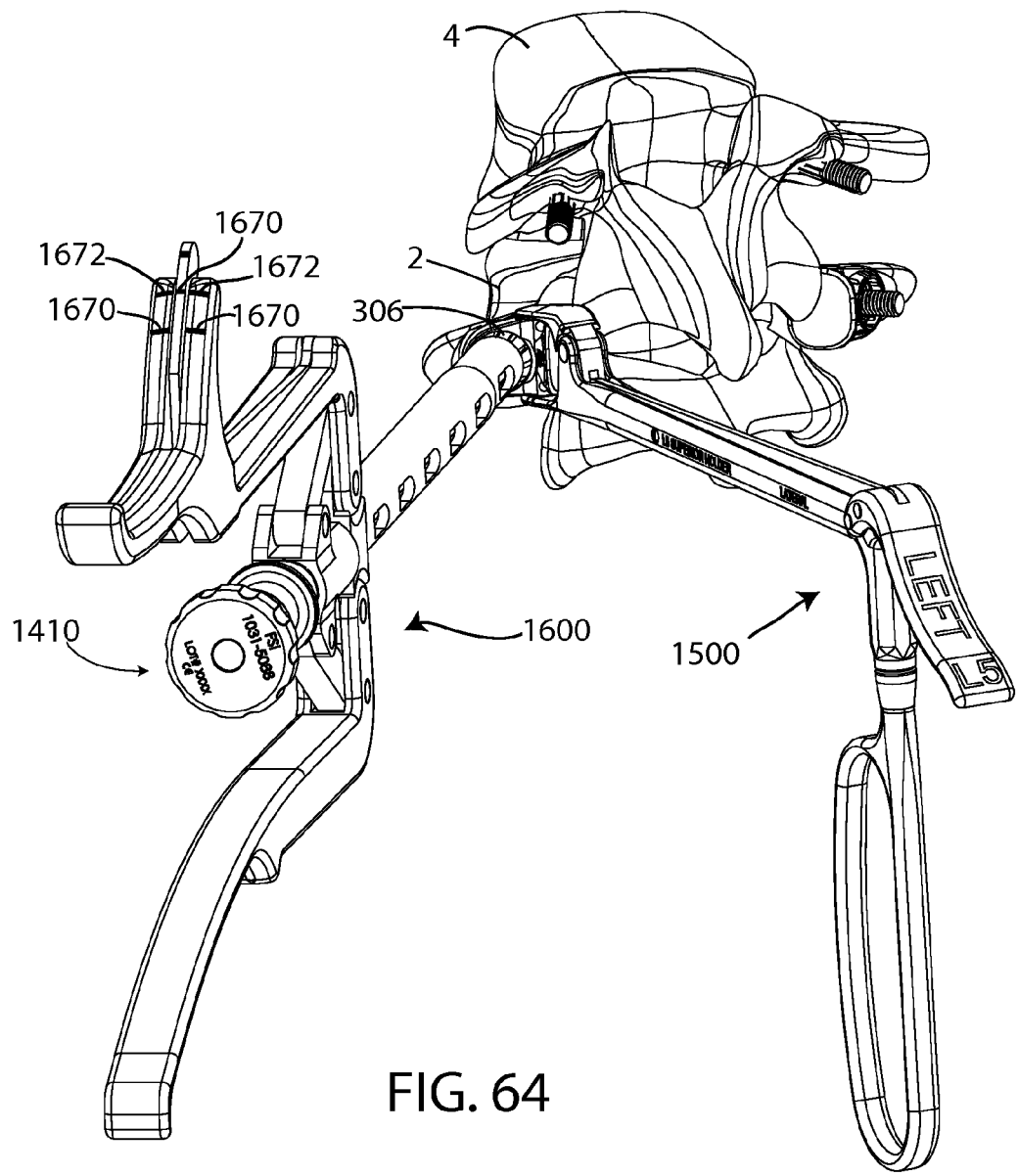
FIG. 64 is a perspective view of the superior implant, superior implant inserter, base inserter, implant base and lockout tool of FIG. 62, showing the lockout tool during actuation.

Referring now to FIGS. 62-64, the tube 1602 of the lockout tool 1600 is passed over the base inserter 1400 and advanced to contact the flange 368 of the split sphere 354, or a corresponding edge of split sphere 306. The modular handle 1410 is reattached to the proximal end 1404 of the base inserter 1400 where it protrudes from the drive sleeve 1606 of the lockout tool 1600. The handles 1610, 1612 of the lockout tool 1600 are squeezed together until the first line 1670, marked across the plate 1668, aligns with the second line 1672, marked across the projection 1658. As the handles 1610, 1612 are squeezed together, the lockout tool 1600 stabilizes itself on the implant base 870 with the base inserter 1400 and pushes on the split sphere 306 with the tube 1602 to lock the superior implant 210 to the implant base 870.

The modular handle 1410, lockout tool 1600, and base inserter 1400 are removed. Optionally, a capture nut 358 may be threaded into the threads 877 in the implant base 870. A top nut 360 is threaded onto the pedicle screw 1100 to hold the implant base 870 in the bone socket.

The surgeon may then remove the superior inserter 1500 by lifting the lever 1508 to open the moveable jaw 1504.

The pedicles of vertebra 4 may be reamed and optionally broached as previously described for vertebra 2. Implant bases may be inserted into the bone sockets as previously described. The base inserters 1400, or alternate embodiments thereof, preferably stay connected to the implant bases to be used in subsequent surgical steps.

Figure 65:
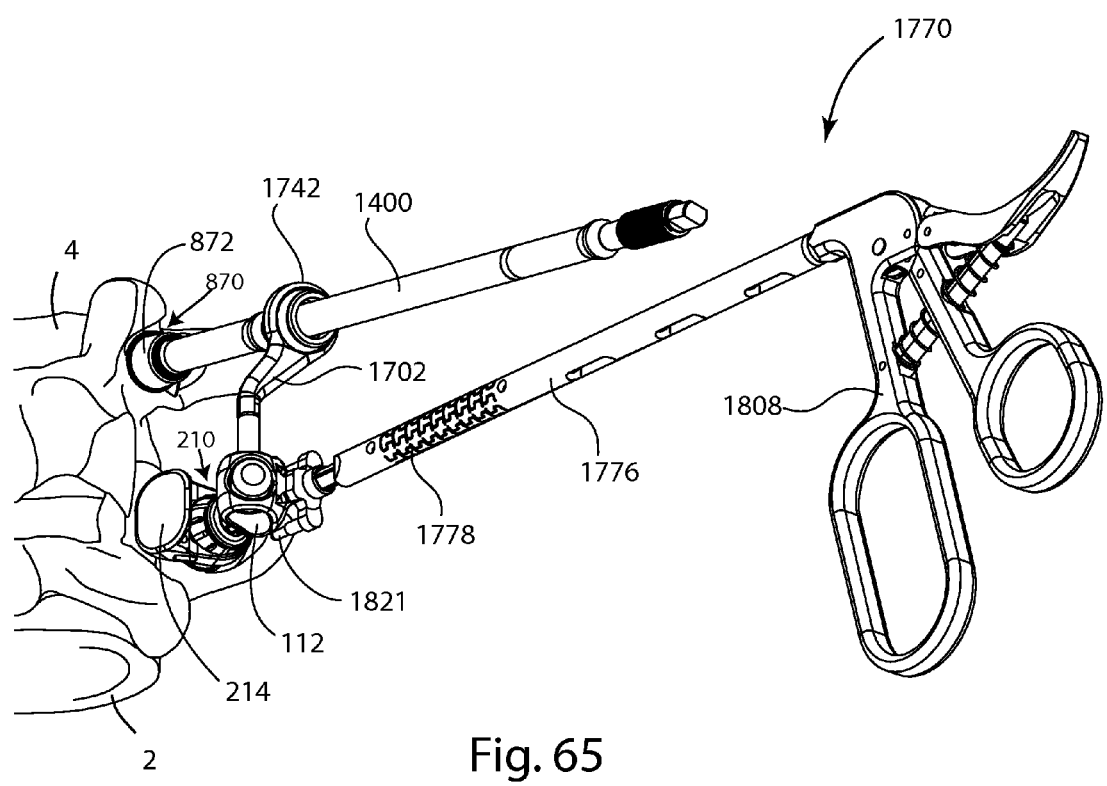
FIG. 65 is a posterior view of the superior implant and fixation assembly of FIG. 23 in a caudal vertebra, the base inserter of FIG. 41 coupled to an implant base in a cephalad vertebra, and an inferior trial, coupled to the inferior inserter of FIG. 50, passing over the base inserter.
Figure 66:
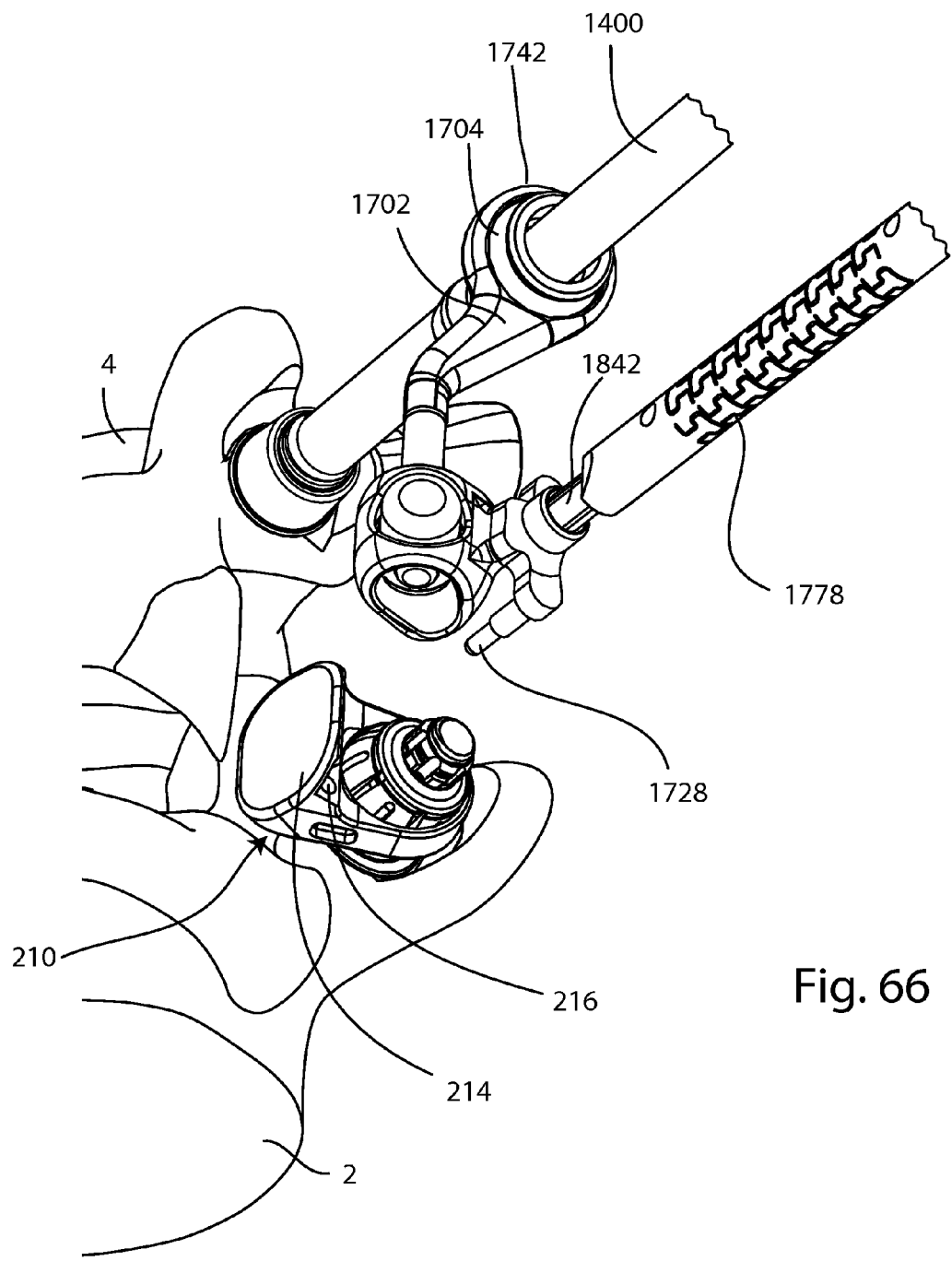
FIG. 66 is a posterior detail view of the items shown in FIG. 65.
Figure 67:
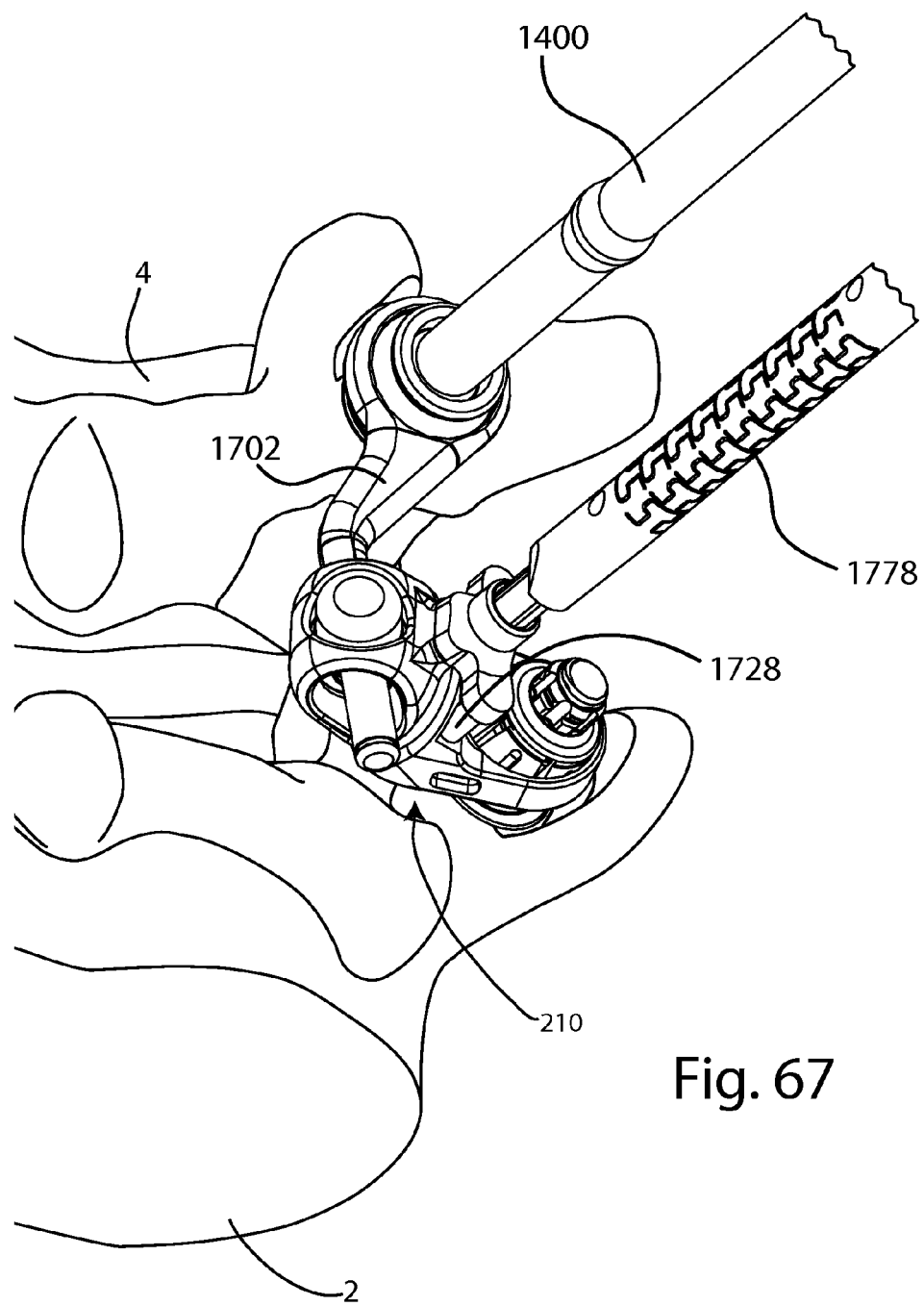
FIG. 67 is a posterior detail view of the items shown in FIG. 65, with the inferior trial coupled to the superior implant.
Figure 68:
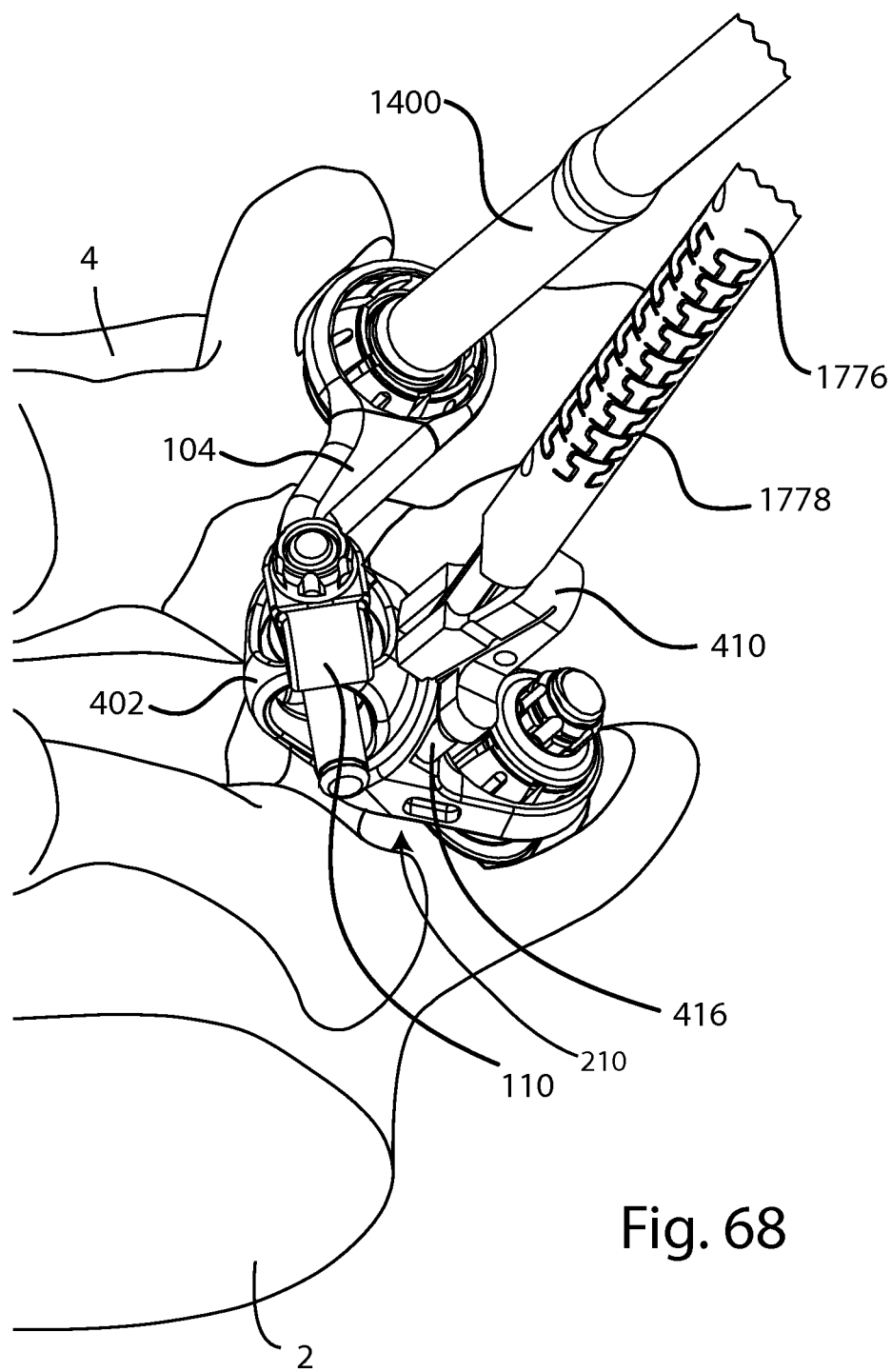
FIG. 68 is a posterior detail view of the superior implant and fixation assembly of FIG. 23 in a caudal vertebra, the base inserter of FIG. 41 coupled to an implant base in a cephalad vertebra, and an inferior implant, coupled to the inferior inserter of FIG. 50, with the inferior implant engaging the implant base.
Figure 69:
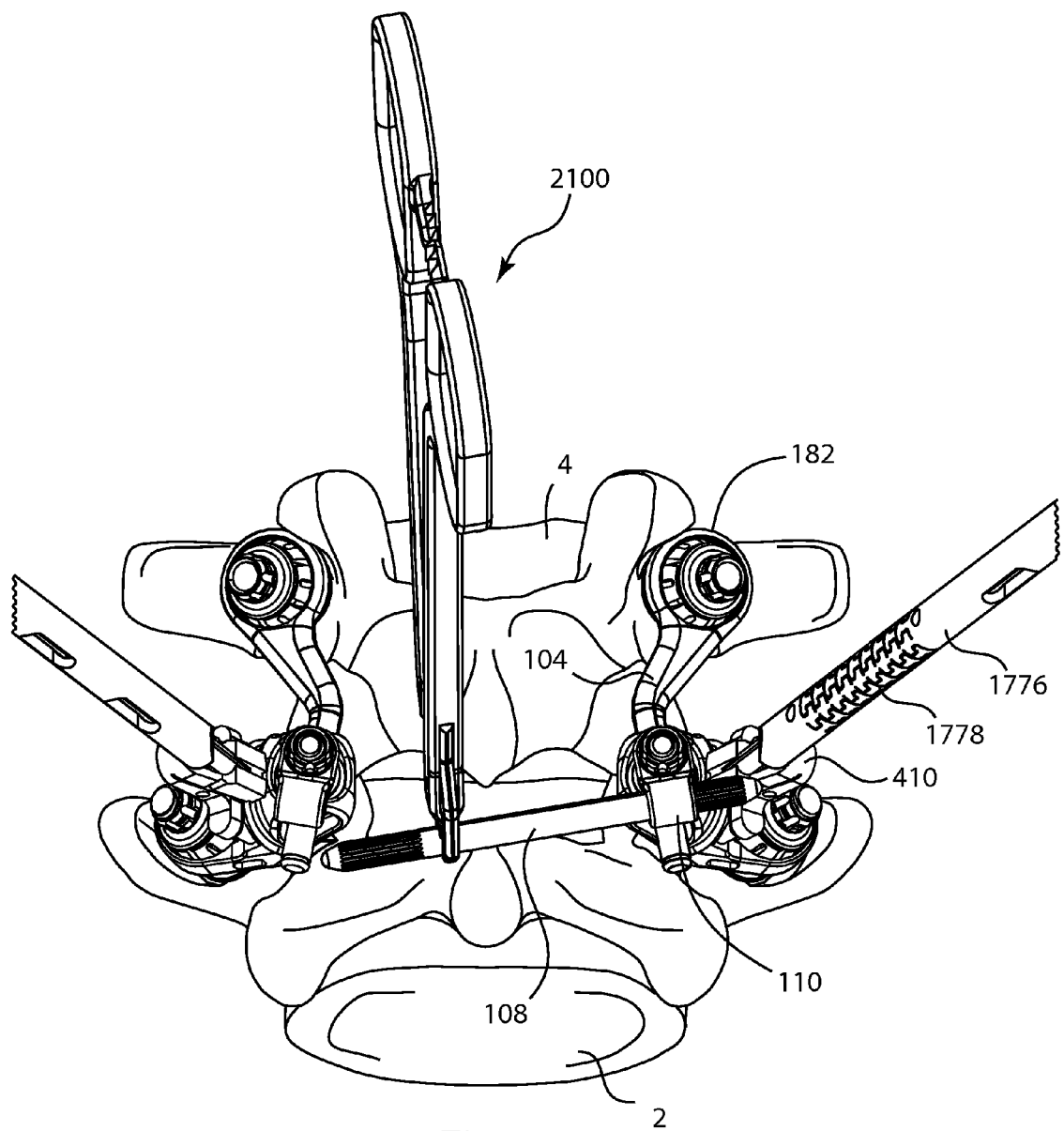
FIG. 69 is a posterior detail view showing a crosslinker engaged with one of a bilateral pair of inferior implants fixed to a cephalad vertebra.
Figure 70:
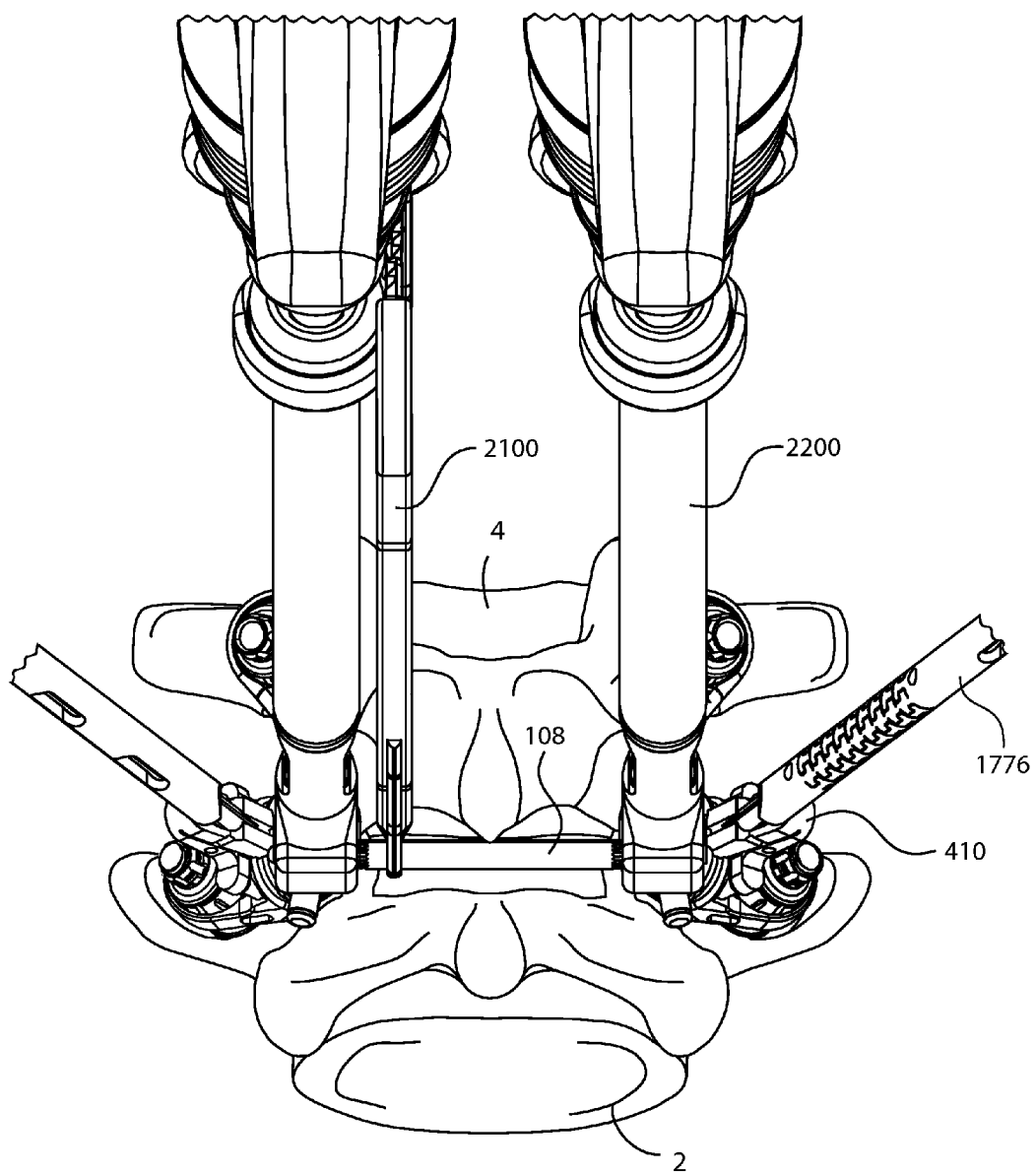
FIG. 70 is a posterior detail view showing bilateral counter torque tools stabilizing split clamps at the ends of the crosslink of FIG. 69.

Referring to FIGS. 65-67, one or more inferior trials 1700 may be used to determine the appropriate inferior facet joint implant 100 for a particular operative site. As previously described, the inferior trial 1700 substantially mimics the inferior facet joint implant 100. Furthermore, a kit of inferior trials 1700 may be provided, wherein each inferior trial 1700 in the kit has a unique configuration that corresponds to a specific inferior facet joint implant 100 configuration.

The inferior inserter 1800 is connected to a selected inferior trial 1700 by inserting the reduced diameter tip 1842 of the inferior inserter 1800 into the hole 1730 of the inferior trial 1700 and squeezing the handles 1808, 1810 of the inferior inserter 1800 together to draw the flared distal end 1826 of the inner shaft 1802 further into the distal tip 1840 of the outer sleeve 1806 so that the prongs 1844 deflect outwardly to bind within the hole 1730. The lever 1812 of the inferior inserter 1800 is spring biased so that its serrations 1798 bind against the rod 1814 to lock the inferior inserter 1800 mechanism so that it will stay connected to the inferior trial 1700 until the lever 1812 is lifted. When the lever 1812 is lifted, the spring 1816 pushes the movable handle 1810 away from the fixed handle 1808 to quickly and easily disconnect the inferior inserter 1800 from the inferior trial 1700.

With the selected inferior trial 1700 connected to the inferior inserter 1800, the trial sphere 1704 is passed over the base inserter 1400 and advanced to contact the tapered portion 872 of the implant base 870. The trial shell 1708 is manipulated with the inferior inserter 1800 to slide the pins 1728 into the openings 582 of the superior implant 210. If the pins 1728 cannot be fully inserted into the openings 582, then the selected inferior trial 1700 is unsuitable for the particular operative site or patient anatomy. In this case, the inferior trial 1700 is disconnected from the inferior inserter 1800 and a different inferior trial 1700 is selected. The trialing process is repeated with different inferior trials 1700 until a particular inferior trial 1700 is found that fits the operative site. Proper fit is demonstrated when the trial sphere is placed on the tapered portion 872 of the implant base 870 and the pins 1728 can be fully inserted into the openings 582. The inferior trial size is noted, and the same size inferior facet implant 100 is selected for permanent implantation.

The selected inferior facet implant 100 may be connected to the inferior inserter 1800 by a clip, as described previously. In a preferred embodiment, the inferior facet implant 100 includes alternate inferior articular body 402 and a split sphere 306 captive in the ring 182 of the inferior strut 104. The inferior facet implant 100 may be provided already coupled to the clip 410. Otherwise, the prongs 418 of the clip 410 may be inserted into the gripping feature 404 of inferior articular body 402. The angled holes 408 and the flared prongs 418 interact to retain the clip 410 on the inferior articular body 402. The inferior inserter 1800 is connected to the clip 410 by inserting the reduced diameter tip 1842 of the inferior inserter 1800 into the socket 414 of the clip 410 and squeezing the handles 1808, 1810 of the inferior inserter 1800 together. The prongs 1844 deflect outwardly to bind within the socket 414, and as a result, the prongs 418 are urged apart so that the inferior inserter 1800 is securely connected to the inferior facet implant 100 through the clip 410.

With the selected inferior facet implant 100 connected to the inferior inserter 1800, the split sphere 306 is placed over the base inserter 1400 and advanced to contact the tapered portion 872 of the implant base 870. The inferior articular body 402 is manipulated with the inferior inserter 1800 to slide the pins 416 of the clip 410 into the openings 582 of the superior implant 210.

The lockout tool 1600 is used to lock the inferior strut 104 to the implant base 870 in the same manner described previously. After removing the modular handle 1410, lockout tool 1600, and base inserter 1400 are removed, an optional capture nut 358 may be threaded into the threads 877 in the implant base 870. A top nut 360 is threaded onto the pedicle screw 1100 to hold the implant base 870 in the bone socket.

Optionally, a crosslink 108 may be secured between bilateral left and right inferior facet implants 100. The crosslink 108 may be grasped by an inserter, such as a locking forcep 2100, and manipulated through the interspinous space between vertebrae 2, 4 until each end of the crosslink 108 passes through the collar 164 of the split ring clamp 110 of each inferior facet implant 100.

The nut 130 of each inferior facet implant 100 is tightened so that the crosslink 108 and the inferior articular bodies 402 are locked. An optional counter torque tool 2200 may be used to stabilize the construct as the nut 130 is tightened.

The present invention includes variances of the system herein described. Alternative embodiments may include different geometries and intermediate parts. Changes in the geometry, especially on the ends of the inferior strut, may be made to facilitate instrumentation or overall function. Applications of the present invention may include single- or multi-level facet joint replacement, or other iterations in which a rod or rod-like member is fixed to a second member to attain spinal fusion.

System 10, and other facet replacement components disclosed herein, may also be implanted on multiple vertebral levels to provide facet joint replacement across several levels. In a multi-level application, additional superior implants may be added to the fixation assemblies 300 which secure the inferior struts 104, to extend the system in a cephalad direction. Similarly, to extend the system caudally, additional inferior struts coupled to inferior implants may be added to the fixation assemblies 300 which secure the original superior implants 200. Also, fusion rods (not shown) may be secured between fixation assemblies 300 on adjacent vertebrae to provide rigid fusion at a desired vertebral level.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for aligning an inferior facet joint replacement component and a superior facet joint replacement implant, comprising:
   a coupling member for connecting the inferior facet joint replacement component to the superior facet joint replacement implant; and
   an inserter tool that couples to the inferior facet joint replacement component by way of a hook extending through the coupling member
   wherein the superior facet joint replacement implant has a first configuration wherein it is polyaxially adjustable and a second configuration wherein it is in a locked fixed position and the inferior facet joint replacement component has a first configuration wherein it is polyaxially adjustable and a second configuration wherein it is in a locked fixed position, wherein when each of the superior facet joint replacement implant and the inferior facet joint replacement component are in the second configuration they are configured to articulate with one another.

2. The system of claim 1, wherein a surface of the inferior component comprises an articular surface of an inferior facet joint replacement implant.

3. The system of claim 1, wherein a surface of the inferior component comprises a mock articular surface of an inferior facet joint replacement implant trial.

4. The system of claim 1, wherein the inserter tool is movable between an unlocked configuration, in which the inferior component and the inserter tool are separable, and a locked configuration, in which the inferior component and the inserter tool are inseparable.

5. The system of claim 1, wherein the inserter tool comprises a flexible shaft that can bend to avoid obstacles in the vicinity of the shaft.

6. The system of claim 1, wherein the coupling member comprises two parallel prongs and the superior implant comprises two parallel holes sized and positioned to slidingly receive the prongs.

7. A system for facet joint replacement, comprising:
   a superior facet joint replacement implant;
   an inferior facet joint replacement implant;
   a coupling member for connecting the inferior facet joint replacement implant to the superior facet joint replacement implant;
   an inserter tool that couples to the inferior implant by way of a hook extending through the coupling member
   wherein the superior facet joint replacement implant has a first configuration wherein it is polyaxially adjustable and a second configuration wherein it is in a locked fixed position and the inferior facet joint replacement implant has a first configuration wherein it is polyaxially adjustable and a second configuration wherein it is in a locked fixed position, wherein when each of the superior facet joint replacement implant and the inferior facet joint replacement implant are in the second configuration they are configured to articulate with one another.

8. The system of claim 7, wherein the inferior implant comprises:
   a disposable clip comprising the coupling member;
   wherein a second coupling portion of the clip engages a complementary second coupling portion of the inferior implant to couple the clip to the inferior implant in a fixed orientation;
   wherein a third coupling portion of the clip engages a complementary third coupling portion of the inserter tool to couple the inferior facet joint replacement implant to the inserter tool in a set orientation;
   wherein each of the inferior implant and an inferior facet joint replacement implant trial independently couples to the superior implant in the same orientation.

9. A system for facet joint replacement, comprising:
   a superior facet joint replacement implant;
   an inferior facet joint replacement implant trial;
   a coupling member for connecting the inferior facet joint replacement implant trial to the superior facet joint replacement implant; and an inserter tool comprising two prongs and a hook, whereby the inserter tool couples to the interior facet joint replacement implant trial by way of the hook extending through the coupling member wherein the superior facet joint replacement implant has a first configuration wherein it is polyaxially adjustable and a second configuration wherein it is in a locked fixed position and the inferior facet joint replacement implant trial has a first configuration wherein it is polyaxially adjustable and a second configuration wherein it is in a locked fixed position, wherein when each of the superior facet joint replacement implant and the inferior facet joint replacement implant trial are in the second configuration they are configured to articulate with one another.

10. The system of claim 9, wherein a surface of the inferior trial comprises a mock articular surface.

11. The system of claim 9, wherein the inserter tool is movable between an unlocked configuration, in which the inferior trial and the inserter tool are separable, and a locked configuration, in which the inferior trial and the inserter tool are inseparable.

* * * * *